US012782281B2

(12) United States Patent
Anazawa et al.

(10) Patent No.: US 12,782,281 B2
(45) **Date of Patent: *Nov. 3, 2026**

(54) ANALYSIS SYSTEM AND ANALYSIS METHOD

(71) Applicant: Hitachi High-Tech Corporation, Tokyo (JP)

(72) Inventors: Takashi Anazawa, Tokyo (JP); Ryoji Inaba, Tokyo (JP); Shuhei Yamamoto, Tokyo (JP); Taro Nakazawa, Tokyo (JP); Michiru Fujioka, Tokyo (JP); Motohiro Yamazaki, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 19/076,669

(22) Filed: Mar. 11, 2025

(65) Prior Publication Data

US 2025/0271360 A1 Aug. 28, 2025

Related U.S. Application Data

(63) Continuation of application No. 17/612,046, filed as application No. PCT/JP2020/017202 on Apr. 21, 2020, now Pat. No. 12,276,608.

(30) Foreign Application Priority Data

May 22, 2019 (JP) ................................ 2019-096011

(51) Int. Cl.

*G01N 21/64* (2006.01)
*C12Q 1/6869* (2018.01)
(Continued)

(52) U.S. Cl.

CPC .......... *G01N 21/64* (2013.01); *C12Q 1/6869* (2013.01); *G01N 21/59* (2013.01);
(Continued)

(58) Field of Classification Search

CPC .......... G01N 15/1425; G01N 15/1429; G01N 21/59; G01N 21/64; G01N 21/6408;
(Continued)

(56) References Cited

U.S. PATENT DOCUMENTS

| | | |
|---|---|---|
| 5,096,807 A | 3/1992 | Leaback |
| 6,403,947 B1 | 6/2002 | Hoyt |

(Continued)

FOREIGN PATENT DOCUMENTS

| | | |
|---|---|---|
| JP | 2006-515428 A | 5/2006 |
| JP | 3897277 B | 3/2007 |

(Continued)

OTHER PUBLICATIONS

Great Britain Search & Examination Report issued Sep. 21, 2023 for Great Britain Patent Application No. 2311980.3.

(Continued)

*Primary Examiner* — Gordon J Stock, Jr.
(74) *Attorney, Agent, or Firm* — Volpe Koenig

(57) ABSTRACT

In an analysis method and an analysis system for detecting fluorescences from each of a plurality of light-emitting points in a plurality of wavelength bands in order to identify fluorescence emissions of a plurality of types of fluorophores from the plurality of light-emitting points, spatial crosstalk and spectral crosstalk are present between the plurality of light-emitting points and between the plurality of wavelength bands, and then performance of the identification is reduced. The spatial crosstalk and the spectral crosstalk are eliminated and concentrations of each of the plurality of types of fluorophores at each of the plurality of
(Continued)

light-emitting points are derived by inputting all detection signals in the plurality of wavelength bands for the plurality of light-emitting points to a predetermined arithmetic operation expression.

9 Claims, 33 Drawing Sheets

(51) Int. Cl.
*G01N 21/59* (2006.01)
*G01N 27/447* (2006.01)

(52) U.S. Cl.
CPC ....... *G01N 21/6456* (2013.01); *G01N 27/447* (2013.01); *G01N 27/44721* (2013.01); *G01N 2021/6421* (2013.01); *G01N 2021/6441* (2013.01)

(58) Field of Classification Search
CPC ........... G01N 21/6456; G01N 21/6458; G01N 21/6486; G01N 27/447; G01N 27/44721; G01N 2021/6421; G01N 2021/6441; C12Q 1/6869; C12M 1/00; C12M 1/34
See application file for complete search history.

(56) References Cited

U.S. PATENT DOCUMENTS

| | | | | |
|---|---|---|---|---|
| 7,222,059 | B2 | 5/2007 | Izmailov | |
| 7,286,719 | B2 | 10/2007 | Riley | |
| 7,532,326 | B2 | 5/2009 | Corcoran | |
| 7,692,783 | B2 | 4/2010 | Lundquist | |
| 7,839,507 | B2 | 11/2010 | Gunstream | |
| 8,149,399 | B2 | 4/2012 | Lundquist | |
| 8,182,993 | B2 | 5/2012 | Tomaney | |
| 8,410,454 | B2 * | 4/2013 | Bouzid | G02B 21/16 250/458.1 |
| 8,475,640 | B2 * | 7/2013 | Pang | G01N 27/44782 204/452 |
| 8,703,422 | B2 * | 4/2014 | Tomaney | C12Q 1/6874 435/6.12 |
| 8,817,115 | B1 | 8/2014 | Venkatachalam | |
| 9,170,198 | B2 | 10/2015 | Estrada | |
| 11,441,999 | B2 | 9/2022 | Sharpe | |
| 11,593,649 | B2 | 2/2023 | Kostem | |
| 11,774,365 | B2 | 10/2023 | Cheng | |
| 11,860,094 | B2 | 1/2024 | Anazawa | |
| 11,908,548 | B2 * | 2/2024 | Dutta | G06F 16/58 |
| 12,276,608 | B2 * | 4/2025 | Anazawa | C12Q 1/6869 |
| 2002/0140934 | A1 | 10/2002 | Inaba et al. | |
| 2004/0168919 | A1 | 9/2004 | Kurt et al. | |
| 2006/0094109 | A1 | 5/2006 | Trainer | |
| 2007/0194249 | A1 | 8/2007 | Gavrilov et al. | |
| 2008/0033677 | A1 | 2/2008 | Tomaney | |
| 2011/0120869 | A1 | 5/2011 | Pang | |
| 2012/0015825 | A1 | 1/2012 | Zhong | |
| 2013/0124100 | A1 * | 5/2013 | Drmanac | G16B 30/10 702/20 |
| 2015/0177148 | A1 | 6/2015 | Estrada | |
| 2018/0024061 | A1 | 1/2018 | Anazawa et al. | |
| 2018/0275059 | A1 | 9/2018 | Rebetez et al. | |
| 2020/0003728 | A1 | 1/2020 | Majumdar | |
| 2023/0124845 | A1 | 4/2023 | Fujioka | |
| 2024/0035979 | A1 | 2/2024 | Cheng | |

FOREIGN PATENT DOCUMENTS

| | | | | |
|---|---|---|---|---|
| JP | 2018-529947 | A | 10/2018 | |
| JP | 6456983 | B | 1/2019 | |
| WO | 2018/151843 | A2 | 8/2018 | |
| WO | WO-2025041344 | A1 * | 2/2025 | G01N 27/44721 |

OTHER PUBLICATIONS

Great Britain Search & Examination Report issued Sep. 21, 2023 for Great Britain Patent Application No. 2312063.7.

Kheterpal, Indu et al., "A three-wavelength labeling approach for DNA sequencing using energy transfer primers and capillary electrophoresis," Electrophoresis, 19, 1998, pp. 1403-1414. (Year: 1998).

* cited by examiner 60,000
30,000
0
ABSOLUTE SIGNAL INTENSITY
α
β
γ

100
50
0
ABSOLUTE SIGNAL INTENSITY
α
β
γ

100%
10%
1%
0.1%
0.01%
0.001%
RELATIVE SIGNAL INTENSITY
α, β, γ

-7 -6 -5 -4 -3 -2 -1 0 +1 +2 +3 +4 +5 +6 +7
DISTANCE FROM CENTER OF IMAGE
OF LIGHT-EMITTING POINT (mm)

P(1)
Z(1,1)
Z(1,2)

P(2)

Z(2,1)
Z(2,2)
FLUORESCENCE INTENSITY
ELECTROPHORESIS TIME
200
100
0
1.5
1.0
0.5
-0.5
300
400

ANALYSIS SYSTEM AND ANALYSIS METHOD

CROSS-REFERENCE TO RELATED APPLICATIONS

This application is a continuation of U.S. patent application Ser. No. 17/642,046, filed Nov. 17, 2021, which is a National Stage filing of International Patent Application No. PCT/JP2020/017202, filed Apr. 21, 2020, which claims the benefit of Japanese Patent Application No. 2019-096011, filed May 22, 2019, the entire contents of which are incorporated herein by reference.

TECHNICAL FIELD

The present disclosure relates to an analysis method and an analysis system for detecting fluorescences emitted from a plurality of types of fluorophores at a plurality of light-emitting points while identifying their types of fluorophores.

BACKGROUND ART

In recent years, a multi-capillary electrophoresis system has been widely used. The multi-capillary electrophoresis system has filled with an a plurality of capillaries electrophoretic separation medium such as an electrolyte solution or an electrolyte solution containing a polymer gel or a polymer. The multi-capillary electrophoresis system performs multiple electrophoretic analyses in parallel. Targets to be analyzed are wide-ranging, including small molecules and polymers such as proteins and nucleic acids. There are many measurement modes such as a mode of irradiating light-absorbing points of capillaries with lamp light and detecting absorption of the lamp light generated when the targets to be analyzed pass through the light-absorbing points, and a mode of irradiating the light-emitting points of the capillaries with the laser light and detecting fluorescences or scattered lights generated when the targets to be analyzed pass through the light-emitting points.

For example, in PTL 1, A capillaries (A is an integer of 2 or more) around A light-emitting points on the. A capillaries are arranged on the same plane (an arrangement plane). A laser beam is introduced from a side of the arrangement plane to simultaneously irradiate the light-emitting points of all the capillaries. Fluorescences emitted from the light-emitting points are wavelength-dispersed and collectively detected from a direction perpendicular to the arrangement plane. In a detection device, the fluorescences emitted from the A light-emitting points are collectively collimated by one condenser lens, are transmitted through one transmission grating. Images of first-order diffracted lights of the fluorescences are collectively formed on one two-dimensional sensor by one imaging lens. Here, the wavelength-dispersed images of the fluorescences from the capillaries do not overlap each other on the two-dimensional sensor by setting the arrangement direction of the A light-emitting points and the wavelength-dispersion direction by the grating to be perpendicular to each other. B color detection (B is an integer of 1 or more) can be performed by setting detection regions of B wavelength bands on the wavelength-dispersed images for the capillaries. When B=1, it is called monochromatic detection. When B≥2, it is called multicolor detection. In the multi-capillary electrophoresis system of PTL 1, for example, DNA sequencing of different DNA samples by the Sanger method can be performed in the capillaries. In the Sanger method, DNA fragments contained in the DNA samples are labeled with four types of fluorophores according to terminal base species A, C, G, and T. The fluorescences emitted from the fluorophores are identified by the multicolor detection.

In PTL 2, all A capillaries (A is an integer of 2 or more) around A light-emitting points on the A capillaries are arranged on the same plane (an arrangement plane). A laser beam is introduced from a side of the arrangement plane to collectively irradiate the light-emitting points of all the capillaries. Fluorescences emitted from the light-emitting points are divided into components of different wavelengths and are collectively detected from a direction perpendicular to the arrangement plane. In a detection device, the fluorescences from the A light-emitting points are individually collimated by A condenser lenses to form A light fluxes. The light fluxes are incident in parallel on one set of dichroic mirror array in which B dichroic mirrors (B is an integer of 1 or more) are arranged. Each of the light fluxes is divided into B light fluxes with different wavelength bands. A total of A×B light fluxes are incident in parallel on one two-dimensional sensor, and A×B divided images are formed on the two-dimensional sensor. Here, the A×B divided images do not overlap each other on the two-dimensional sensor image by setting the arrangement direction of the A light-emitting points and B dividing directions of the light fluxes by the dichroic mirror array to be perpendicular to each other, and therefore A×B detection regions can be set on the two-dimensional sensor image. In this manner, B color detection for the capillaries can be performed. Accordingly, similarly to the case of PTL 1, in the multi-capillary electrophoresis system of PTL 2, for example, the DNA sequencing of different DNA samples by the Sanger method can be performed in the capillaries.

However, in general, the fluorescences of the plurality of types of fluorophores cannot be identified only by performing the multicolor detection. This is because, since fluorescence spectra of the fluorophores overlap each other, the fluorescences of the plurality of types of fluorophores mix in any one wavelength band (referred to as spectral crosstalk in the present disclosure). Further, that is because, the plurality of types of fluorophores having different concentrations may simultaneously emit the fluorescences. Thus, the spectral crosstalk is eliminated, and the above-described identification can be performed by the next step (referred to as color conversion in the present disclosure).

The B color detection of the fluorescences of C types (C is an integer of 1 or more) of fluorophores is performed in detection regions of B types (B is an integer of 1 or more) of wavelength bands at each time for each of the A light-emitting points (A is an integer of 2 or more). Where B≥C. The color conversion of the results of the B color detection is performed to acquire concentrations of the C types of fluorophores at each time for each of the light-emitting points. The fluorescences of the fluorophores D(c) (c=1, 2, . . . , and C) are detected in detection regions W(b) (b=1, 2, . . . , and B) of different wavelength bands for each of the light-emitting points P(a) (a=1, 2, . . . , and A). At any time, the concentrations of the fluorophores D(c) at the light-emitting points P(a) are Z(c), and signal intensities of the detection regions W(b) for the light-emitting points P(a) are X(b). Here, when X is a matrix of B rows and 1 column with the signal intensities X(b) as elements, Z is a matrix of C rows and 1 column with the concentrations Z(c) as elements, and Y is a matrix of B rows and C columns with Y(b)(c) as elements, the following equations are established. (Equation 1) to (Equation 4) are relational expressions of b and c but are not a relational expression of a, and therefore established independently of the light-emitting points P(a). When B=1 in the case of the monochromatic detection, C=1 is obtained because of B≥C, and X, Y, and Z are not matrices.

[Equation 1]

$$X = Y \times Z \quad \text{(Equation 1)}$$

[Equation 2]

$$X = \begin{pmatrix} X(1) \\ \vdots \\ X(B) \end{pmatrix} \quad \text{(Equation 2)}$$

[Equation 3]

$$Y = \begin{pmatrix} Y(1)(1) & \cdots & Y(1)(C) \\ \vdots & \ddots & \vdots \\ Y(B)(1) & \cdots & Y(B)(C) \end{pmatrix} \quad \text{(Equation 3)}$$

[Equation 4]

$$Z = \begin{pmatrix} Z(1) \\ \vdots \\ Z(C) \end{pmatrix} \quad \text{(Equation 4)}$$

Here, each element Y(b)(c) of the matrix Y of B rows and C columns represents signal intensity ratio at which the fluorescence of the fluorophore D(c) are detected in the detection region W(b). One column $Y(b)(c_0)$(b=1, 2, . . . , and B) of the matrix Y can be determined by inducing fluorescence of any one type of fluorophore $D(c_0)$ alone. Here, since it is generally difficult to control the concentration of the fluorophore $D(c_0)$, it is convenient to standardize the one column $Y(b)(c_0)$. For example, among the B elements, the maximum element may be set to 1, and the other elements may be ratios with respect to the maximum element, respectively. Alternatively, the elements may be ratios such that the sum of the B elements is 1. That is, the following equation is obtained:

[Equation 5]

$$\sum_{b=1}^{B} Y(B)(C_0) = 1. \quad \text{(Equation 5)}$$

All the columns of the matrix Y can be determined by sequentially performing the above steps for all the C types of fluorophores D(c). The matrix Y is determined only by characteristics of the fluorophores D(c) and the detection regions W(b) of different wavelength bands, and does not change during the electrophoresis analysis. As long as conditions such as the optical system, the fluorophores D(c), and the detection regions W(b) are fixed, the matrix Y is kept constant even for different electrophoretic analyses. Accordingly, the concentrations Z(c) of the fluorophores D(c) at each time are obtained from the signal intensities X(b) of the detection regions W(b) at each time for each of the light-emitting points by the following equation.

[Equation 6]

$$Z = Y^{-} \times X \quad \text{(Equation 6)}$$

Here, $Y^{-}$ of C rows and B columns is a general inverse matrix of Y, and is obtained by $Y^{-}=(Y^{T}\times Y)^{-1}\times Y^{T})$. When the matrix Y is a square matrix of B=C, $Y^{-}$ is equal to the inverse matrix $Y^{-1}$.

(Equation 1) corresponds simultaneous equations indicating a relationship between concentrations of C types of fluorophores which are unknown and B-color fluorescence intensities which are known. (Equation 6) corresponds to obtaining a solution of the simultaneous equations. Accordingly, in general, as described above, a condition of B≥C is required. When B<C, a solution cannot be uniquely obtained (that is, there may be a plurality of solutions), and the color conversion cannot be executed as in (Equation 6).

As an example, the case where C=4 for the Sanger method and B=4 for four-color detection will be described in detail. When copies of various length DNA fragments complementary to a template DNA are prepared by the Sanger reaction, the DNA fragments are labeled with four types of fluorophores D(1), D(2), D(3), and D(4) according to terminal base species A, C, G, and T of the DNA fragments, respectively. The DNA fragments are sequentially irradiated with a laser beam to emit the fluorescences while being separated by their lengths by electrophoresis. Four colors of the fluorescences are detected in the detection regions W(1), W(2), W(3), and W(4) of the four types of wavelength bands corresponding to maximum wavelengths of the fluorescences of the fluorophores D(1), D(2), D(3), and D(4). Pieces of time-series data of the signal intensities X(1), X(2), X(3), and X(4)(referred to as pieces of raw data in the present disclosure, where B=4 and C=4 are not always the case) are obtained. Assuming that the concentrations of the fluorophores D(1), D(2), D(3), and D(4) at each time are Z(1), Z(2), Z(3), and Z(4), respectively, (Equation 1) is given by the following equation.

[Equation 7]

$$\begin{pmatrix} X(1) \\ X(2) \\ X(3) \\ X(4) \end{pmatrix} = \begin{pmatrix} Y(1)(1) & Y(1)(2) & Y(1)(3) & Y(1)(4) \\ Y(2)(1) & Y(2)(2) & Y(2)(3) & Y(2)(4) \\ Y(3)(1) & Y(3)(2) & Y(3)(3) & Y(3)(4) \\ Y(4)(1) & Y(4)(2) & Y(4)(3) & Y(4)(4) \end{pmatrix} \times \begin{pmatrix} Z(1) \\ Z(2) \\ Z(3) \\ Z(4) \end{pmatrix} \quad \text{(Equation 7)}$$

Here, the elements Y(b)(c) of the 4×4 matrix Y represent intensity ratios at which the fluorescences of the fluorophores D(c) (c is 1, 2, 3, or 4) are detected in the wavelength bands W(b) (b is 1, 2, 3, or 4) based on the spectral crosstalk. Each element Y(b)(c) of the matrix Y can be determined by electrophoretic analysis of samples in which each fluorophore D(c) (c is 1, 2, 3, or 4) emits the fluorescence alone in each of the capillaries. For example, four color fluorescence intensities X(1), X(2), X(3), and X(4) when the fluorophore D(1) emits the fluorescence alone provide the elements Y(1)(1), Y(2)(1), Y(3)(1), and Y(4)(1). The four color fluorescence intensities X(1), X(2), X(3), and X(4) when the fluorophore D(2) emits the fluorescence alone provide the elements Y(1)(2), Y(2)(2), Y(3)(2), and Y(4)(2). The same applies to the fluorophores D(3) and D(4). Each Y(b)(c) is a fixed value determined only by characteristics of the fluorophore D(c) and the wavelength band W(b), and does not change during electrophoresis. Accordingly, for each of the capillaries, the concentrations of the fluorophores D(1), D(2), D(3), and D(4) at each time are obtained from the four color fluorescence intensities X(1), X(2), X(3), and X(4) at each time by the following equation obtained by embodying (Equation 6).

[Equation 8]

$$\begin{pmatrix} Z(1) \\ Z(2) \\ Z(3) \\ Z(4) \end{pmatrix} = \begin{pmatrix} Y(1)(1) & Y(1)(2) & Y(1)(3) & Y(1)(4) \\ Y(2)(1) & Y(2)(2) & Y(2)(3) & Y(2)(4) \\ Y(3)(1) & Y(3)(2) & Y(3)(3) & Y(3)(4) \\ Y(4)(1) & Y(4)(2) & Y(4)(3) & Y(4)(4) \end{pmatrix}^{-1} \times \begin{pmatrix} X(1) \\ X(2) \\ X(3) \\ X(4) \end{pmatrix} \quad \text{(Equation 8)}$$

In this manner, the spectral crosstalk is eliminated by multiplying the four color fluorescence intensities by the inverse matrix $Y^{-1}$. The pieces of time-series data of the concentrations of the four types of fluorophores, that is, the concentrations of the DNA fragments having the four types of bases at their terminals are obtained (the pieces of time-series data are referred to as pieces of color-converted data in the present disclosure. But is not limited to the case of B=4 and C=4).

As described above, the above color conversion step is performed independently for each of the A capillaries. The color conversion is established on the premise that crosstalk between the capillaries (referred to as spatial crosstalk in the present disclosure) is sufficiently small. That is, the ratio of the fluorescence signal intensity from one capillary mixed with the fluorescence intensity from another capillary is sufficiently small. Accordingly, the aforementioned step of determining the matrix Y by sequentially performing the step of inducing one type of fluorophore $D(c_0)$ to emit the fluorescence alone for the C types of fluorophores D(c) is performed substantially simultaneously for the A capillaries, and the matrices Y for the A capillaries are obtained in parallel. This step is an essential step for deriving the matrix Y in a short time and without hassle.

The spatial crosstalk is basically reduced by devising the optical system. There is also an attempt to reduce the spatial crosstalk by calculation processing. In PTL 3, images of fluorescences emitted from not a plurality of capillaries but a plurality of light-emitting points randomly arranged on a plane are collectively formed on one two-dimensional sensor by one condenser lens. The fluorescence from each of the light-emitting points is detected as signal intensity of a detection region provided at the position of the fluorescence image on the two-dimensional sensor. It has been found that a ratio of the spatial crosstalk from the signal intensity of the fluorescence emitted from one arbitrary light-emitting point to the signal intensity of the fluorescence emitted from another light-emitting point can be expressed as a function of a distance between the two light-emitting points, i.e., a distance between the corresponding two detection regions and decreases with the distance. The function is obtained in advance, and then, in the fluorescence images of the plurality of light-emitting points randomly arranged on the plane, mutual spatial crosstalk is obtained from the distance between any two detection regions by the function. The obtained spatial crosstalk is subtracted from the original fluorescence images. Thus, the spatial crosstalk is reduced.

CITATION LIST

Patent Literature

PTL 1: JP 3897277 B
PTL 2: JP 6456983 B
PTL 3: JP 2018-529947 A

SUMMARY OF INVENTION

Technical Problem

In both the cases of PTL 1 and PTL 2, since the fluorescence images from the A light-emitting points on the A capillaries are separated on the two-dimensional sensor, the spatial crosstalk is suppressed to be basically low. Causes of the spatial crosstalk are considered to be (1) aberrations of lenses, (2) multiple reflections of fluorescences between elements such as multiple capillaries, lenses, filters, dichroic mirrors, and a two-dimensional sensor inside an optical system, (3) blooming between pixels of the two-dimensional sensor. In order to reduce the spatial crosstalk, it is necessary to construct the optical system so as to minimize the influence of the above causes (1) to (3). For example, in order to suppress the influence of the cause (2), it is effective to apply an antireflective coating with low reflectance to the lenses. However, it is impossible to make the spatial crosstalk completely zero. Since the spatial crosstalk effectively increases a lower detection limit in the detection of the fluorescence emitted from any one capillary, the spatial crosstalk can decrease detection sensitivity and detection dynamic range. Accordingly, it is extremely important to reduce the spatial crosstalk as much as possible in order to alleviate or solve the above problems.

The present inventors have attempted to reduce the spatial crosstalk in the optical system of PTL 1 or PTL 2 by the method of PTL 3, but it does not work well. First, the case of the monochromatic detection of B=1 will be described. Let $X(\alpha)(\beta)$ be the signal intensity of the detection region $\beta$ for the emission point $\alpha$, which is any one emission point of the A emission points. And let $X(\alpha')(\beta)$ be the signal intensity of the detection region $\beta$ for the emission point $\alpha'$, which is any one emission point other than the emission point $\alpha$ ($\alpha \neq \alpha'$). It was found that the spatial crosstalk from the signal intensity $X(\alpha)(\beta)$ to the signal intensity $X(\alpha')(\beta)$ tended to decrease with a distance between the two detection regions. However, it was also found that the spatial crosstalk cannot be expressed by a function of only the above distance. For example, even when the distance between the two detection regions is constant, the ratio of the spatial crosstalk is different between a case where the two detection regions are positioned near a central axis of the optical system and a case where the two detection regions are positioned far from the central axis of the optical system. Further, the ratio of the spatial crosstalk from one to the other of the two detection regions is different from the ratio of the spatial crosstalk from the other to one. In the case of the multicolor detection of $B \geq 2$, the method of PTL 3 does not function more. In addition to the above, let $X(\alpha')(\beta')$ be the signal intensity of the detection region $\beta'$ for the emission point x'. Spatial crosstalk from the signal intensity $X(\alpha)(\beta)$ to the signal intensity $X(\alpha')(\beta')$ ($\beta=\beta'$ or $\beta \neq \beta'$, $\beta=\beta$ means both are detection regions of the same wavelength band, and $\beta \neq \beta'$ means both are detection regions of different wavelength bands) cannot be expressed by a function of the distance between the two detection regions. In particular, in the case of $\beta \neq \beta'$, since the spatial crosstalk and the spectral crosstalk are mixed, the crosstalk between the two detection regions cannot be essentially expressed by a function of the distance between the two detection regions. The present problem will be described in detail in [Description of Embodiments].

Thus, the present disclosure proposes a method for identifying light emissions emitted from a plurality of light-emitting points and detecting the light emissions independently by reducing spatial crosstalk between the plurality of light-emitting points by calculation processing. Such spatial crosstalk occurs in any optical system that detects light emissions emitted from a plurality of light-emitting points. The present disclosure further proposes a method for identifying fluorescence emissions of a plurality of types of fluorophores from a plurality of light-emitting points and detecting the fluorescences independently by reducing spatial crosstalk between the plurality of light-emitting points and spectral crosstalk between the plurality of types of fluorophores for each light-emitting point by calculation processing. Such spatial crosstalk and spectral crosstalk occur in any optical system that detects fluorescences of a plurality of types of fluorophores which are emitted from a plurality of light-emitting points. Alternatively, the present disclosure proposes a method for identifying absorptions at a plurality of light-absorbing points and detecting the absorptions independently by reducing spatial crosstalk between the plurality of light-absorbing points by calculation processing. Such spatial crosstalk in any optical system that detects absorptions at a plurality of light-absorbing points. The present disclosure further proposes a method for identifying absorptions of a plurality of types of light absorbers at a plurality of light-absorbing points and detecting the absorptions independently by reducing spatial crosstalk between the plurality of light-absorbing points and spectral crosstalk between the plurality of types of light absorbers for each light-absorbing point by calculation processing. Such spatial crosstalk and spectral crosstalk occur in any optical system that detects absorptions of a plurality of types of light absorbers at a plurality of absorption points.

Solution to Problem

In the optical system of PTL 1, PTL 2, or the like, a case where fluorescence emissions of C types (C is an integer of 1 or more) of fluorophores are detected in detection regions of B (B is an integer of 1 or more) wavelength bands for A light-emitting points (A is an integer of 2 or more) will be described. Here, different wavelength components of the fluorescences are respectively detected in the detection regions of different wavelength bands. Also the different types of the fluorophores respectively emit the fluorescences having different fluorescence spectra. The fluorescence emissions of the fluorophores D(a, c) (c=1, 2, . . . , and C) present at the light-emitting points P(a) (a=1, 2, . . . , and A) are detected in the detection regions W(a, b) (b=1, 2, . . . , and B) of the different wavelength bands for each light-emitting point P(a). It is assumed that concentrations of the fluorophores D(a, c) at the light-emitting points P(a) at any time are Z(a, c). Further, it is assumed that signal intensities of the detection regions W(a', b) for the light-emitting points P(a') are X(a', b). Here, the present inventors have found for the first time that the following equations in which X is a matrix of A×B rows and 1 column with X(a', b) as elements, Z is a matrix of A×C rows and 1 column with Z(a, c) as elements, and Y is a matrix of (A×B) rows and (A×C) columns with Y(a', b)(a, c) as elements are established.

[Equation 9]

$$X = Y \times Z \quad \text{(Equation 9)}$$

[Equation 10]

$$X = \begin{pmatrix} X(1,1) \\ \vdots \\ X(1,B) \\ X(2,1) \\ \vdots \\ X(A,B) \end{pmatrix} \quad \text{(Equation 10)}$$

-continued

[Equation 11]

$$Y = \begin{pmatrix} Y(1,1)(1,1) & \ldots & Y(1,1)(1,C) & Y(1,1)(2,1) & \ldots & Y(1,1)(A,C) \\ \vdots & \ddots & \vdots & \vdots & \iddots & \vdots \\ Y(1,B)(1,1) & \ldots & Y(1,B)(1,C) & Y(1,B)(2,1) & \ldots & Y(1,B)(A,C) \\ Y(2,1)(1,1) & \ldots & Y(2,1)(1,C) & Y(2,1)(2,1) & \ldots & Y(2,1)(A,C) \\ \vdots & \iddots & \vdots & \vdots & \ddots & \vdots \\ Y(A,B)(1,1) & \ldots & Y(A,B)(1,C) & Y(A,B)(2,1) & \ldots & Y(A,B)(A,C) \end{pmatrix} \quad \text{(Equation 11)}$$

[Equation 12]

$$Z = \begin{pmatrix} Z(1,1) \\ \vdots \\ Z(1,C) \\ Z(2,1) \\ \vdots \\ Z(A,C) \end{pmatrix} \quad \text{(Equation 12)}$$

(Equation 9) looks the same as (Equation 1), but both the equations are completely different when (Equation 1) to (Equation 4) are compared with (Equation 9) to (Equation 12). (Equation 9) to (Equation 12) are not only relational expressions of b and c but also relational expressions of a, and the different light-emitting points P(a) are therefore related to each other. That is, (Equation 9) to (Equation 12) are constructed by collectively considering spatial crosstalk and spectral crosstalk between different light-emitting points P(a) in addition to spectral crosstalk for the same light-emitting point P(a). Accordingly (Equation 9) to (Equation 12) are essentially different from (Equation 1) to (Equation 4).

Here, each element Y(a', b)(a, c) of the matrix Y of the (A×B) rows and the (A×C) columns represents (1) the signal intensity ratio of the fluorescence emission of the fluorophore D(a', c) at the light-emitting point P(a') detected in any detection region W(a', b) due to the spectral crosstalk when a'=a, that is, the spectral crosstalk for the same light-emitting point. In addition, each element Y(a', b)(a, c) represents (2) the signal intensity ratio of the fluorescence emission of the fluorophore D(a, c) at the light-emitting point P(a) detected in any detection region W(a', b) due to the spatial crosstalk and the spectral crosstalk when a'≠a, that is, the spatial crosstalk and the spectral crosstalk between different light-emitting points. One column Y(a, b)($a_0$, $c_0$) (a=1, 2, . . . , and A, and b=1, 2, . . . , and B) of the matrix Y can be determined by causing any one type of fluorophore D($a_0$, $c_0$) to emit fluorescence alone at any one light-emitting point P($a_0$). Here, since it is generally difficult to control the concentration of the fluorophore D($a_0$, $c_0$), it is convenient to standardize each column Y(a, b)($a_0$, $c_0$) individually. For example, among the A×B elements in each column, the maximum element may be set to 1, and the other elements may be indicated by a ratio with respect to the maximum value. Alternatively, the ratio of the elements may be determined such that the sum of the A×B elements is 1. That is, it is assumed that the following equation is established:

[Equation 13]

$$\sum_{b=1}^{B} \sum_{a=1}^{A} Y(a,b)(a_0,c_0) = 1. \quad \text{(Equation 13)}$$

All the columns of the matrix Y can be determined by sequentially performing the above steps for all the combinations of any one of the C types of fluorophores D(a, c) and any one of the A light-emitting points P(a). The matrix Y is determined only by the characteristics of the light-emitting points P(a), the fluorophores D(a, c), and the detection regions W(a, b), and does not change during electrophoresis analysis. As long as conditions such as the optical system, the light-emitting points P(a), the fluorophores D(a, c), and the detection regions W(a, b) are fixed, the matrix Y is kept constant even for different electrophoresis analyses. Accordingly, for each of the light-emitting points, the concentrations Z(a, c) of the fluorophores D(a, c) at each time are obtained from the signal intensities X(a, b) of the detection regions W(a, b) at each time by the following equation.

[Equation 14]

$$Z = Y^{-} \times X \quad \text{(Equation 14)}$$

(Equation 14) looks the same as (Equation 6), but both the equations are completely different from each other when (Equation 2) to (Equation 4) and (Equation 6) are compared with (Equation 10) to (Equation 12) and (Equation 14). According to (Equation 14), both the spectral crosstalk and the spatial crosstalk can be eliminated by multiplying the A×B signal intensities X(a, b) by the pre-derived general inverse matrix $Y^{-}$ of the matrix Y at each time, and the A×C concentrations Z(a, c) can be obtained. $Y^{-}$ is a matrix of (A×C) rows and (A×B) columns. In the present disclosure, the elimination of the spectral crosstalk is referred to as color conversion, and the elimination of the spatial crosstalk is referred to as spatial correction. That is, the (A×C)×(A×B) elements of $Y^{-}$ include both a portion for executing the color conversion and a portion for executing the spatial correction. Pieces of time-series data of Z(a, c) obtained by executing (Equation 14) for each time is referred to as pieces of color-converted and spatial-corrected data in the present disclosure.

The elements of the matrix X may be values obtained by subtracting background light intensities from raw light intensities in advance, or may be values obtained by applying appropriate noise reduction processing to raw light intensities. Similarly, the elements of the matrix Y may be values obtained by subtracting background light intensities from raw light intensities in advance, or may be appropriately changed.

In the case of the monochromatic detection of B=1 and C=1, the above description is simplified as follows. For each of the light-emitting points P(a) (a=1, 2, . . . , and A), the fluorescence emission of one type of fluorophore is detected in one detection region. It is assumed that the concentration of the fluorophore at the light-emitting points P(a) at any time is Z(a), and the signal intensity for the light-emitting points P(a') at any time is X(a'). Here, assuming that X is a matrix of A rows and 1 column with X(a') as elements, Z is a matrix of A rows and 1 column with Z(a) as elements, and Y is a matrix of A rows and A columns with Y(a')(a) as elements, (Equation 10) to (Equation 12) are simplified as the following equations. (Equation 9) and (Equation 14) are established with no change.

[Equation 15]

$$X = \begin{pmatrix} X(1) \\ \vdots \\ X(A) \end{pmatrix} \quad \text{(Equation 15)}$$

-continued

[Equation 16]

$$Y = \begin{pmatrix} Y(1)(1) & \dots & Y(1)(A) \\ \vdots & \ddots & \vdots \\ Y(A)(1) & \dots & Y(A)(A) \end{pmatrix} \quad \text{(Equation 16)}$$

[Equation 17]

$$Z = \begin{pmatrix} Z(1) \\ \vdots \\ Z(A) \end{pmatrix} \quad \text{(Equation 17)}$$

(Equation 9) and (Equation 14) to (Equation 17) are superficially the same as the general formulas used in PTL 3, for example, [[Equation 7]] to [[Equation 9]] of PTL 3, but the contents are greatly different (hereinafter, the equations used in PTL 3 are described with [[ ]]). Each element αij of the matrix A in [[Equation 7]] is a function of a distance dij between detection regions for light-emitting points φ(meas)i and φ(meas)j, and specifically is represented by the sum of exponential functions of dij as illustrated in [[Equation 10]]. αij attenuates as dij increases. In PTL 3, different fluorescence images are obtained for different samples, and positions of the detection regions for the plurality of light-emitting points randomly change in the fluorescence images. Thus, in PTL 3, the function is obtained in advance. For all the combinations of the two light-emitting points among the plurality of light-emitting points in each fluorescence image, all distances between the detection regions for any two light-emitting points are obtained, and are substituted into the function to derive αij. Accordingly, αij, that is, the matrix A changes for each sample or each fluorescence image. On the contrary, the present disclosure has found that each element Y(a')(a) of the matrix Y of (Equation 16) cannot be expressed by a function of the distance between the detection regions for the light-emitting points P(a) and P(a') as described above or as will be described later in [Description of Embodiments]. It was found that it is also impossible to obtain the elements Y(a')(a) by calculation from the configuration of the optical system and the like. Thus, in the present disclosure, under the condition that the positions of the detection regions for the plurality of light-emitting points do not change even for different samples, the elements Y(a')(a) are obtained by actual measurement. Specifically, as described above, one column $Y(a')(a_0)$ (a'=1, 2, . . . , and A) of the matrix Y is determined by causing fluorescence emission alone only at any one light-emitting point $P(a_0)$. All the columns of the matrix Y are determined by sequentially performing the above steps for all the A light-emitting points P(a). The matrix Y is determined only by the characteristics of the light-emitting points P(a), and does not change during the analysis. As long as conditions such as the optical system, the light-emitting points P(a), and the detection regions thereof are fixed, the matrix Y is kept constant even for analyses of different samples. It is impossible to perform the above steps with the optical system or device configuration of PTL 3. This is because, the positions of the detection regions for the plurality of light-emitting points cannot be fixed, and it is impossible to cause light emission alone and sequentially only from each of the light-emitting points even though the positions can be fixed. Accordingly, the method of the present disclosure cannot be conceived from PTL 3.

The above description can be replaced as follows. That is, for each of A light-emitting points (A is an integer of 2 or more), light emissions of C types (C is an integer of 1 or more) of light emitters are detected in detection regions of B wavelength bands (B is an integer of 1 or more). The light emissions of the light emitters D(a, c) (c=1, 2, . . . , and C) present at the light-emitting points P(a) (a=1, 2, . . . , and A) are detected in the detection regions W(a, b) (b=1, 2, . . . , and B) of different wavelength bands. It is assumed that the concentrations of the light emitters D(a, c) at the light-emitting points P(a) at any time are Z(a, c) and the light-emission intensities of W(a', b) for the light-emitting points P(a') are X(a', b). Also in this case, (Equation 9) to (Equation 17) are established, and similarly, both the spectral crosstalk and the spatial crosstalk can be eliminated to obtain the concentrations Z(a, c) of the A×C light emitters. Here, the light emissions include fluorescence, phosphorescence, scattering light, or the like.

The above description may be replaced as follows. That is, light absorptions of C types (C is an integer of 1 or more) of light absorbers are detected in detection regions of B wavelength bands (B is an integer of 1 or more) for each of A light-absorbing points (A is an integer of 2 or more). The light absorptions of the light absorbers D(a, c) (c=1, 2, . . . , and C) present at the light-absorbing points P(a) (a=1, 2, . . . , and A) are detected in the detection regions W(a, b) (b=1, 2, . . . , and B) of different wavelength bands. It is assumed that the concentrations of the light absorbers D(a, c) at the light-absorbing points P(a) at any time are Z(a, c) and the absorbances of W(a', b) for the light-absorbing points P(a') are X(a', b). Also in this case, (Equation 9) to (Equation 17) are established, and similarly, both the spectral crosstalk and the spatial crosstalk can be eliminated to obtain the concentrations Z(a, c) of the A×C light absorbers.

Alternatively, the above description can be replaced with multi-point detection other than light measurement. That is, signals of C types (C is an integer of 1 or more) of signal generators are detected in detection regions of B frequency bands (B is an integer of 1 or more) for each of A signal generation points (A is an integer of 2 or more). The signals of the signal generators D(a, c) (c=1, 2, . . . , and C) present at the signal generation points P(a) (a=1, 2, . . . , and A) are detected in the detection regions W(a, b) (b=1, 2, . . . , and B) of different frequency bands. It is assumed that the densities of the signal generators D(a, c) at the signal generation points P(a) at any time are Z(a, c). Further, it is assumed that the signal intensities of W(a', b) for the signal generation points P(a') are X(a', b). Also in this case, (Equation 9) to (Equation 17) are established, and similarly, both the spectral crosstalk and the spatial crosstalk can be eliminated to obtain the densities Z(a, c) of the A×C signal generators.

As described above, the description using the equations has been given. Such description is for facilitating understanding of the contents of the present disclosure. When the technology of the present disclosure is implemented, a method based on the contents of the present disclosure may be used. The method do not have to follow the equations completely. The equations may be modified or may not be used. In the present disclosure, the description of "the concentration of the light emitter" can be replaced with "the light-emission intensity of the light emitter", the description of "the concentration of the fluorophore" can be replaced with "the fluorescence intensity of the fluorophore", and the description of "the concentration of the light absorber" can be replaced with "the absorbance of the light absorber".

Further features related to the present disclosure will be apparent from the description of the present specification and the accompanying drawings. Aspects of the present disclosure are achieved and realized by elements, combinations of various elements, and aspects of the following detailed description and appended claims.

The description of the present specification is merely an example, and does not limit the scope of claims or application examples of the present disclosure in any sense.

Further features related to the present disclosure will be apparent from the description of the present specification and the accompanying drawings. Aspects of the present disclosure are achieved and realized by elements, combinations of various elements, and aspects of the following detailed description and appended claims.

The description of the present specification is merely an example, and does not limit the scope of claims or application examples of the present disclosure in any sense.

Advantageous Effects of Invention

According to the present disclosure, it is possible to identify and independently detect light emissions from a plurality of light-emitting points by eliminating or reducing the spatial crosstalk between the plurality of the light-emitting points by calculation processing. The crosstalk occurs in any optical system that detects the light emissions from the plurality of light-emitting points. It is also possible to identify and independently detect fluorescences of a plurality of types of fluorophores from a plurality of light-emitting points by eliminating or reducing the spatial crosstalk between the plurality of the light-emitting points and the spectral crosstalk between the plurality of types of the fluorophores for each light-emitting point by calculation processing. The spatial crosstalk and the spectral crosstalk occur in any optical system that detects the fluorescences of the plurality of types of the fluorophores emitted from the plurality of the light-emitting points.

Further, it is possible to avoid a decrease in detection sensitivity or a decrease in detection dynamic range caused by the spatial crosstalk and the spectral crosstalk, by eliminating or reducing the spatial crosstalk and the spectral crosstalk.

Other objects, configurations, and effects will be made apparent in the following descriptions.

DESCRIPTION OF EMBODIMENTS

First Embodiment

Figure 1:
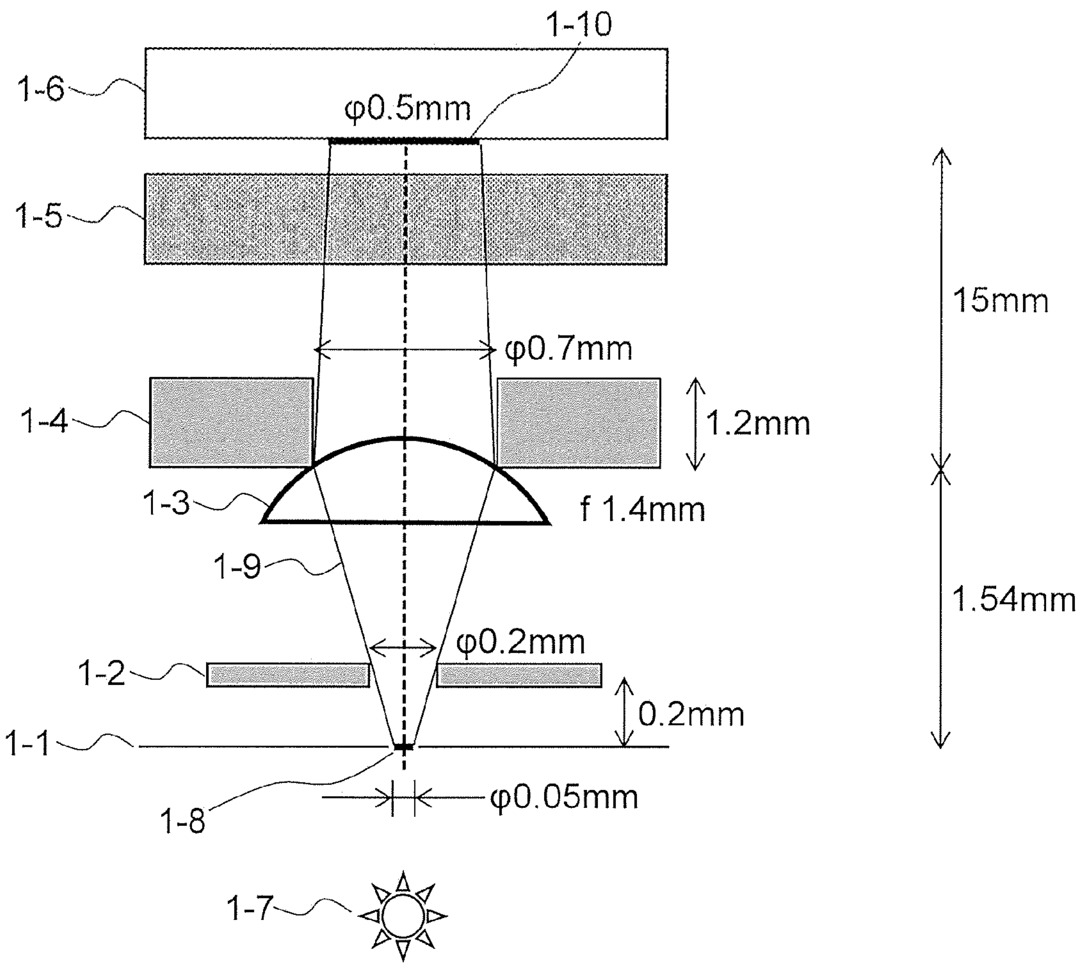
FIG. 1 is a schematic diagram of a simple optical system.

In order to investigate characteristics of spatial crosstalk in detail, a simple optical system illustrated in FIG. 1 was constructed. The optical system in FIG. 1 includes a pinhole plate 1-1, a light-emitting-point-side aperture plate 1-2, a condenser lens 1-3, a sensor-side aperture plate 1-4, a color glass filter 1-5, a two-dimensional sensor 1-6, and a halogen lamp (light source) that emits halogen lamp light 1-7. Specifically, the optical system of FIG. 1 was constructed as follows. A light-emitting point 1-8 of φ 0.05 mm was formed by irradiating the pinhole plate 1-1 having a pinhole of φ 0.05 mm from below with the halogen lamp light 1-7. The light-emitting-point-side aperture plate 1-2 having an aperture of φ 0.2 mm was disposed at a position 0.2 mm above the light-emitting point 1-8. The condenser lens 1-3 having a focal length f=1.4 mm was disposed at a position 1.54 mm above the light-emitting point 1-8. The sensor-side aperture plate 1-4 having an aperture of φ 0.7 mm was disposed immediately above the condenser lens 1-3. The two-dimensional sensor 1-6 was disposed at a position 15 mm above the condenser lens 1-3. The color glass filter 1-5 was disposed immediately below the two-dimensional sensor 1-6. In addition, the pinhole plate 1-1, the light-emitting-point-side aperture plate 1-2, the sensor-side aperture plate 1-4, the color glass filter 1-5, and the two-dimensional sensor 1-6 were disposed in parallel to each other. Light 1-9 emitted from the light-emitting point 1-8 was transmitted through the aperture of φ 0.2 mm, was condensed by the condenser lens 1-3, was transmitted through the aperture of φ 0.7 mm, and was transmitted through the color glass filter 1-5, and then a light emission image 1-10 of φ 0.5 mm was formed on the two-dimensional sensor 1-6. Here, the light-emitting point 1-8 was imaged on the two-dimensional sensor 1-6 in focus at a magnification of 10 times.

Figure 2A:
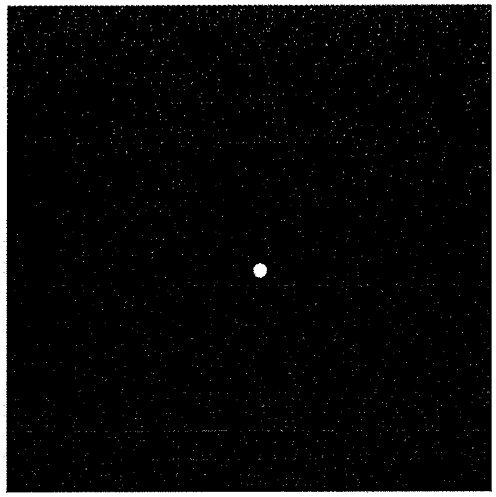
FIGS. 2A-2B is light-emitting images acquired by a two-dimensional sensor of the simple optical system.
Figure 2B:
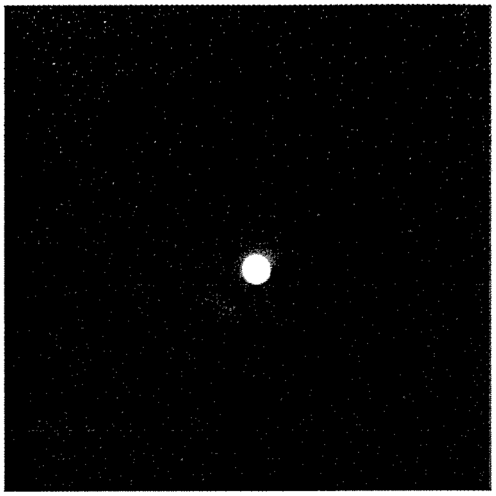

FIGS. 2A to 2B show sensor images including the light-emission images 1-10 acquired by the two-dimensional sensor 1-6 in the simple optical system of FIG. 1. A sensor size of the two-dimensional sensor 1-6 is 13×13 mm, and a signal range of each pixel is 0 to 65536. FIGS. 2A and 2B are the same light-emission image, but a signal display scale (gray scale) of FIG. 2A is set to 0 to 50000, and a signal display scale of FIG. 2B is set to 0 to 500. The maximum signal intensity of the light-emission image is about 50000. Signals of all pixels are displayed with almost no saturation in FIG. 2A, whereas the light-emission image is displayed with saturation in FIG. 2B. Referring to FIG. 2A, the light-emission image of φ 0.5 mm is obtained as expected, and signal intensity outside the light-emission image of φ 0.5 mm appears to be 0. However, referring to FIG. 2B, it can be confirmed that a skirt with low signal intensity extends outside the light-emission image of ϕ 0.5 mm.

Figures 3A, 3B, 3C:
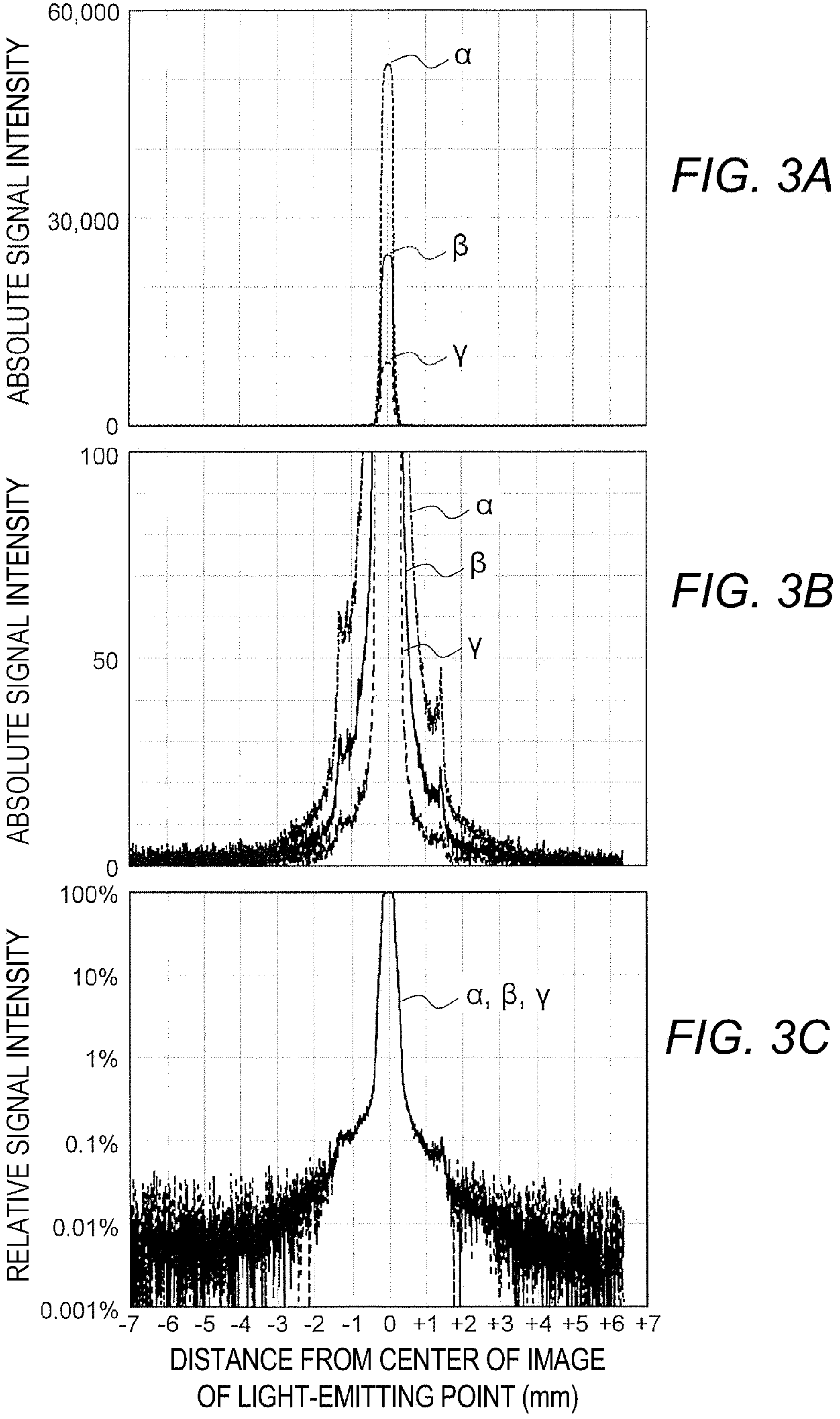
FIGS. 3A-3C illustrates signal intensity distributions of the light emission images in the sensor images.

Each α (dotted line) in FIGS. 3A to 3C indicates a signal intensity distribution in a horizontal direction passing through a center of the light-emission image in the sensor image of FIGS. 2A to 2B. FIGS. 3A, 3B, and 3C use the same data, but vertical axes are changed. Horizontal axes are common and indicate distances from the center of the light-emission image. Plus and minus signs on each horizontal axis indicate a right side and a left side of the light-emission image, respectively, in each sensor image. In each of FIGS. 3A and 3B, the vertical axis represents an absolute signal intensity. The vertical axis scale is set to 0 to 60000 in FIG. 3A. The vertical axis scale is set to 0 to 100 in FIG. 3B. On the other hand, in FIG. 3C, the vertical axis indicates relative signal intensity to the maximum signal intensity. The vertical axis scale is the log scale and set to 0.001% to 100% with the maximum signal intensity as 100%. Each β (solid line) and each γ (broken line) in FIGS. 3A to 3C indicate signal intensity distributions similarly to α when an output intensity of the halogen lamp light 1-7 is decreased in a stepwise manner under the same conditions as those for acquiring the light-emission images in FIGS. 2A to 2B. As can be seen from FIG. 3A, the maximum signal intensities of the light-emission images of a, β, and γ are about 50000, about 25000, and about 10000, respectively. As can be seen from FIG. 3B, the signal intensity decreases as the distance from the center of the light-emission image increases, but a skirt that is much wider than a size (about 0.5 mm in width) of the light-emission image seen in FIG. 3A lies. It can also be seen that as the maximum signal intensity decreases the intensity of the skirt also decreases. However, it can be seen from FIG. 3C that α, β, and γ are completely overlapped each other to form one line. This is a new discovery and brings several important findings. For example, a signal intensity of about 0.1% of the maximum signal intensity is observed at positions ±1 mm away from the center of the light-emission image, that is, at positions outside the light-emission image seen in FIG. 2A. A case where there is a detection region for an adjacent light-emission image at a position ±1 mm away means that there is about 0.1% spatial crosstalk. It is surprising that there is the spatial crosstalk of such a non-negligible magnitude in spite of just focusing the light-emitting point by using an extremely simplified optical system illustrated in FIG. 1. More surprisingly, since α, β, and γ are completely overlapped each other, as long as the optical system and the positions of the light-emitting points are fixed, it was found that a relative signal intensity distribution of a light-emission image is constant regardless of a light-emission intensity of the light-emitting point or a signal intensity of the light-emission image.

Figure 4A:
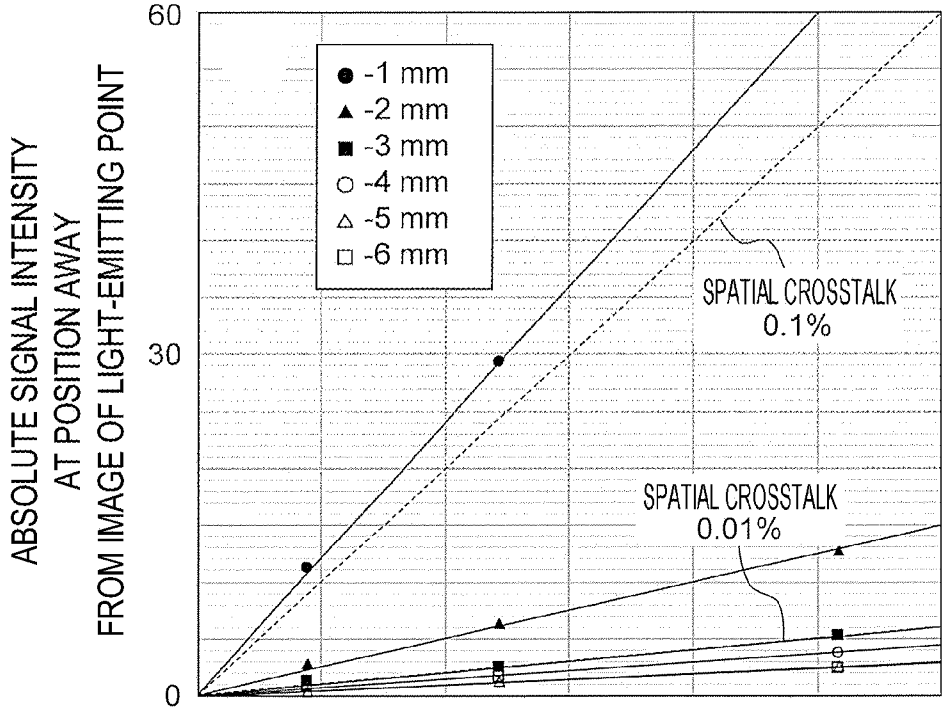
FIGS. 4A-4B illustrates relationships between absolute signal intensities at centers of images of the light-emitting point and absolute signal intensities at positions away from the centers of the images of the light-emitting point to the left.
Figure 5A:
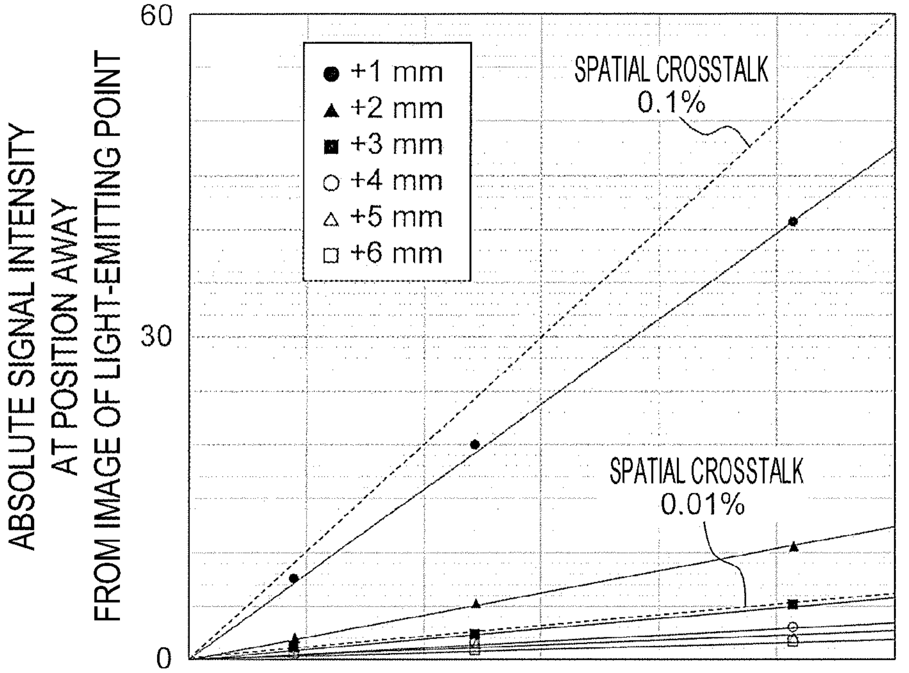
FIGS. 5A-5B illustrates relationships between absolute signal intensities at centers of images of the light-emitting point and absolute signal intensities at positions away from the centers of the images of the light-emitting point to the right.

FIGS. 4A and 5A show results derived from FIGS. 3A to 3C. FIG. 4A is a graph with absolute signal intensity at the center of the light-emission image on a horizontal axis and absolute signal intensity at positions −1, −2, −3, −4, −5, and −6 mm away from the center of the light-emission image on a vertical axis. FIG. 5A is a graph with absolute signal intensity at the center of the light-emission image on a horizontal axis and absolute signal intensity at positions +1, +2, +3, +4, +5, and +6 mm away from the center of the light-emission image on a vertical axis. Each of the absolute signal intensity was an average value of absolute signal intensities within ±0.1 mm around each position in FIGS. 3A to 3C. As a result, it was found that all three plots (corresponding to α, β, and γ in FIGS. 3A to 3C) at each position were respectively on an approximate straight line passing through an origin. A slope of each approximate straight line indicates a spatial crosstalk ratio at the corresponding position. That is, it can be seen that the slope of the approximate straight line decreases and then the spatial crosstalk ratio decreases as the distance from the center of the light-emission image increases. For comparison, a straight line with spatial crosstalk of 0.1% and a straight line with spatial crosstalk of 0.01% are superimposed and displayed by dotted lines. For example, it can be read that a spatial crosstalk ratio at a position −1 mm away from the center of the light-emission image is a little over 0.18, whereas a spatial crosstalk ratio at a position −3 mm away is about 0.01%. The above results indicate that the absolute signal intensity of the spatial crosstalk at any position away from the center of the light-emission image has a linear relationship with the absolute signal intensity at the center of the light-emission image. That is, the spatial crosstalk ratio is constant regardless of the absolute signal intensity at the center of the light-emission image. Furthermore, it has been newly found that it is possible to eliminate or decrease the spatial crosstalk at any position away from the center of the light-emission image by subtracting a value obtained by multiplying the absolute signal intensity at the center of the light-emission image by the spatial crosstalk ratio at the position from the absolute signal intensity at the position. This corresponds to subtracting the value of the corresponding approximate straight line at the same position from the absolute signal intensity of each plot in FIGS. 4A and 5A.

Figure 4B:
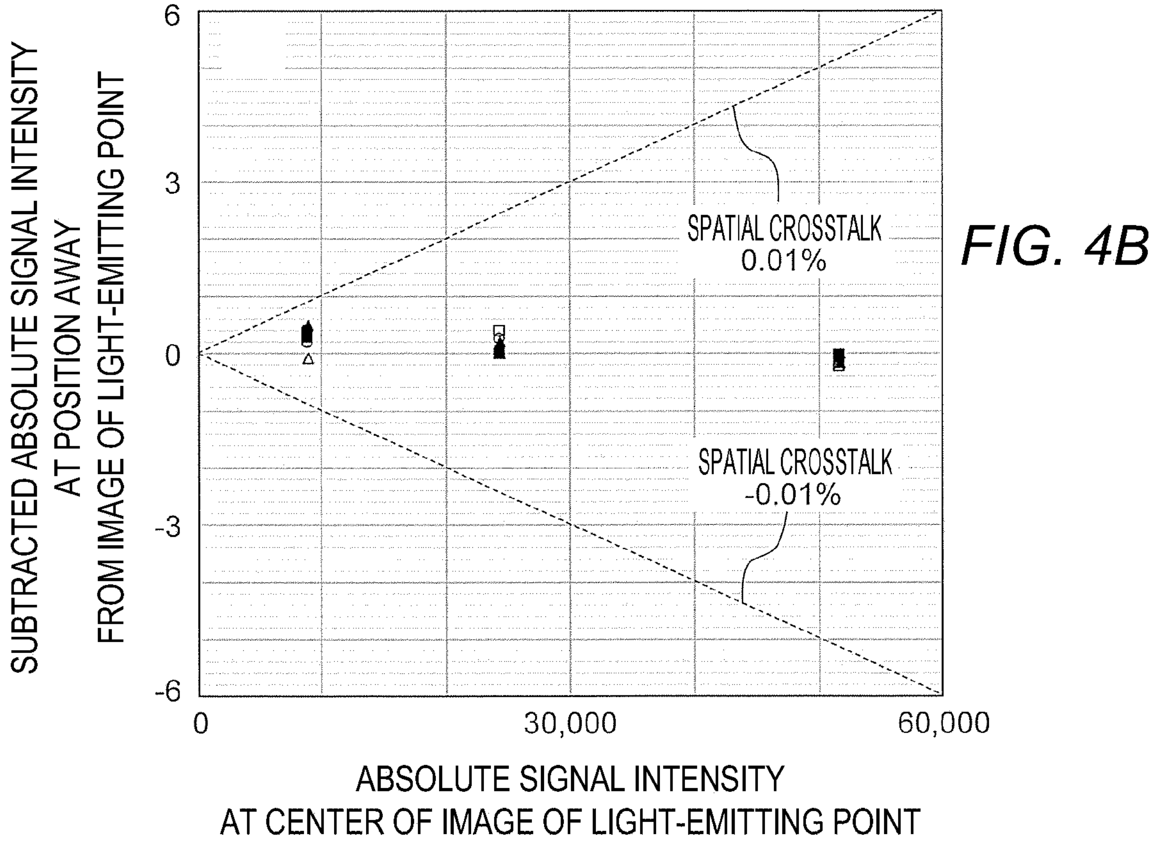
Figure 5B:
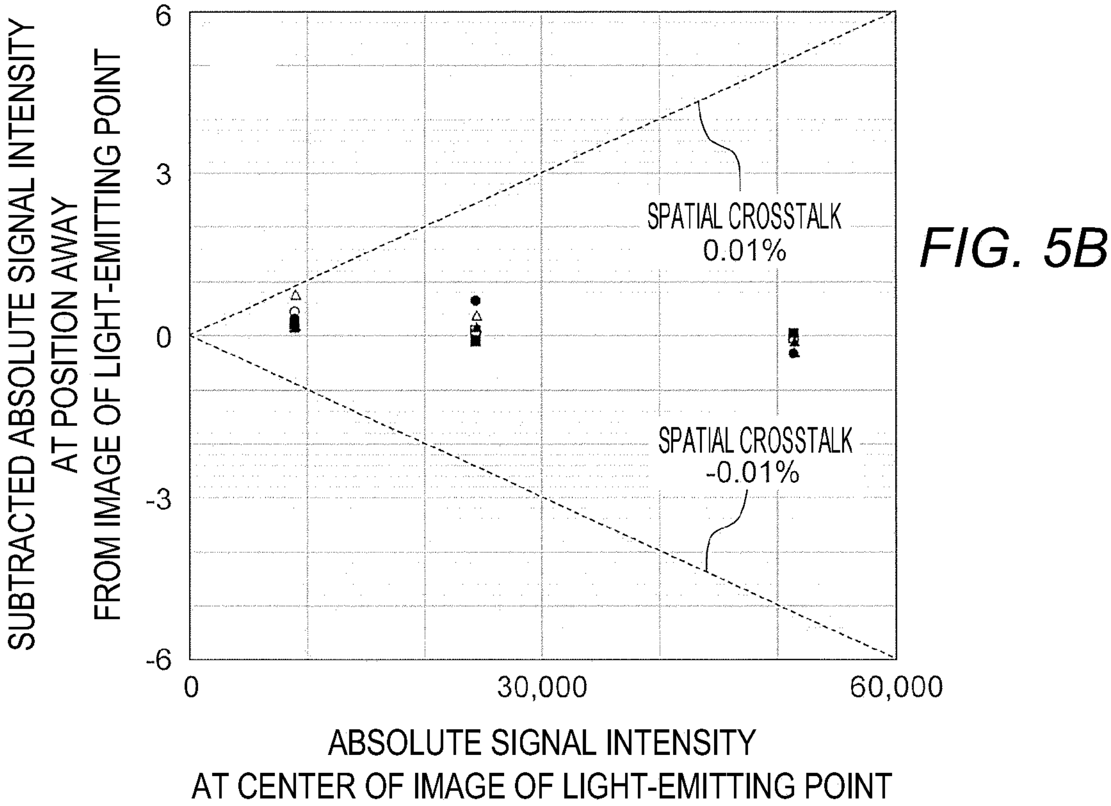
Figure 6A:
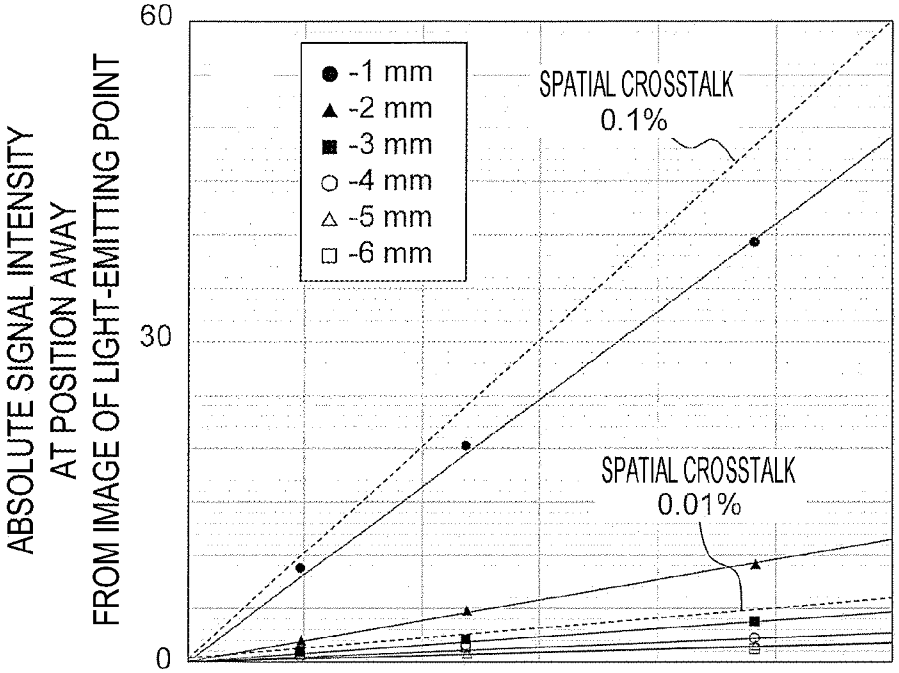
FIGS. 6A-6B illustrates relationships between absolute signal intensities at centers of images of the light-emitting point and absolute signal intensities at positions away from the centers of the images of the light-emitting point to the left.
Figure 6B:
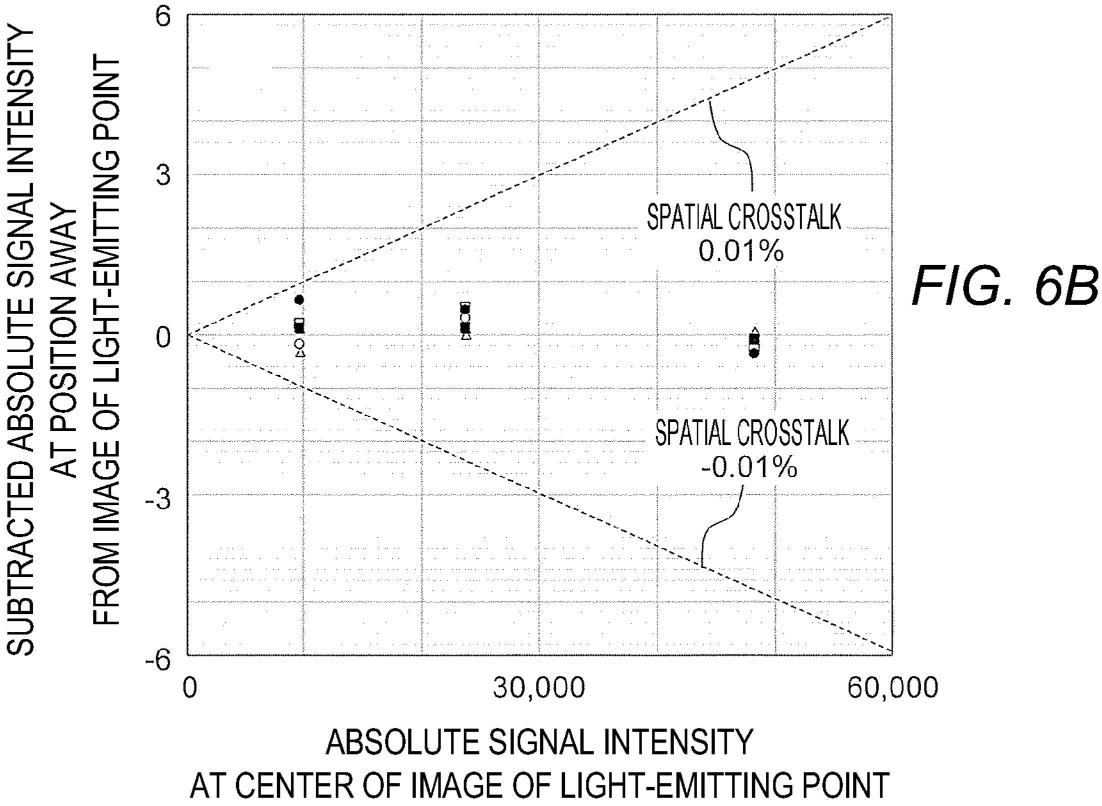

FIGS. 4B and 5B illustrate results obtained by performing the above-described subtraction on the results of FIGS. 4A and 5A, respectively. The types of the plots indicating different positions and the horizontal axis are common in FIGS. 4A and 4B and FIGS. 5A and 5B. The vertical axis in FIGS. 4B and 5B indicates the absolute signal intensity after the subtraction is performed, and the vertical axis scale is enlarged as compared with FIGS. 4A and 5A. For comparison, straight lines having spatial crosstalk of ±0.01% is superimposed and displayed by dotted lines in FIGS. 4B and 5B. As a result, it was found that the absolute signal intensities after the subtraction at each position were almost zero regardless of the absolute signal intensities of the center of the light-emission image. That is, the spatial crosstalk at each position was reduced within ±0.01%. As for the position −1 mm away from the center of the light-emission image, the spatial crosstalk was reduced by at least one digit or more by this method. The reason why the absolute signal intensities after the subtraction at each position are not completely zero is that there is a deviation or an error between each plot and the corresponding approximate straight line in FIGS. 4A and 5A. As a decision coefficient ($R^2$) of each approximate straight line passing through the origin at each position is higher (closer to 1), that is, as the linearity of the absolute signal intensity at each position with respect to the absolute signal intensity at the center of the light-emission image is higher, the aforementioned error is smaller, and the absolute signal intensity after the subtraction is closer to zero. Of course, the absolute signal intensity after the subtraction may be negative. However, as long as there is the above linearity, the magnitude of the absolute signal intensity at each position decreases at least by the subtraction. As the slope of the approximate straight line is smaller, that is, as the spatial crosstalk before the subtraction is smaller, since an absolute value of a difference between the absolute signal intensity at each position and the corresponding approximate straight line is also smaller, the above error is also smaller.

FIGS. 6A to 6B and 7A to 7B illustrate experimental results similar to FIGS. 4A to 4B and 5A to 5B. In the optical system of FIG. 1, after the pinhole plate 1-1 was once detached and was attached again, the similar results as those of FIGS. 2A to 2B and 3A to 3C were acquired. Then, the results of FIGS. 6A to 6B and 7A to 7B were derived by the same method as in FIGS. 4A to 4B and 5A to 5B. The attachment position of the pinhole plate 1-1 is substantially the same as the original position, but is not exactly the same position strictly. The results of FIGS. 6A to 6B and 7A to 7B were equivalent to the results of FIGS. 4A to 4B and 5A to 5B. Those results indicated that the reproducibility of the method for eliminating or decreasing the spatial crosstalk at any position by the subtraction processing is high.

Figures 7A, 7B:
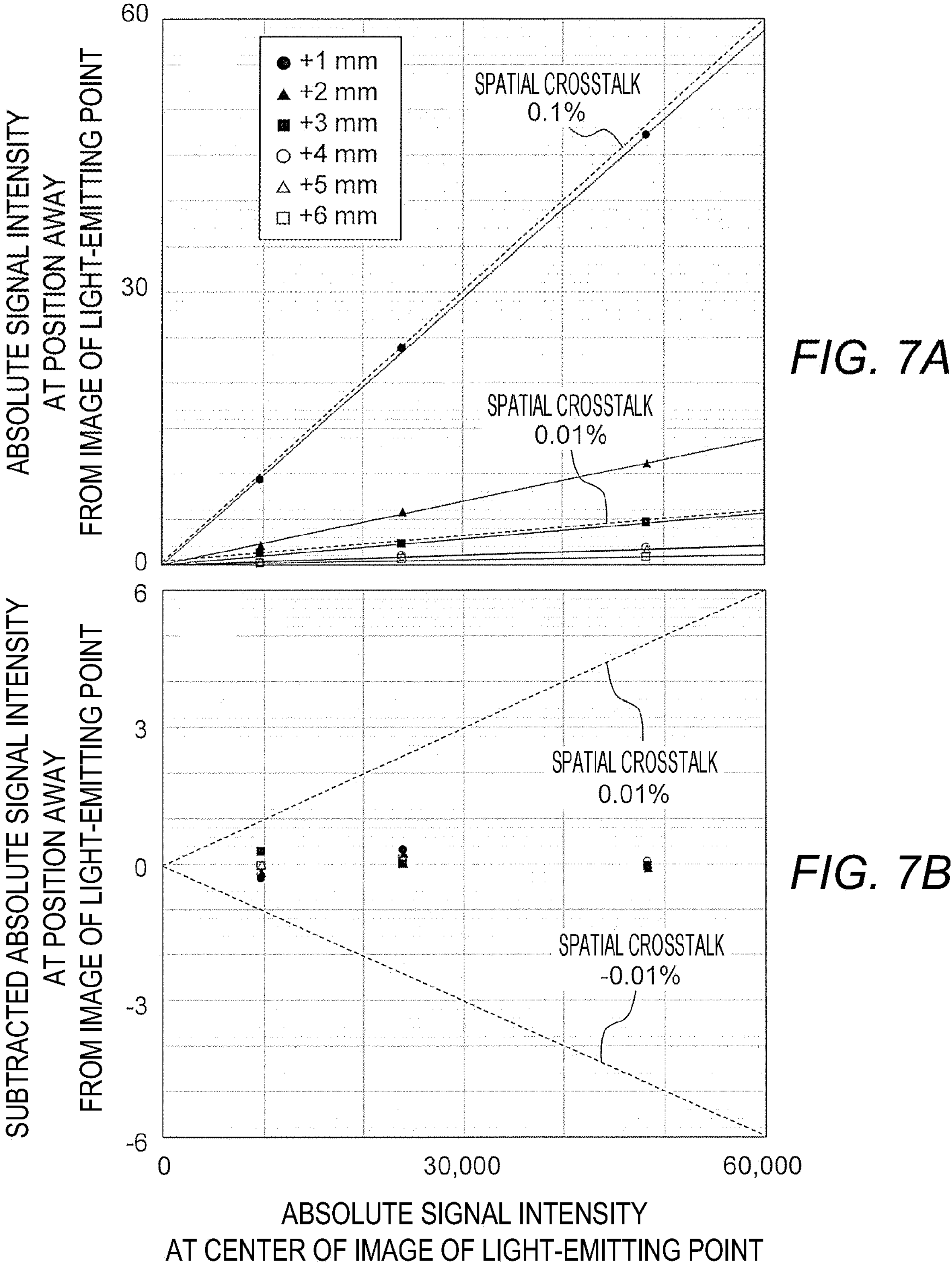
FIGS. 7A-7B illustrates relationships between absolute signal intensities at centers of images of the light-emitting point and absolute signal intensities at positions away from the centers of the images of the light-emitting point to the right.

On the other hand, from the comparison of FIGS. 4A to 4B to 7A to 7B, another important finding was obtained as follows. The approximate straight lines of −1 mm in FIG. 4A, +1 mm in FIG. 5A, −1 mm in FIG. 6A, and +1 mm in FIG. 7A are compared. It was found that all slopes of these four approximate straight lines indicate spatial crosstalk ratios at the positions 1 mm away from the center of the light-emission image but were different from each other. Accordingly, for example, when the subtraction processing of each plot for +1 mm in FIG. 5A, −1 mm in FIG. 6A, or +1 mm in FIG. 7A was performed by using the approximate straight line for −1 mm in FIG. 4A, it was apparent that the above error increases and the reduction of the spatial crosstalk becomes insufficient. This phenomenon similarly occurs at other positions. It was found that such improper subtraction processing may cause an inverse effect, that is, it may increase spatial crosstalk in some cases. It is conceivable that such a phenomenon occurs since (1) even in the simple optical system as illustrated in FIG. 1, point symmetry of the spatial crosstalk caused by imaging is not necessarily high (for example, in FIGS. 2A to 2B, the spatial crosstalk ratios are different on the left and right sides of the light-emission image), and (2) the spatial crosstalk caused by imaging significantly changes with a subtle change in the optical system such as a slight shift in the position of the light-emitting point. Accordingly, it was found that it is impossible to express ratio of the spatial crosstalk from the center of the light-emission image to any position by a function of a distance therebetween. This means that the method disclosed in PTL 3 does not function effectively. The present disclosure is different from PTL 3 in that each mutual spatial crosstalk ratio is derived by experiments independently of each mutual distance as illustrated in each of FIGS. 4A to 4B to 7A to 7B under conditions that an optical system and a plurality of light-emission images, that is, a plurality of detection regions are fixed. When the conditions are changed, it is necessary to re-acquire each spatial crosstalk ratio each time.

When the knowledge obtained in the above experiments is extended and generalized, or, when the fact that the absolute signal intensity of the spatial crosstalk at any position away from the center of the light-emission image has linearity with respect to the absolute signal intensity at the center of the light-emission image and the fact that the spatial crosstalk ratio between them is constant is extended and generalized, (Equation 9) to (Equation 17) are derived.

Second Embodiment

Model experiments by the simplest optical system that detects fluorescences of a plurality of types of fluorophores emitted from a plurality of light-emitting points in a plurality of detection regions with different wavelength bands were conducted. In the present embodiment and other embodiments using the same model experimental system, in (Equation 9) to (Equation 12), fluorescence emissions of C=2 types of fluorophores are detected for A=2 light-emitting points in B=2 detection regions with different wavelength bands as an example. It goes without saying that the same effect is obtained by the same method even when A, B, and C have another numerical values.

Figure 8:
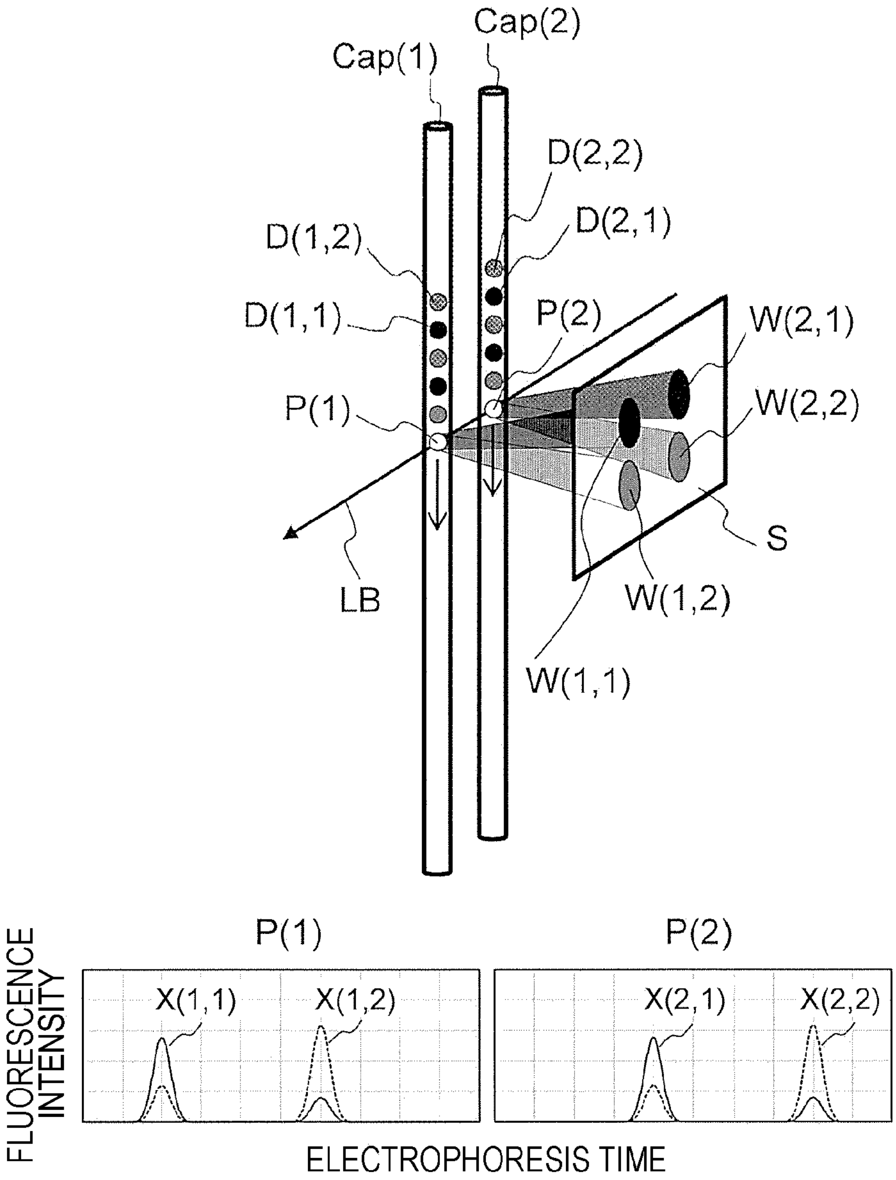
FIG. 8 is a schematic diagram of a model experimental system.

FIG. 8 illustrates a model experimental system. The model experimental system of FIG. 8 includes two capillaries Cap(1) and Cap(2), and a light source (not illustrated) that emits a laser beam LB along an arrangement direction of the two capillaries Cap(1) and Cap(2). Light-emitting points P(1) and P(2) are provided on the two capillaries Cap(1) and Cap(2), respectively, at positions irradiated with the laser beam LB. Components labeled with two types of fluorophores D(1, 1) and D(1, 2) are electrophoresed in the capillary Cap(1). Components labeled with two types of fluorophores D(2, 1) and D(2, 2) are electrophoresed in the capillary Cap(2). Here, D(1, 1) and D(2, 1) are the same type of fluorophore, and D(1, 2) and D(2, 2) are the same type of fluorophore. Fluorophores of the same type emit fluorescences with the same fluorescence spectrum. The fluorophores D(1, 1) and D(1, 2) emit fluorescences at the light-emitting point P(1) by irradiation with the laser beam LB, and the fluorescences are detected in detection regions W(1, 1) and W(1, 2) provided in a sensor S. Wavelength bands of the detection regions W(1, 1) and W(1, 2) are designed to mainly detect the fluorescence emissions of the fluorophores D(1, 1) and D(1, 2), respectively. However, mutual spectral crosstalk is significantly present. Similarly, the fluorophores D(2, 1) and D(2, 2) emit fluorescences at the light-emitting point P(2) by irradiation with the laser beam LB, and the fluorescences are detected in detection regions W(2, 1) and W(2, 2) provided in the sensor S. Wavelength bands of the detection regions W(2, 1) and W(2, 2) are designed to mainly detect the fluorescence emissions of the fluorophores D(2, 1) and D(2, 2), respectively. However, mutual spectral crosstalk is significantly present. In addition, the fluorescence emissions of the fluorophores D(1, 1) and D(1, 2) at the light-emitting point P(1) are also detected in the detection regions W(2, 1) and W(2, 2). The fluorescence emissions of the fluorophores D(2, 1) and D(2, 2) at the light-emitting point P(2) are also detected in the detection regions W(1, 1) and W(1, 2). In other words, spatial crosstalk is significantly present. Assuming that signal intensities (fluorescence intensities) in the detection regions W(1, 1), W(1, 2), W(2, 1), and W(2, 2) are respectively X(1, 1), X(1, 2), X(2, 1), and X(2, 2), as illustrated in a lower side of FIG. 8, for the light-emitting points P(1), and P(2), pieces of time-series data of the signal intensities X(1, 1) and X(1, 2), and the signal intensities X(2, 1) and X(2, 2) are obtained with electrophoresis, respectively.

Note that, FIG. 8 illustrates that the detection regions W(1, 1), W(1, 2), W(2, 1), and W(2, 2) are provided on one sensor S, but the present disclosure is not limited thereto. The detection regions W(1, 1) and W(1, 2) may be provided on one sensor and the detection regions W(2, 1) and W(2, 2) may be provided on another sensor. Alternatively, the detection regions W(1, 1), W(1, 2), W(2, 1), and W(2, 2) may be provided on four different sensors. An image forming means and a spectroscopic means are required between the light-emitting points P(1) and P(2) and the sensor S. However, in the present embodiment, any image forming means and any spectroscopic means can be used. Therefore, the image forming means and the spectroscopic means are omitted in FIG. 8.

Figure 9A:
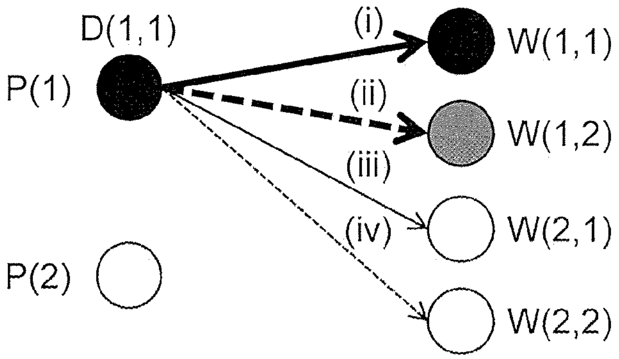
FIGS. 9A-9D is a schematic diagram of spectral crosstalk and spatial crosstalk in the model experimental system.
Figure 9B:
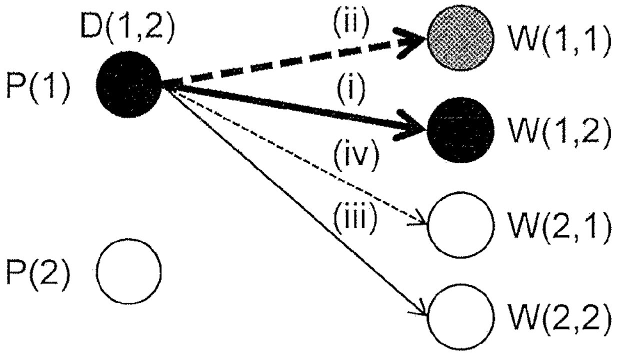
Figure 9C:
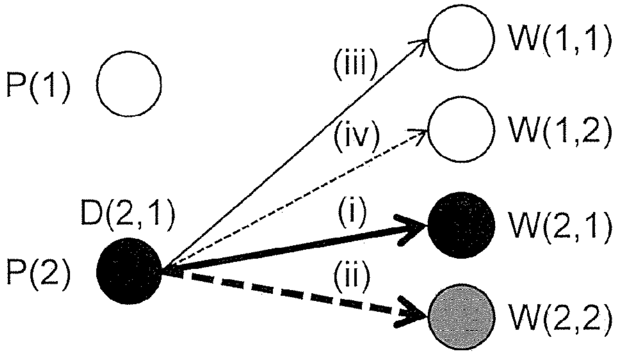
Figure 9D:
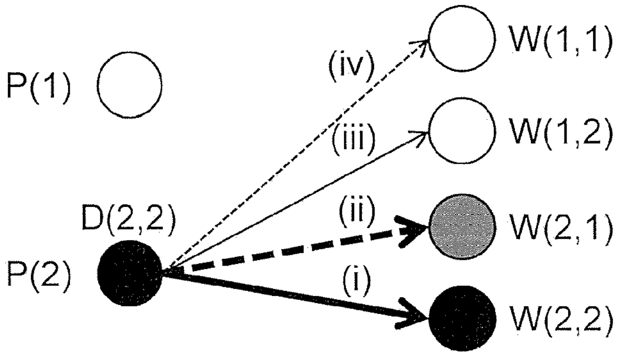

FIGS. 9A to 9D is a schematic diagram illustrating a relationship between spectral crosstalk and spatial crosstalk in FIG. 8. In FIG. 9A, the fluorescence emission of the fluorophore D(1, 1) at the light-emitting point P(1) is (i) mainly detected in the detection region W(1, 1) and (ii) subsidiary detected in the detection region W(1, 2). The fluorescence emission of the fluorophore D(1, 1) is also (iii) detected in the detection region W(2, 1) with a much smaller intensity than in (i) and (ii), and (iv) detected in the detection region W(2, 2) with a smaller intensity than in (iii). (i) and (ii) show spectral crosstalk, and (iii) and (iv) show spatial crosstalk and spectral crosstalk. That is, only (i) and (ii) are considered in the method of the related art, but all of (i) to (iv) are considered in the present disclosure. In FIGS. 9A to 9D, the above relationship between the intensities detected in the detection regions and the above relationship between the spectral crosstalk and the spatial crosstalk are commonly indicated by thickness and line type (solid line or dotted line) of the arrows and the numbers of (i) to (iv). Similarly to FIG. 9A, the fluorescence emission of the fluorophore D(1, 2) at the light-emitting point P(1) is drawn in FIG. 9B, the fluorescence emission of the fluorophore D(2, 1) at the light-emitting point P(2) is drawn in FIG. 9C, and the fluorescence emission of the fluorophore D(2, 2) at the light-emitting point P(2) is drawn in FIG. 9D. In actual analysis, the states shown in FIGS. 9A to 9D simultaneously occur at the same time, and fluorescence intensities are different from each other.

Figure 10:
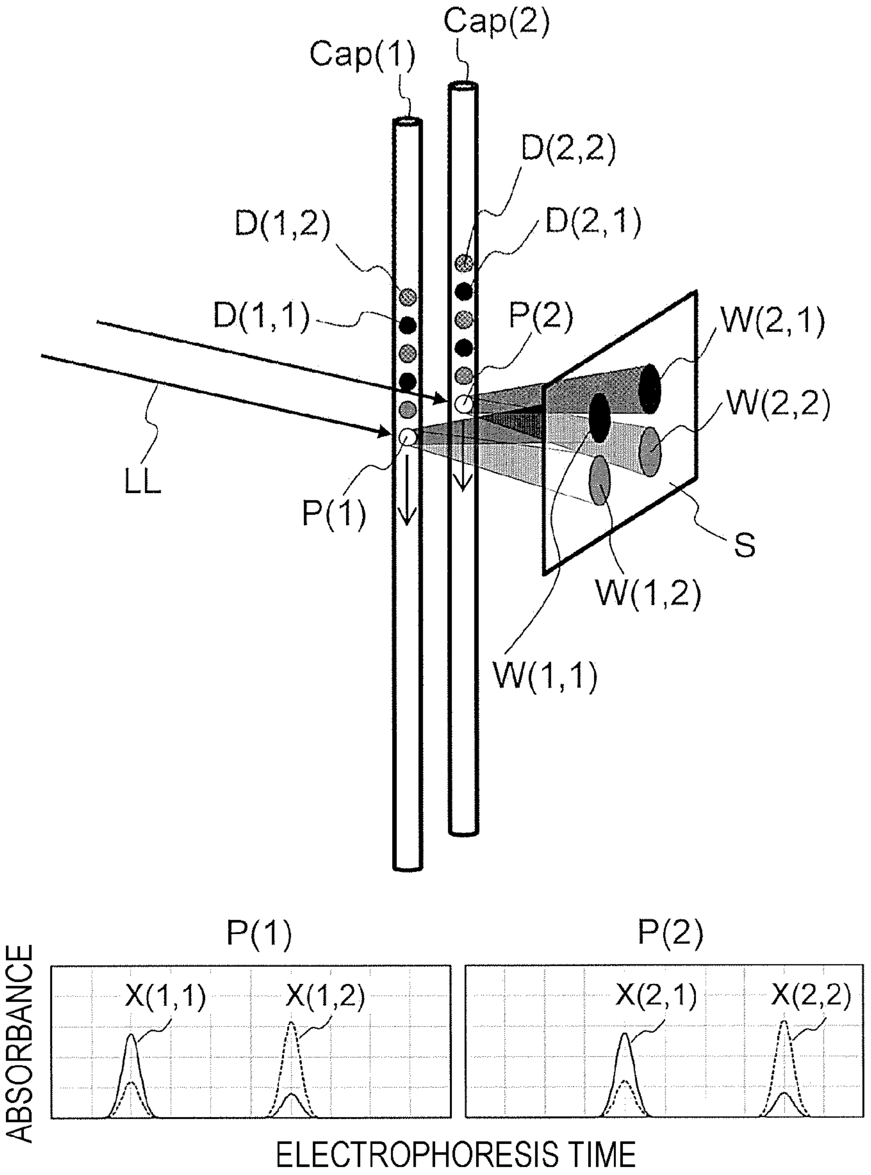
FIG. 10 is a schematic diagram of a model experimental system.

FIG. 10 illustrates a model experimental system similar to that in FIG. 8. However, in the model experimental system of FIG. 10, two capillaries Cap(1) and Cap(2) are irradiated with lamp lights LL from a light source perpendicularly to the arrangement direction thereof. Fluorescence emission by irradiation of a laser beam LB is not detected, but absorption or absorbance via transmission of the lamp light LL is detected. Light-absorbing points P(1) and P(2) are respectively provided on the two capillaries Cap(1) and Cap(2) at positions irradiated with the lamp light LL. Components with two types of light absorbers D(1, 1) and D(1, 2) are electrophoresed in the capillary Cap(1). Components with two types of light absorbers D(2, 1) and D(2, 2) are electrophoresed in the capillary Cap(2). Here, D(1, 1) and D(2, 1) are the same type of light absorber, and D(1, 2) and D(2, 2) are the same type of light absorber. Light absorbers of the same type absorb light with the same light absorption spectrum. The light absorbers D(1, 1) and D(1, 2) absorb lights at the light-absorbing point P(1) by irradiation with the lamp light LL, and lights that have not been absorbed are detected in detection regions W(1, 1) and W(1, 2) provided in a sensor S. Wavelength bands of the detection regions W(1, 1) and W(1, 2) are designed to mainly detect the absorbed lights of the light absorbers D(1, 1) and D(1, 2), respectively. However, mutual spectral crosstalk is significantly present. Similarly, the light absorbers D(2, 1) and D(2, 2) absorb lights at the light-absorbing point P(2) by irradiation with the lamp light LL. Lights that have not been absorbed are detected in detection regions W(2, 1) and W(2, 2) provided in the sensor S. Wavelength bands of the detection regions W(2, 1) and W(2, 2) are designed to mainly detect the absorbed lights of the light absorbers D(2, 1) and D(2, 2), respectively. However, mutual spectral crosstalk is significantly present. The absorptions of the light absorbers D(1, 1) and D(1, 2) at the light-absorbing point P(1) are also detected in the detection regions W(2, 1) and W(2, 2). Similarly, the absorptions of the light absorbers D(2, 1) and D(2, 2) at the light-absorbing point P(2) are also detected in the detection regions W(1, 1) and W(1, 2). That is, spatial crosstalk is significantly present. This is because parts of the transmitted light of the lamp light LL transmitted through the light-absorbing point P(1) are also detected in the detection regions W(2, 1) and W(2, 2). Further, that is because parts of the transmitted lights of the lamp light LL transmitted through the light-absorbing point P(2) are also detected in the detection regions W(1, 1) and W(1, 2). Assuming that the absorbances in the detection regions W(1, 1), W(1, 2), W(2, 1), and W(2, 2) are X(1, 1), X(1, 2), X(2, 1), and X(2, 2), respectively, as illustrated in a lower side of FIG. 10, pieces of time-series data of the absorbances X(1, 1) and X(1, 2) and the absorbances X(2, 1) and X(2, 2) are obtained with electrophoresis for the light-absorbing points P(1) and P(2). Hereinafter, a case where FIG. 8 is used will be described, but it goes without saying that the same effect is obtained in a case where FIG. 10 is used.

Figures 11A, 11B, 11C, 11D:
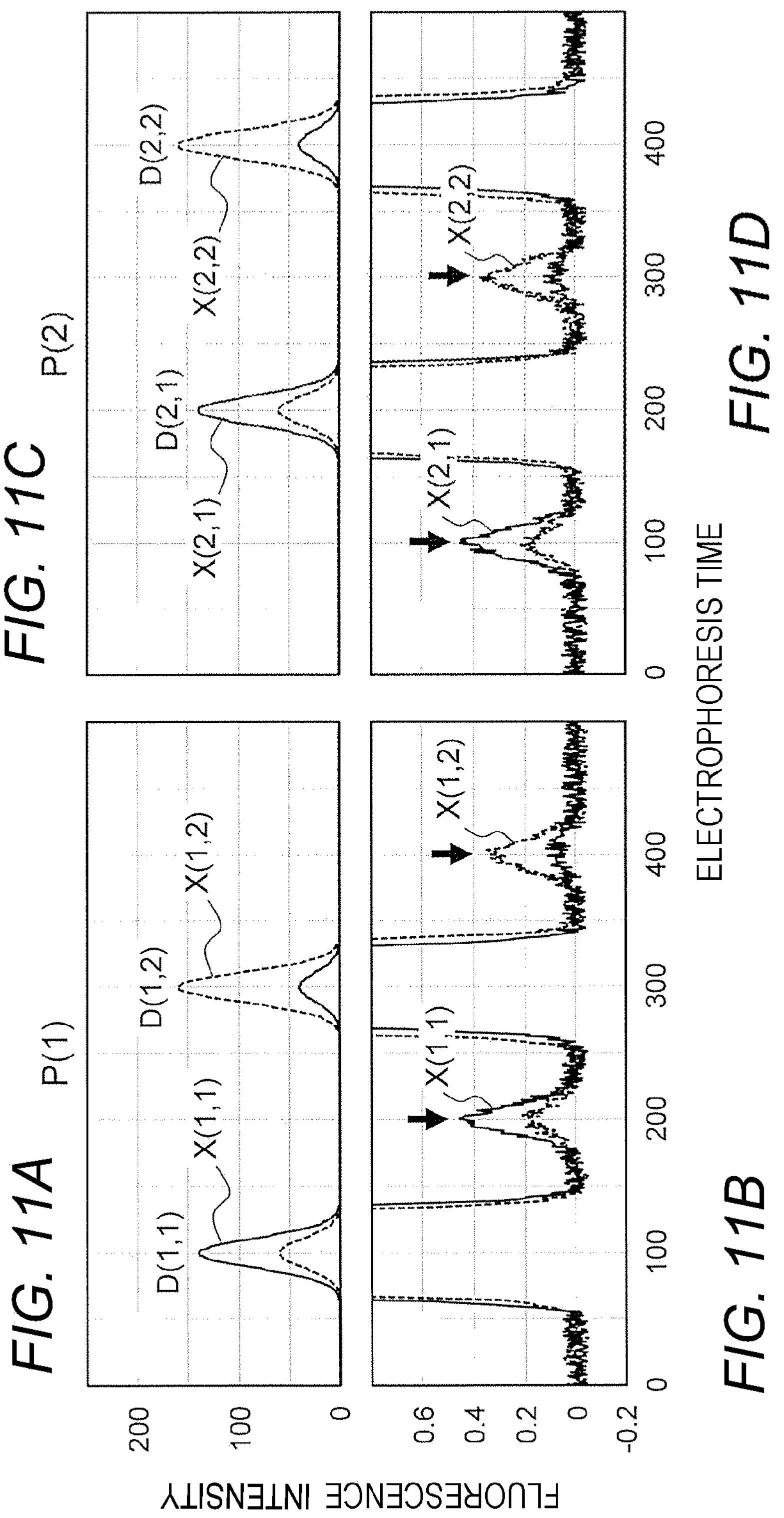
FIGS. 11A-11D illustrates raw data obtained by electrophoresis analyses of known samples.
Figures 12A, 12B, 12C, 12D:
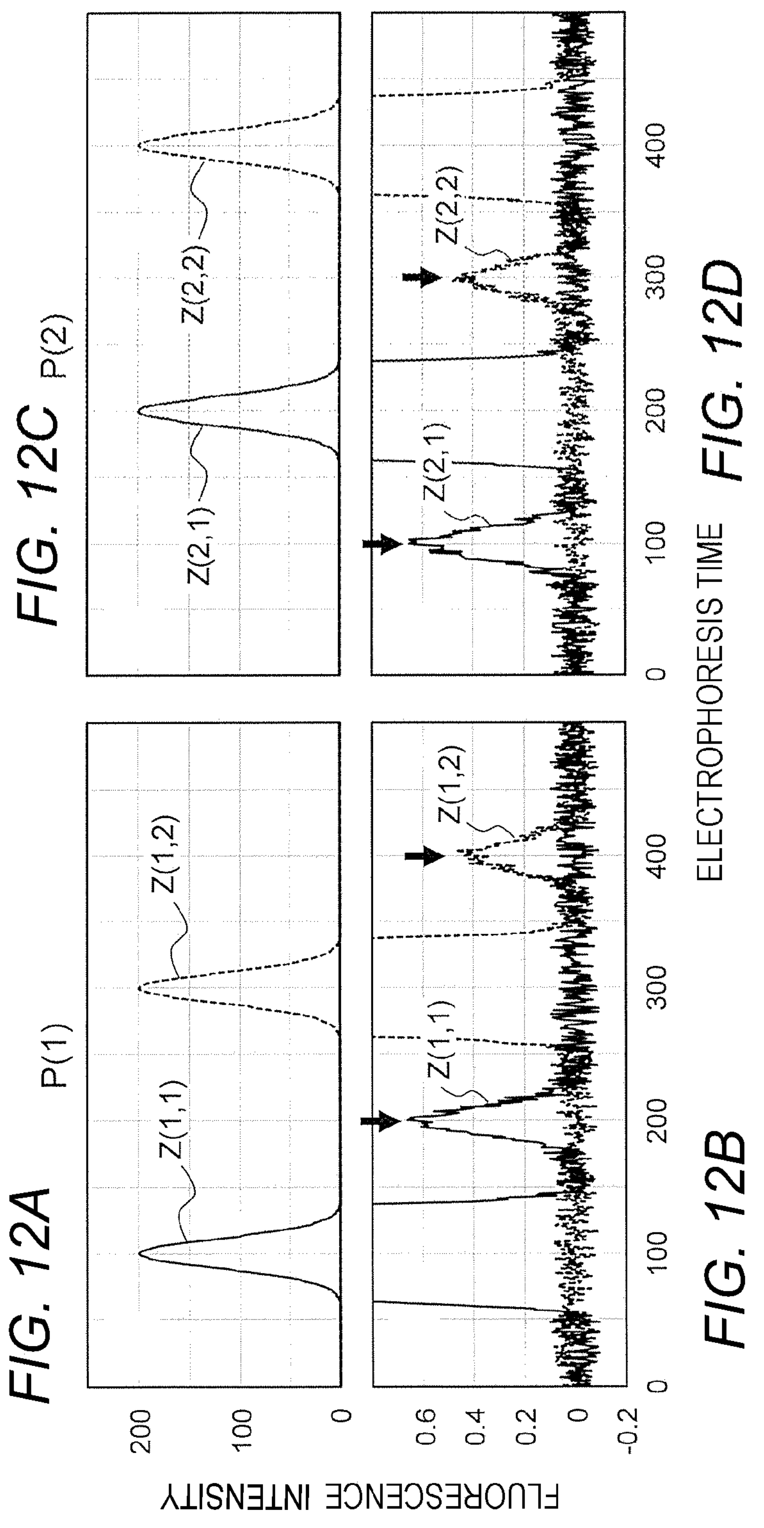
FIGS. 12A-12D illustrates color-converted data with color-conversion processing applied to the raw data of FIGS. 11A to 11D.
Figures 13A, 13B, 13C, 13D:
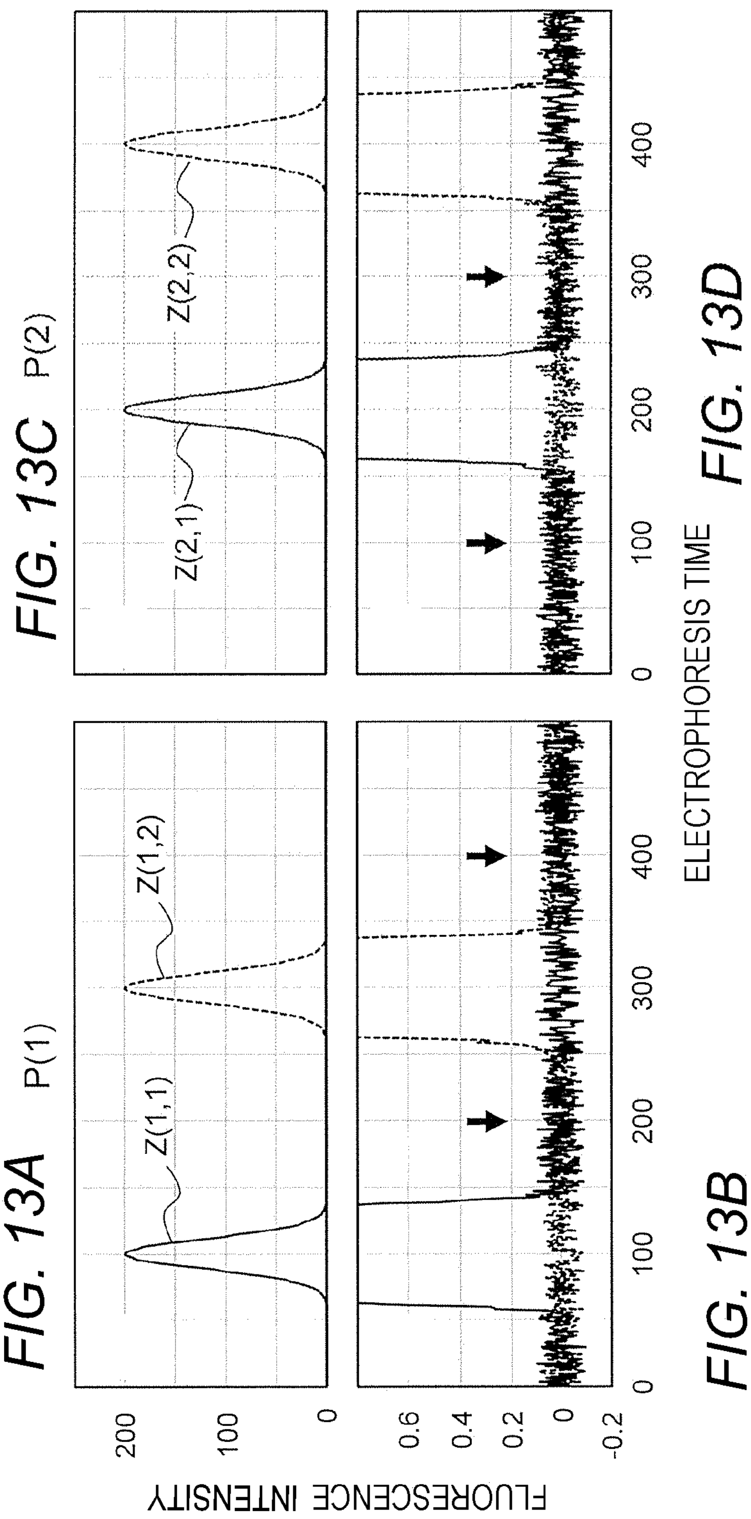
FIGS. 13A-13D illustrates color-converted and spatial-corrected data with color-conversion and spatial-correction processing applied to the raw data of FIGS. 11A to 11D.
Figures 14A, 14B, 14C, 14D:
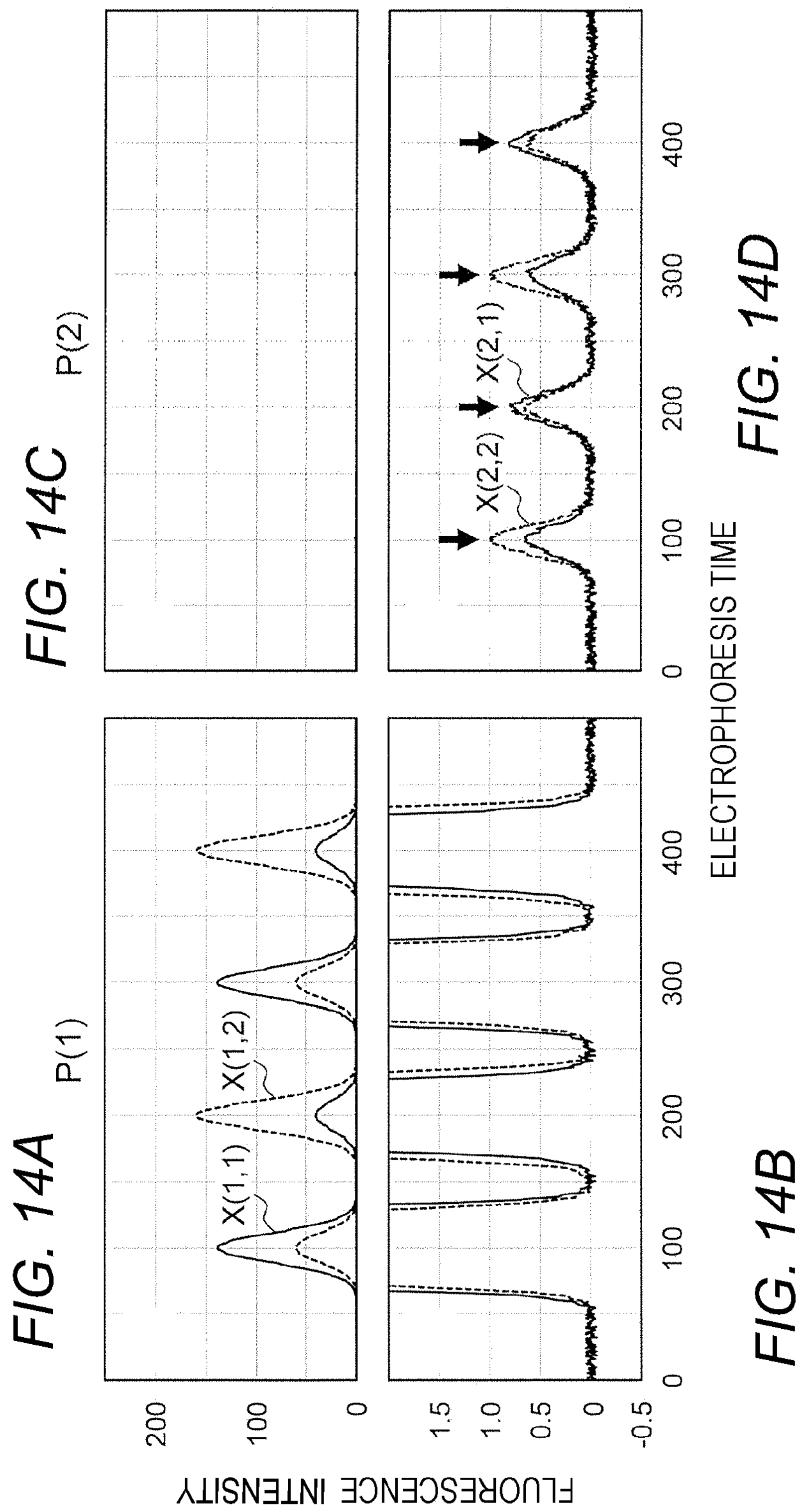
FIGS. 14A-14D illustrates raw data obtained by electrophoresis analyses of unknown samples.

FIGS. 11A to 11D illustrates pieces of raw data obtained by respectively injecting known samples into the capillaries Cap(1) and Cap(2) and performing electrophoresis analyses by using the model experimental system of FIG. 8. In both cases, a horizontal axis represents an electrophoresis time (arbitrary unit), and a vertical axis represents a fluorescence intensity (arbitrary unit). FIGS. 11A and 11B illustrate the same piece of raw data obtained for the light-emitting point P(1). The vertical axis scale in FIG. 11B is larger than that in FIG. 11A. Similarly, FIG. 11C and FIG. 11D illustrate the same piece of raw data obtained for the light-emitting point P(2). The vertical axis scale in FIG. 11D is larger than that in FIG. 11C. The horizontal axis in FIGS. 11A to 11D indicates time from 0 to 500, the vertical axis in FIGS. 11A and 11C indicates fluorescence intensity from 0 to 250, and the vertical axis in FIGS. 11B and 11D indicates fluorescence intensity from −0.2 to 0.8. X(1, 1) and X(2, 1) are represented by solid lines, and X(1, 2) and X(2, 2) are represented by dotted lines. As illustrated in FIGS. 11A to 11D, samples are prepared such that the fluorophore D(1, 1) emits fluorescence alone at the light-emitting point P(1) at time 100 (the state of FIG. 9A), the fluorophore D(2, 1) emits fluorescence alone at the light-emitting point P(2) at time 200 (the state of FIG. 9C), the fluorophore D(1, 2) emits fluorescence alone at the light-emitting point P(1) at time 300 (the state of FIG. 9B), and the fluorophore D(2, 2) emits fluorescence alone at the light-emitting point P(2) at time 400 (the state of FIG. 9D). The samples are prepared such that other fluorescences are not emitted. When only FIGS. 11A and 11C are referenced, only four large peaks corresponding to the above-described fluorescence emissions are observed (corresponding to (i) and (ii) in FIG. 9). However, when FIGS. 11B and 11D are referenced, four small peaks indicated by arrows, that is, fluorescences of the fluorophore D(2, 1) at the light-emitting point P(2) at time 100, the fluorophore D(1, 1) at the light-emitting point P(1) at time 200, the fluorophore D(2, 2) at the light-emitting point P(2) at time 300, and the fluorophore D(1, 2) at the light-emitting point P(1) at time 400 were observed (corresponding to (iii) and (iv) in FIGS. 9A to 9D). Accordingly, it can be determined that these four small peaks are caused by spatial crosstalk and spectral crosstalk. For example, the small peaks of X(2, 1) and X(2, 2) at time 100 corresponding to fluorescence of the fluorophores D(2, 1) and D(2, 2) at the light-emitting point P(2) are caused by detection of a part of the fluorescence emission of the fluorophore D(1, 1) at the light-emitting point P(1) at time 100 due to the spatial crosstalk and the spectral crosstalk (corresponding to (iii) and (iv) in FIG. 9A).

When the spatial crosstalk is not considered, that is, when the four small peaks in FIGS. 11C and 11D are ignored (when only (i) and (ii) are considered in FIGS. 9A to 9D), the elimination of the spectral crosstalk of the four large peaks in FIGS. 11A and 11C, that is, color conversion by the method of the related art may be executed. In this case, (Equation 6) is expressed by the following equation.

[Equation 18]

$$\begin{pmatrix} Z(1,1) \\ Z(1,2) \end{pmatrix} = \begin{pmatrix} 0.7 & 0.2 \\ 0.3 & 0.8 \end{pmatrix}^{-1} \times \begin{pmatrix} X(1,1) \\ X(1,2) \end{pmatrix} = \begin{pmatrix} 1.6 & -0.4 \\ -0.6 & 1.4 \end{pmatrix} \times \begin{pmatrix} X(1,1) \\ X(1,2) \end{pmatrix} \quad \text{(Equation 18)}$$

[Equation 19]

$$\begin{pmatrix} Z(2,1) \\ Z(2,2) \end{pmatrix} = \begin{pmatrix} 0.7 & 0.2 \\ 0.3 & 0.8 \end{pmatrix}^{-1} \times \begin{pmatrix} X(1,1) \\ X(1,2) \end{pmatrix} = \begin{pmatrix} 1.6 & -0.4 \\ -0.6 & 1.4 \end{pmatrix} \times \begin{pmatrix} X(2,1) \\ X(2,2) \end{pmatrix} \quad \text{(Equation 19)}$$

Here, Z(1, 1), Z(1, 2), Z(2, 1), and Z(2, 2) indicate concentrations of the fluorophores D(1, 1), D(1, 2), D(2, 1), and D(2, 2) at each time. As illustrated in (Equation 18) and (Equation 19), in the present embodiment, a matrix Y of 2 rows and 2 columns and an inverse matrix $Y^{-1}$ of 2 rows and 2 columns were the same for the light-emitting points P(1) and P(2). However, in general, a matrix Y and an inverse matrix $Y^{-1}$ may be different for the light-emitting point P(1) and the light-emitting point P(2). Elements of the matrix Y for the light-emitting point P(1) were determined by the intensity ratio between the fluorescence intensities X(1, 1) and X(1, 2) of the fluorophore D(1, 1) at time 100 and the intensity ratio between the fluorescence intensities X(1, 1) and X(1, 2) of the fluorophore D(1, 2) at time 300. Elements of the matrix Y for the light-emitting point P(2) were determined by the intensity ratio between the fluorescence intensities X(2, 1) and X(2, 2) of the fluorophore D(2, 1) at time 200 and the intensity ratio between the fluorescence intensities X(2, 1) and X(2, 2) of the fluorophore D(2, 2) at time 400.

FIGS. 12A to 12D illustrates pieces of color-converted data obtained by executing the color conversions of (Equation 18) and (Equation 19) on the pieces of raw data in FIGS. 11A to 11D at each time. The notation is the same as in FIGS. 11A to 11D. As expected, it can be seen that the spectral crosstalk in the four large peaks in FIGS. 11A and 11C is eliminated in the four large peaks in FIGS. 12A and 12C. On the other hand, it can be seen that the spectral crosstalk of the four small peaks in FIGS. 11B and 11D is also eliminated in the four small peaks (indicated by arrows) in FIGS. 12C and 12D, but the four small peaks themselves still remain in FIGS. 12C and 12D. That is, the spatial crosstalk is not eliminated. This is a problem of the method of the related art.

Thus, for FIGS. 11A to 11D, both the spectral crosstalk and the spatial crosstalk are considered (all of (i) to (iv) in FIGS. 9A to 9D are considered), and both color conversion and spatial correction are executed next. In this case, (Equation 14) is expressed by the following equation.

[Equation 20]

$$\begin{pmatrix} Z(1,1) \\ Z(1,2) \\ Z(2,1) \\ Z(2,2) \end{pmatrix} = \begin{pmatrix} 0.6970 & 0.2000 & 0.0021 & 0.0004 \\ 0.3000 & 0.7980 & 0.0009 & 0.0016 \\ 0.0021 & 0.0004 & 0.6970 & 0.2000 \\ 0.0009 & 0.0016 & 0.3000 & 0.7980 \end{pmatrix}^{-1} \times \begin{pmatrix} X(1,1) \\ X(1,2) \\ X(2,1) \\ X(2,2) \end{pmatrix} \quad \text{(Equation 20)}$$

-continued $$= \begin{pmatrix} 1.6082 & -0.4031 & -0.0048 & 0.0012 \\ -0.6046 & 1.4047 & 0.0012 & -0.0028 \\ -0.0048 & 0.0012 & 1.6082 & -0.4031 \\ 0.0012 & -0.0028 & -0.6046 & 1.4047 \end{pmatrix} \times \begin{pmatrix} X(1,1) \\ X(1,2) \\ X(2,1) \\ X(2,2) \end{pmatrix}$$

The matrix Y and the inverse matrix $Y^{-1}$ are extended from 2 rows and 2 columns in (Equation 18) and (Equation 19) to 4 rows and 4 columns. The color conversion is performed independently for the light-emitting point P(1) and the light-emitting point P(2) in (Equation 18) and (Equation 19), respectively, whereas both the color conversion and the spatial correction are collectively performed for both the light-emitting point P(1) and the light-emitting point P(2) in (Equation 20). Elements of the matrix Y in (Equation 20) were determined by the intensity ratio between the fluorescence intensities X(1, 1), X(1, 2), X(2, 1), and X(2, 2) of the fluorophore D(1, 1) at time 100, the intensity ratio between the fluorescence intensities X(1, 1), X(1, 2), X(2, 1), and X(2, 2) of the fluorophore D(2, 1) at time 200, the intensity ratio between the fluorescence intensities X(1, 1), X(1, 2), X(2, 1), and X(2, 2) of the fluorophore D(1, 2) at time 300, and the intensity ratio between the fluorescence intensities X(1, 1), X(1, 2), X(2, 1), and X(2, 2) of the fluorophore D(2, 2) at time 400 in FIGS. 11A to 11D. The upper left 2 rows and 2 columns and the lower right 2 rows and 2 columns of the matrix Y in (Equation 20) correspond to the matrices Y in (Equation 18) and (Equation 19), respectively, and values of the corresponding elements are substantially equal to each other. Similarly, the upper left 2 rows and 2 columns and the lower right 2 rows and 2 columns of the matrix $Y^{-1}$ in (Equation 20) correspond to the matrices $Y^{-1}$ in (Equation 18) and (Equation 19), respectively, and values of the corresponding elements are substantially equal to each other. That is, these elements are responsible for color conversion for eliminating the spectral crosstalk for each light-emitting point. Here, the reason why the values of these corresponding elements in (Equation 20), (Equation 18), and (Equation 19) are not exactly equal to each other is a difference between whether the spatial crosstalk is considered, as described below. On the other hand, the upper right 2 rows and 2 columns and the lower left 2 rows and 2 columns of the matrix Y and the matrix $Y^{-1}$ in (Equation 20) are responsible for spatial correction and color conversion that eliminate spatial crosstalk and spectral crosstalk between different light-emitting points. These submatrices are not present in (Equation 18) and (Equation 19). The above can be more easily understood by transforming (Equation 20) into the following equations.

[Equation 21]

$$\begin{pmatrix} Z(1,1) \\ Z(1,2) \end{pmatrix} = \begin{pmatrix} 1.6002 & -0.4031 \\ -0.6046 & 1.4047 \end{pmatrix} \times \begin{pmatrix} X(1,1) \\ X(1,2) \end{pmatrix} + \begin{pmatrix} -0.0048 & 0.0012 \\ 0.0012 & -0.0028 \end{pmatrix} \times \begin{pmatrix} X(2,1) \\ X(2,2) \end{pmatrix} \quad \text{(Equation 21)}$$

[Equation 22]

$$\begin{pmatrix} Z(2,1) \\ Z(2,2) \end{pmatrix} = \begin{pmatrix} -0.0048 & 0.0012 \\ 0.0012 & -0.0028 \end{pmatrix} \times \begin{pmatrix} X(1,1) \\ X(1,2) \end{pmatrix} + \quad \text{(Equation 22)}$$

-continued $$\begin{pmatrix} 1.6082 & -0.4031 \\ -0.6046 & 1.4047 \end{pmatrix} \times \begin{pmatrix} X(2,1) \\ X(2,2) \end{pmatrix}$$

The first term on the right side of (Equation 21) and the second term on the right side of (Equation 22) are responsible for color conversion of the method of the related art, and correspond to (Equation 18) and (Equation 19), respectively. On the other hand, the second term on the right side of (Equation 21) and the first term on the right side of (Equation 22) are responsible for both spatial correction and color conversion that are not handled in the method of the related art. Based on the above understanding, the color conversion, and both the spatial correction and the color conversion may be separately executed, or only one of them may be executed. Alternatively, it is also possible to change processing depending on the light-emitting point. For example, it is possible to perform the spatial correction and the color conversion for the light-emitting point P(1) and perform only the color conversion for the light-emitting point P(2).

FIGS. 13A to 13D illustrates pieces of color-converted and spatial-corrected data obtained by simultaneous executing both the color conversion and the spatial correction of (Equation 20) at each time on the raw data in FIGS. 11A to 11D. The notation is the same as in FIGS. 11A to 11D. First, similarly to FIGS. 12A to 12D, it can be seen that the spectral crosstalk in the four large peaks in FIGS. 11A and 11C is eliminated in the four large peaks in FIGS. 13A and 13C. In addition, as expected, it can be seen that the spatial crosstalk and the spectral crosstalk in the four small peaks in FIG. 11B and FIG. 11D are also eliminated in FIG. 13C and FIG. 13D. That is, the four small peaks have disappeared in FIG. 13C and FIG. 13D (indicated by arrows).

As described above, according to the present disclosure, it has been illustrated that spectral crosstalk for each light-emitting point, and both spatial crosstalk and spectral crosstalk between the plurality of light-emitting points can be eliminated or reduced by calculation processing. The above crosstalks are generated in any optical system that detects fluorescences of the plurality of types of fluorophores emitted from the plurality of light-emitting points.

Third Embodiment

Next, unknown samples were analyzed based on the experimental results in [Second Embodiment]. FIGS. 14A to 14D illustrates pieces of raw data obtained by injecting unknown samples into the capillaries Cap(1) and Cap(2) and performing electrophoresis analyses by using the model experimental system of FIG. 8. Since the same model experimental system as that of [Second Embodiment] is used, (Equation 18) to (Equation 22) can be used with no change. The notation is the same as in FIGS. 11A to 11D. However, the vertical axis scale in FIGS. 11B and 11D is reduced to fluorescence intensity of −0.5 to 2.0. At times 100, 200, 300, and 400, large peaks were observed for the light-emitting point P(1), while small peaks (indicated by arrows) were observed for the light-emitting point P(2).

Figures 15A, 15B, 15C, 15D:
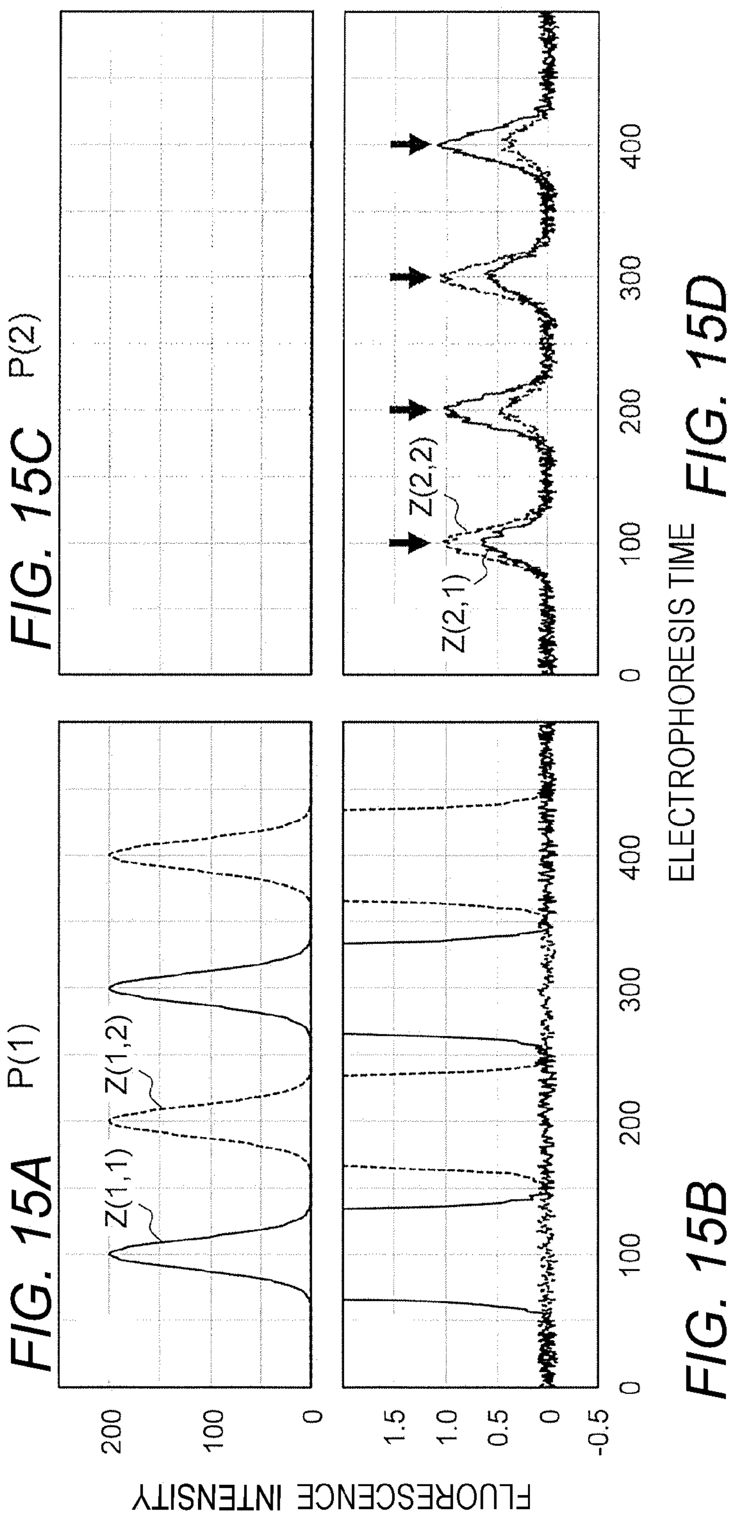
FIGS. 15A-15D illustrates color-converted data with color-conversion processing applied to the raw data of FIGS. 14A to 14D.

FIGS. 15A to 15D illustrates pieces of color-converted data obtained by executing the color conversions of (Equation 18) and (Equation 19) on the pieces of the raw data in FIGS. 14A to 14D at each time. The notation is the same as in FIGS. 14A to 14D. As illustrated in FIG. 15A, at the light-emitting point P(1), the fluorescence emission of the fluorophore D(1, 1) was detected alone at times 100 and 300, and the fluorescence emission of the fluorophore D(1, 2) was detected alone at times 200 and 400. On the other hand, as illustrated in FIG. 15D, at the light-emitting point P(2), the four small peaks (indicated by arrows) detected at times 100, 200, 300, and 400 cannot be identified. That is, it was not clear which of the following (1) to (3) was the origin of the above.

(1) fluorescence emissions of mixtures of the fluorophores D(2, 1) and D(2, 2) at the light-emitting point P(2), (2) fluorescence emissions of impurities other than the fluorophores D(2, 1) and D(2, 2) at the light-emitting point P(2), or (3) the spatial crosstalk of the fluorescence emissions of the fluorophores D(1, 1) and D(1, 2) at the light-emitting point P(1).

Figures 16A, 16B, 16C, 16D:
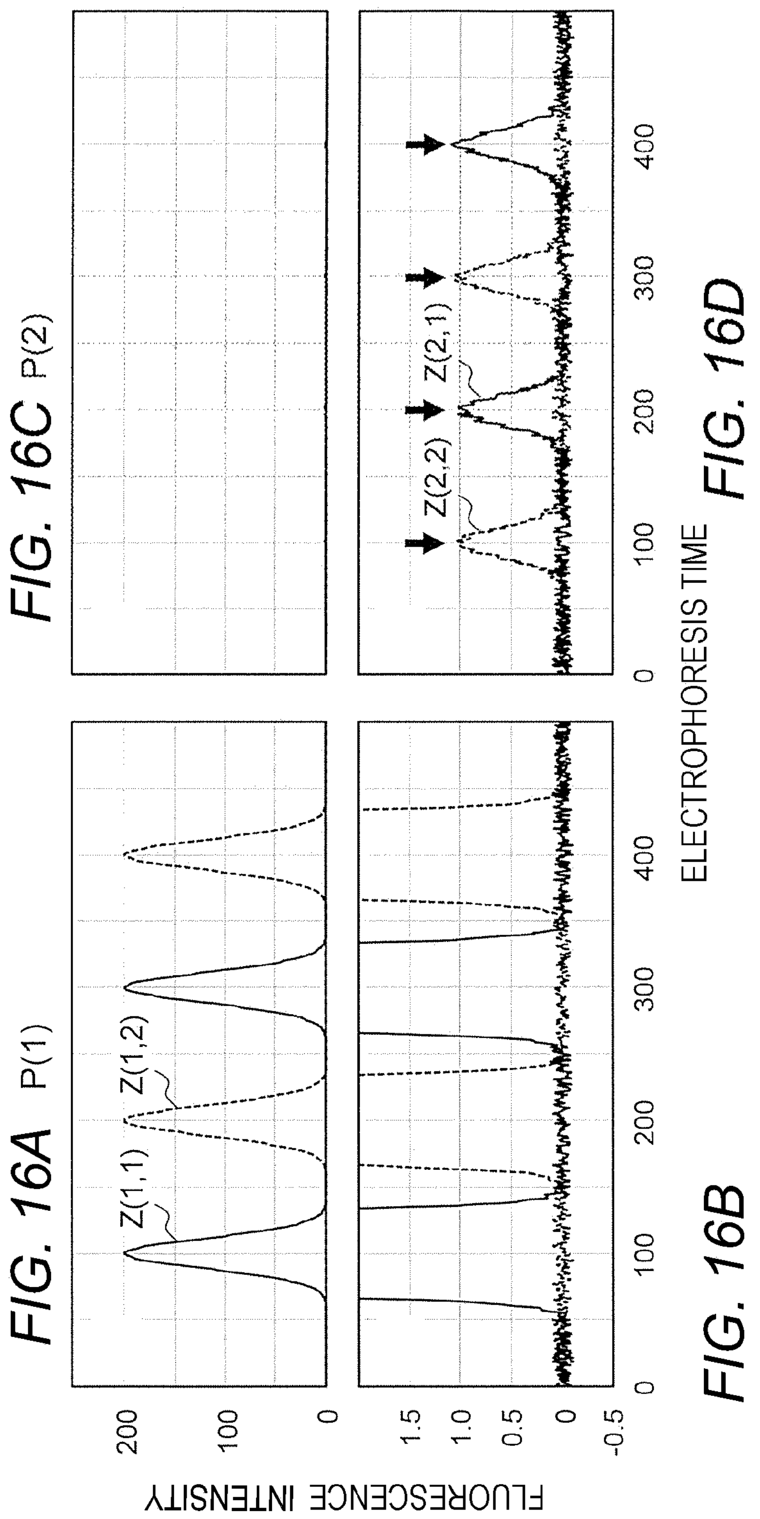
FIGS. 16A-16D illustrates color-converted and spatial-corrected data with color-conversion and spatial-correction processing applied to the raw data of FIGS. 14A to 14D.

FIGS. 16A to 16D illustrates pieces of both color-converted and spatial-corrected data obtained by simultaneous executing both the color conversion and the spatial correction of (Equation 20) at each time on the pieces of raw data in FIGS. 14A to 14D. The notation is the same as in FIGS. 14A to 14D. As illustrated in FIG. 16A, similarly to FIG. 15A, the fluorescence emission of the fluorophore D(1, 1) at the light-emitting point P(1) was detected alone at times 100 and 300. Also, the fluorescence emission of the fluorophore D(1, 2) at the light-emitting point P(1) was detected alone at times 200 and 400. In addition, as illustrated in FIG. 16D, as a result of eliminating the spatial crosstalk and the spectral crosstalk of the fluorescence emissions of the fluorophores D(1, 1) and D(1, 2) at the light-emitting point P(1) to the detection regions W(2, 1) and W(2, 2), it was found that weak fluorescence emissions of the fluorophore D(2, 2) at the light-emitting point P(2) were detected alone at time 100 and 300 and weak fluorescence emissions of the fluorophore D(2, 1) at the light-emitting point P(2) were detected alone at time 200 and 400. Peak intensities of these weak fluorescence emissions were slightly less than 1% of peak intensities of the fluorescence emissions from the light-emitting point P(1). On the other hand, as can be seen from the results of FIGS. 12A to 12D, the spatial crosstalk ratio generated in the model experimental system of FIG. 8 is also slightly less than 1%. Thus, in FIG. 15D, true weak fluorescence emissions and false weak fluorescence emissions due to spatial crosstalk are mixed. Therefore, it is not possible to distinguish between the true weak fluorescence emissions and the false weak fluorescence emissions in FIG. 15D.

The above results indicate that the spatial crosstalk may push up a lower detection limit in the detection of emitted light from each light-emitting point. As in the above example, assuming that the spatial crosstalk ratio is 1%, even if the lower detection limit when there is one light-emitting point is 0.1%, since it is not possible to distinguish whether a signal of 18 or less is a true signal or a false signal due to the spatial crosstalk, an effective lower detection limit rises to 1%. That is, as compared with the detection of the emitted light of one light-emitting point, in the detection of the light emissions of the plurality of light-emitting points, both detection sensitivity and dynamic range are reduced by an order of magnitude. The present disclosure solves such a problem, and can avoid reduction in detection sensitivity and dynamic range in the detection of light emissions of the plurality of light-emitting points.

Fourth Embodiment

Figures 17A, 17B, 17C, 17D:
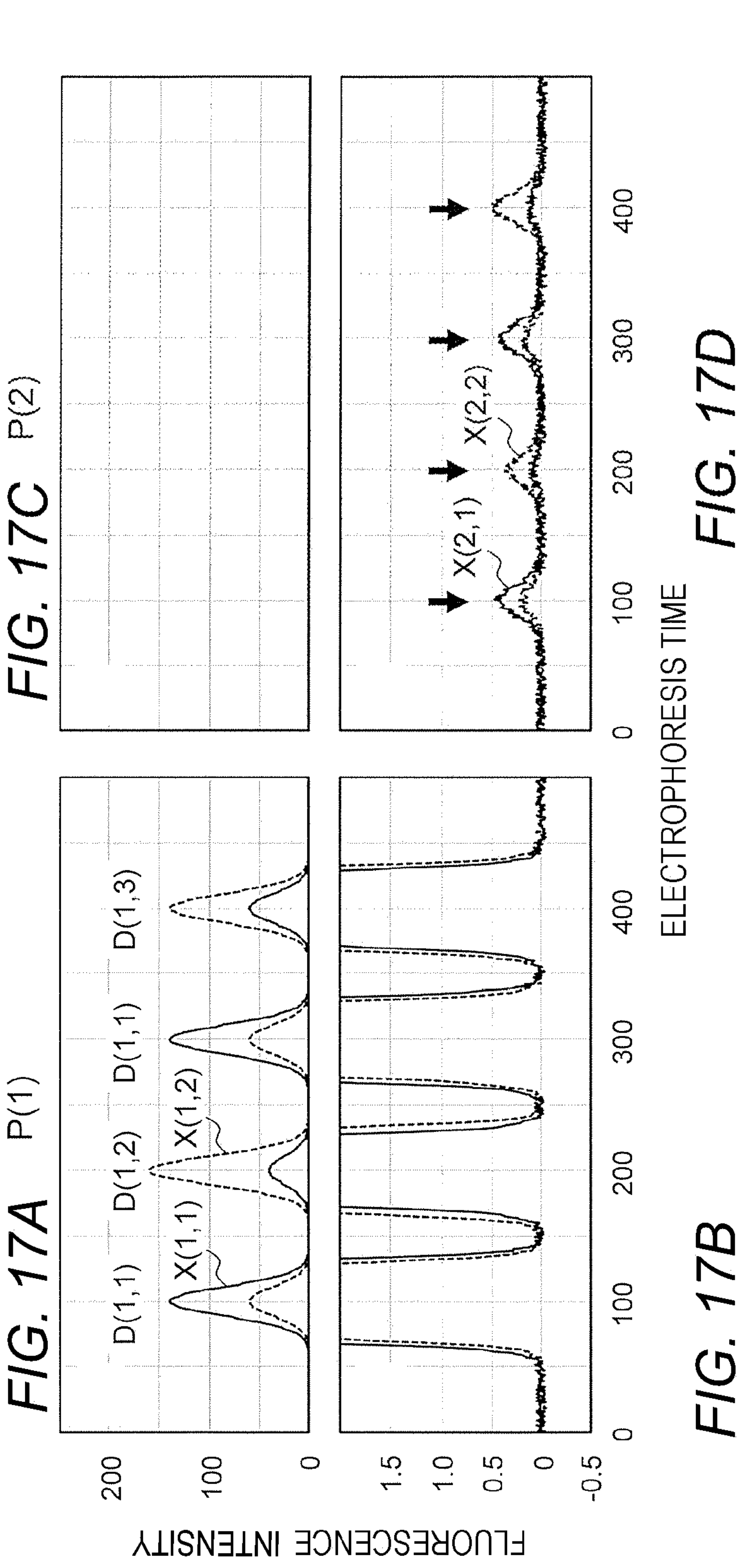
FIGS. 17A-17D illustrates raw data obtained by electrophoresis analyses of samples containing an unknown fluorophore.

Subsequently, based on the experimental results of [Second Embodiment], a sample labeled with the fluorophore D(1, 1), the fluorophore D(1, 2), and an unknown fluorophore D(1, 3) was analyzed by electrophoresis for the light-emitting point P(1). FIGS. 17A to 17D illustrates pieces of raw data obtained by injecting the above sample only into the capillary Cap(1), not injecting any sample into the capillary Cap(2), and performing electrophoresis analyses on both the capillaries Cap(1) and Cap(2) by using the model experimental system of FIG. 8. The notation is the same as in FIGS. 14A to 14D. The sample is prepared such that only the fluorophore D(1, 1) emits fluorescence at the light-emitting point P(1) at time 100, only the fluorophore D(1, 2) emits fluorescence at the light-emitting point P(1) at time 200, only the fluorophore D(1, 1) emits fluorescence at the light-emitting point P(1) at time 300, and only the fluorophore D(1, 3) emits fluorescence at the light-emitting point P(1) at time 400. The sample is also prepared such that no fluorescences other than the above is not emitted. As illustrated in FIG. 17A, only four large peaks corresponding to the fluorescence emissions described above were observed. It was found that the spectral crosstalk ratio of the fluorescence of the fluorophore D(1, 3) is similar to the spectral crosstalk ratio of the fluorescence of the fluorophore D(1, 2), but both the spectral crosstalks are slightly different. On the other hand, it can be seen that each of the four small peaks indicated by the arrows illustrated in FIG. 17D is results of the spatial crosstalk and the spectral crosstalk of the fluorescence emissions that are the sources of the four large peaks in FIG. 17A.

Figures 18A, 18B, 18C, 18D:
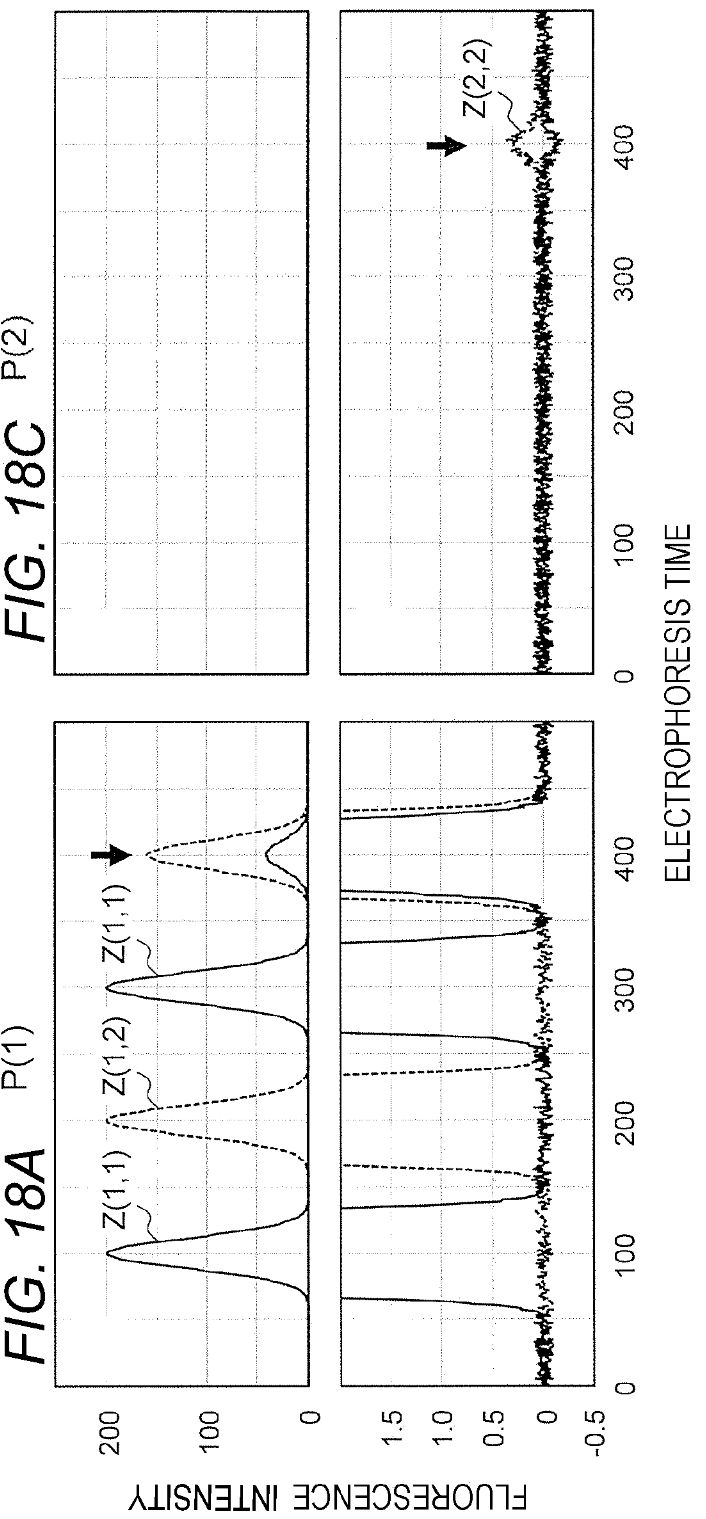
FIGS. 18A-18D illustrates color-converted and spatial-corrected data with color-conversion and spatial-correction processing applied to the raw data of FIGS. 17A to 17D.

FIGS. 18A to 18D illustrates pieces of both color-converted and spatial-corrected data obtained by simultaneous executing both the color conversion and the spatial correction of (Equation 20) at each time on the pieces of raw data in FIGS. 17A to 17D. The notation is the same as in FIGS. 14A to 14D. As illustrated in FIG. 18A, at the light-emitting point P(1), the fluorescence emissions of the fluorophore D(1, 1) were detected alone at times 100 and 300. The fluorescence emission of the fluorophore D(1, 2) was detected alone at time 200. However, as indicated by the arrow, the fluorescence emission of the fluorophore D(1, 3) was detected alone at time 400, but since the spectral crosstalk ratio for the fluorophore D(1, 3) was different from those for both the fluorophore D(1, 1) and the fluorophore D(1, 2), the spectral crosstalk for the fluorophore D(1, 3) was not eliminated. On the other hand, as illustrated in FIG. 18D, although both the spatial crosstalk and the spectral crosstalk of the fluorescence emissions of the fluorophores D(1, 1) and D(1, 2) at the light-emitting point P(1) at times 100,200 and 300 are eliminated, it was found that both the spatial crosstalk and the spectral crosstalk of the fluorescence emission of the fluorophore D(1, 3) at the light-emitting point P(1) at time 400 are not eliminated as indicated by arrows. As a result, the peak at time 400 remain in FIG. 18D. This is because (Equation 20) in [Second Embodiment] is derived using the fluorescence emissions of the fluorophores D(1, 1) and D(1, 2) at the light-emitting point P(1) and the fluorescence emissions of the fluorophores D(2, 1) and D(2, 2) at the light-emitting point P(2). In addition, characteristics of the spatial crosstalk and the spectral crosstalk of the fluorescence emission of D(1, 3) at the light-emitting point P(1) are different from (Equation 20). Accordingly, the above problem can be solved by re-acquiring (Equation 20) for the fluorescence emission of the fluorophore D(1, 3) at the light-emitting point P(1). The above phenomenon represents one aspect of the present disclosure.

Fifth Embodiment

Figures 19A, 19B, 19C, 19D:
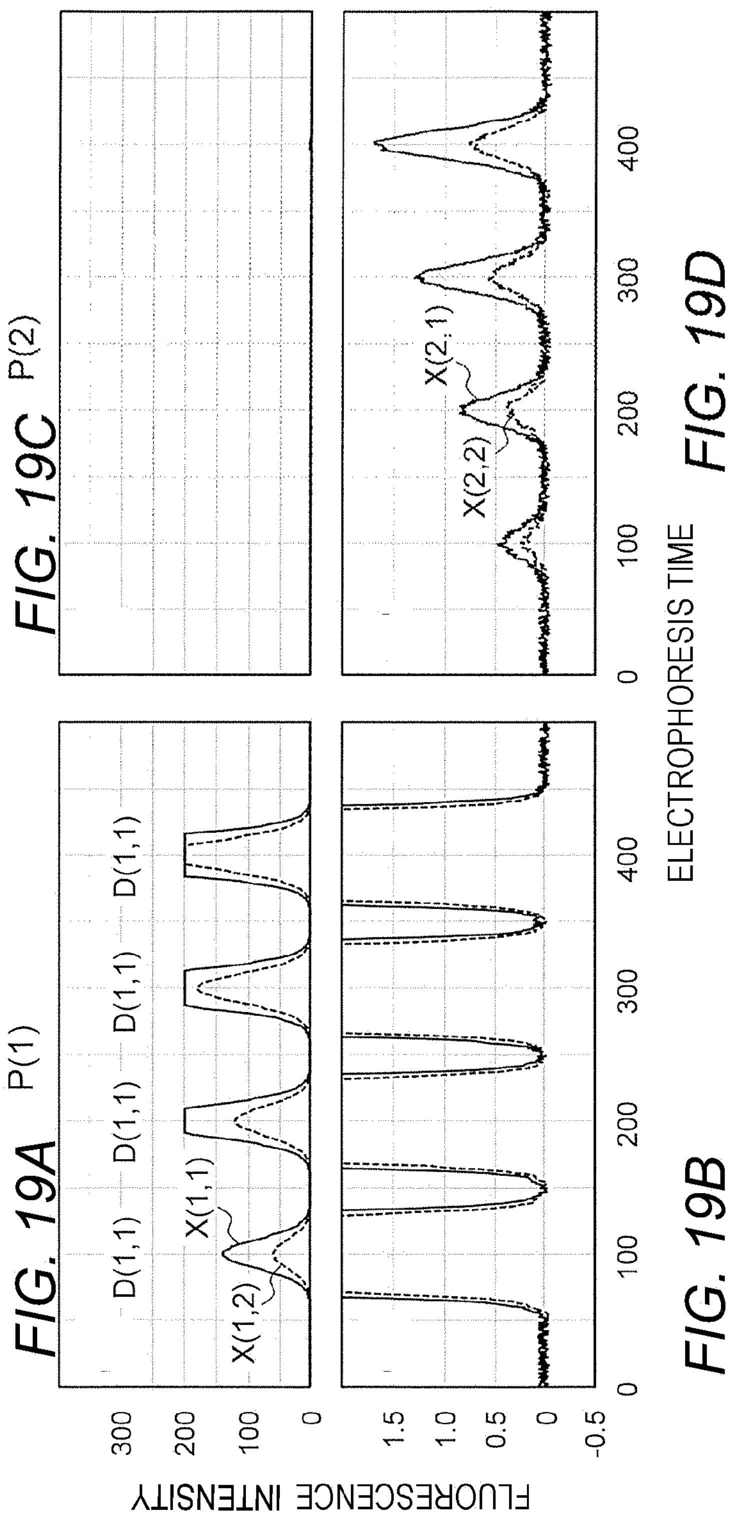
FIGS. 19A-19D illustrates raw data obtained by electrophoresis analyses of samples containing different components labeled with a known fluorophore with varying concentrations.

Now, based on the experimental results of [Second Embodiment], an experiment using a sample in which the concentration of the components labeled with the fluorophore D(1, 1) gradually increases for the light-emitting point P(1) was conducted. FIGS. 19A to 19D illustrates pieces of raw data obtained by injecting the above sample only into the capillary Cap(1), not injecting any sample into the capillary Cap(2), and performing electrophoresis analyses on both the capillaries Cap(1) and Cap(2) by using the model experimental system of FIG. 8. The notation is the same as in FIGS. 14A to 14D. However, a vertical axis scale in FIGS. 19A and 19C is reduced to a fluorescence intensity of 0 to 400. The sample is prepared such that the fluorophores D(1, 1) emits fluorescence alone at the light-emitting point P(1) at times 100, 200, 300, and 400, and the concentration and the fluorescence intensity of the fluorophore D(1, 1) increase gradually. The sample is also prepared such that other fluorescences are not emitted. As illustrated in FIG. 19(*a*), four large peaks corresponding to the above fluorescence emissions were observed. Since the sensor S used in the model experimental system of FIG. 8 saturated at a fluorescence intensity of 200, three peaks at times 200, 300, and 400 were detected in a saturated state. On the other hand, as illustrated in FIG. 19D, four small peaks caused by the spatial crosstalk and the spectral crosstalk of the fluorescence emissions of the fluorophore D(1, 1) at the light-emitting point P(1) were observed in an unsaturated state since each fluorescence intensity is low.

Figures 20A, 20B, 20C, 20D:
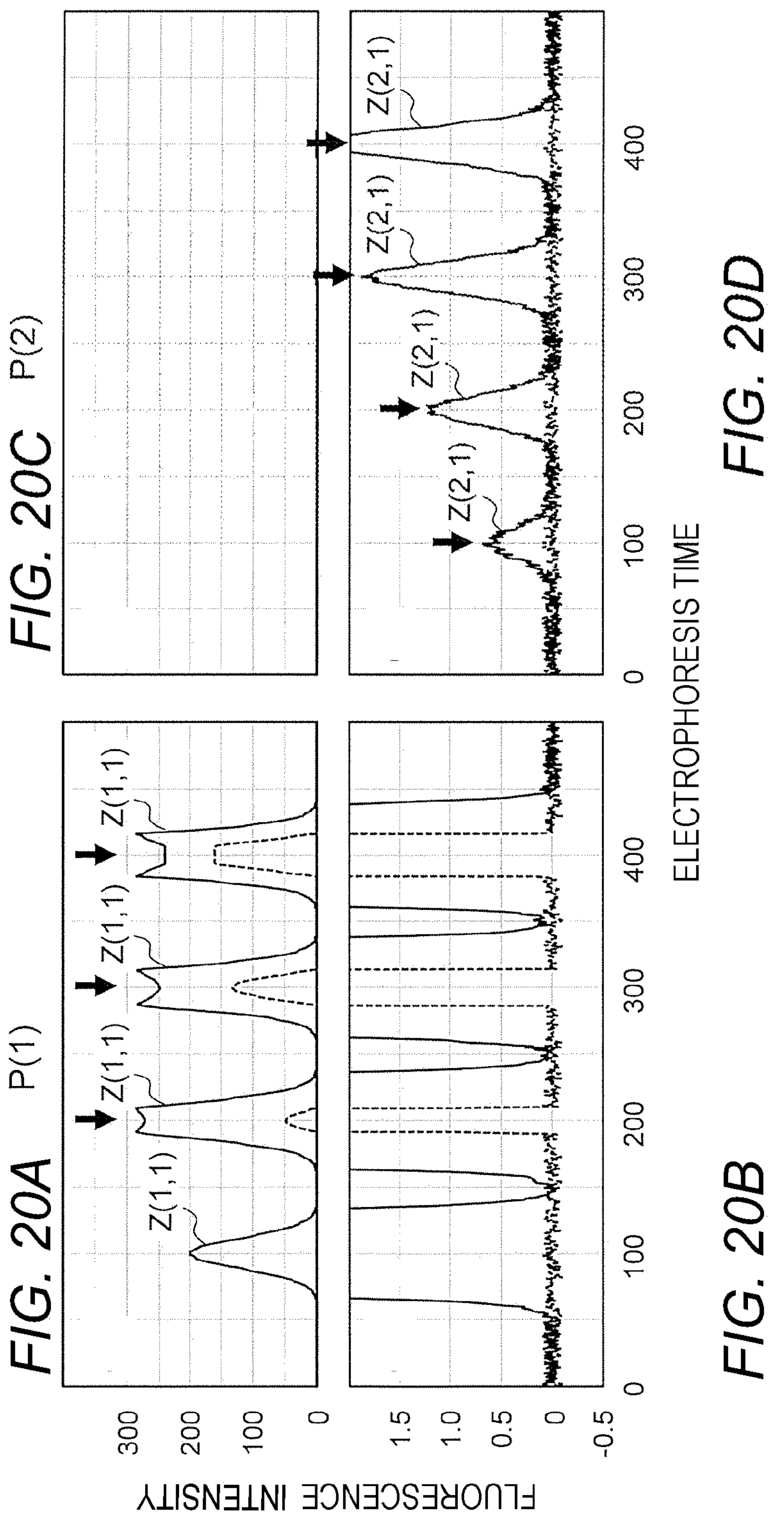
FIGS. 20A-20D illustrates color-converted data with color-conversion processing applied to the raw data of FIGS. 19A to 19D.

FIGS. 20A to 20D illustrates pieces of color-converted data obtained by executing the color conversions of (Equation 18) and (Equation 19) on the pieces of raw data in FIGS. 19A to 19D at each time. The notation is the same as in FIGS. 19A to 19D. As illustrated in FIG. 20A, the fluorescence emission of the fluorophore D(1, 1) at the light-emitting point P(1) at time 100 was detected alone by eliminating the spectral crosstalk. However, since the fluorescence emissions of the fluorophore D(1, 1) at times 200, 300, and 400 were detected in the saturated state, their spectral crosstalks were not eliminated. As is clear from FIG. 19A, this is because when the fluorescence intensity is saturated, the spectral crosstalk ratio derived from the fluorescence intensity ratio between X(1, 1) and X(1, 2) changes and deviates from the spectral crosstalk ratio defined by (Equation 18) and (Equation 19). On the other hand, as illustrated in FIG. 20D, since the fluorescence intensity of the fluorophore D(2, 1) was not saturated, the spectral crosstalk was eliminated for each of the four small peaks indicated by the arrows. The fluorescence intensity ratio between the four peaks illustrated in FIG. 20D represents the actual fluorescence intensity ratio between the fluorescence emissions of the fluorophore D(1, 1) at the light-emitting point P(1) at times 100, 200, 300, and 400.

Figures 21A, 21B, 21C, 21D:
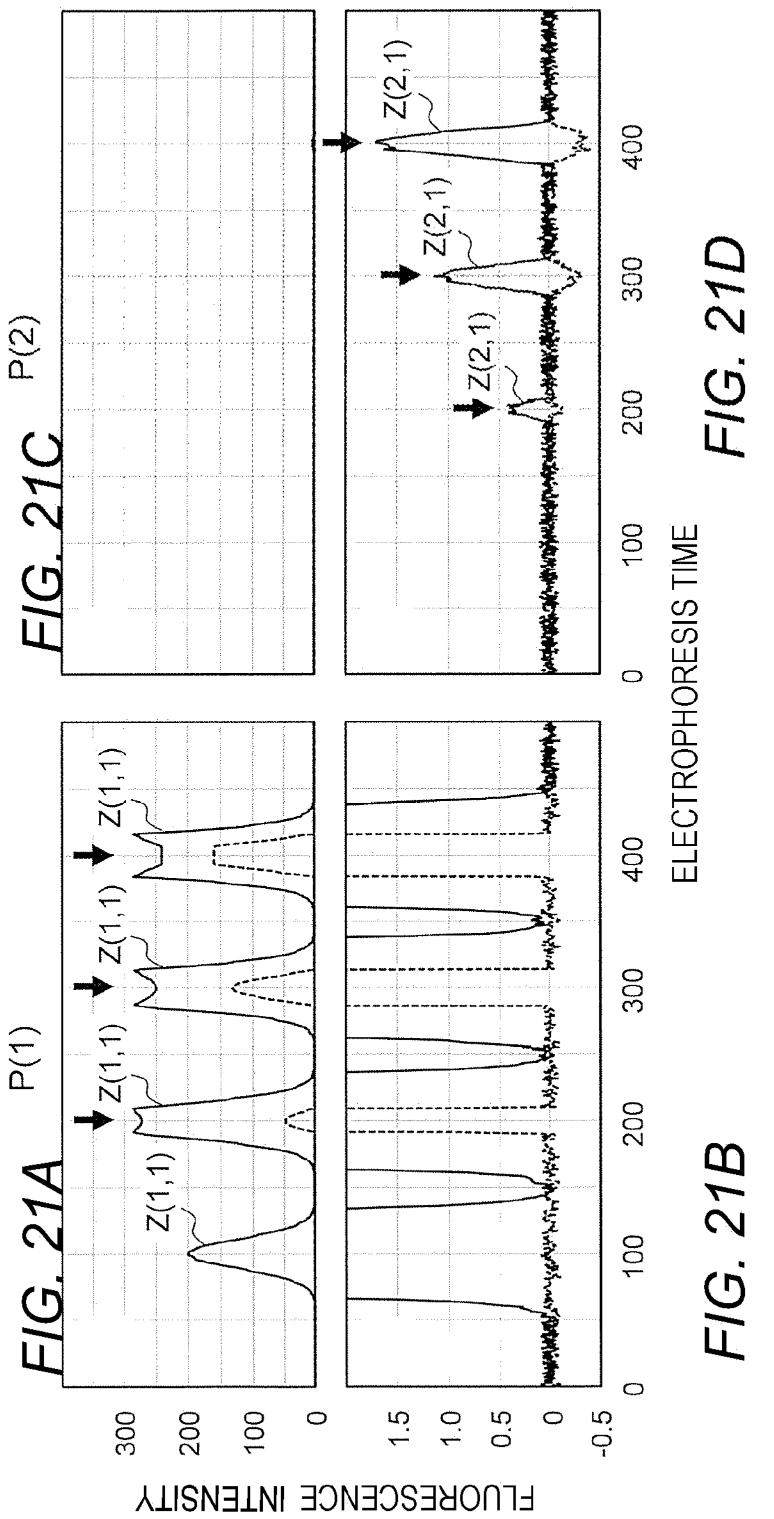
FIGS. 21A-21D illustrates color-converted and spatial-corrected data with color-conversion and spatial-correction processing applied to the raw data of FIGS. 19A to 19D.

FIGS. 21A to 21D illustrates pieces of both color-converted and spatial-corrected data obtained by simultaneous executing both the color conversion and the spatial correction of (Equation 20) at each time on the pieces of raw data in FIGS. 19A to 19D. The notation is the same as in FIGS. 19A to 19D. The same results as in FIG. 20A are obtained in FIG. 21A for the same reason as in FIG. 20A. On the other hand, as illustrated in FIG. 21D, both the spatial crosstalk and the spectral crosstalk were eliminated for the fluorescence emission of the fluorophore D(2, 1) at time 100. However, both the spatial crosstalk and the spectral crosstalk were not eliminated for the fluorescence emissions of the fluorophore D(2, 1) at times 200, 300, and 400. This is because the ratios of the fluorescence intensities of X(2, 1) and X(2, 2) illustrated in FIG. 19D to the fluorescence intensities of X(1, 1) and X(1, 2) illustrated in FIG. 19A deviate from the spatial crosstalk ratios defined by (Equation 20) as a result of saturation of the fluorescence intensity of X(1, 1) or X(1, 2) illustrated in FIG. 19A at times 200, 300, and 400. Since a degree of the deviation increases with a degree of saturation, in FIG. 21D, the fluorescence intensity of the fluorophore D(2, 1) at time 300 is larger than that at time 200, and the fluorescence intensity of the fluorophore D(2, 1) at time 400 is larger than that at time 300.

Sixth Embodiment

Here, a different method from [Second Embodiment] to determine the matrix Y in (Equation 20) will be described. In [Second Embodiment], as illustrated in FIG. 11A, the matrix Y was determined by making the fluorophores D(1, 1), D(2, 1), D(1, 2), and D(2, 2) emit fluorescences separately in this order, that is, by alternately making the fluorophores emit fluorescences at the light-emitting point P(1) and the light-emitting point P(2). However, when either an electrophoresis speed in the capillaries Cap(1) or Cap(2) is deviated from an assumed speed, the fluorescence emissions at the light-emitting point P(1) and the light-emitting point P(2) may be simultaneously emitted. In this case, the matrix Y cannot be determined.

Figure 22A:
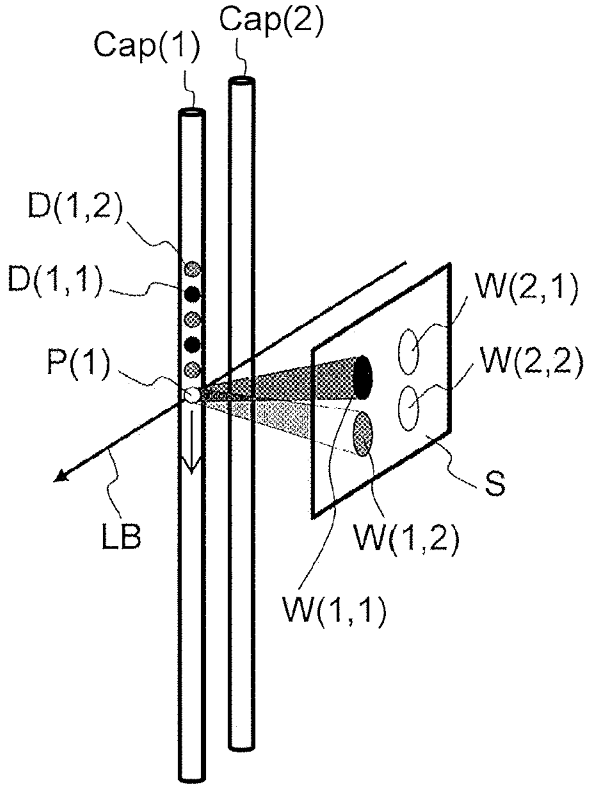
FIGS. 22A-22B is a schematic diagram of a method for injecting samples into a plurality of capillaries at different times.
Figure 22B:
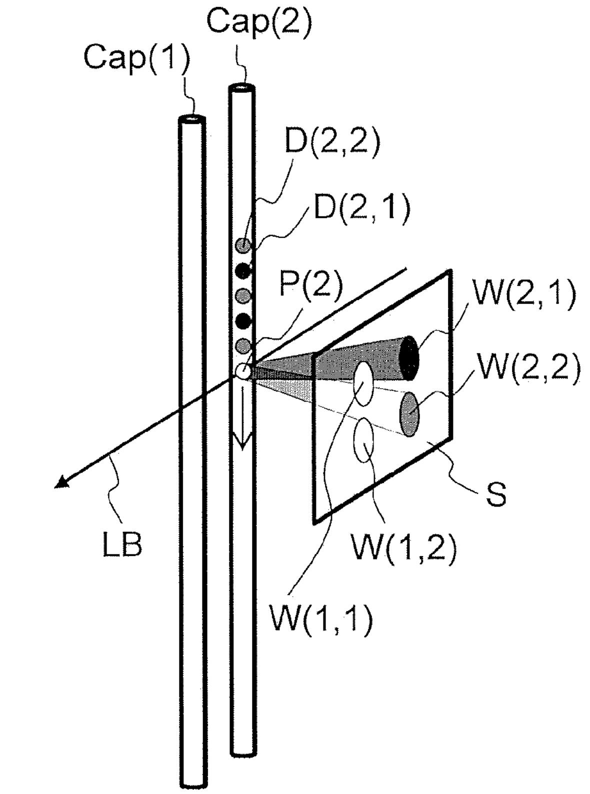

FIGS. 22A to 22B illustrates a more realistic method for avoiding the above problem. First, as illustrated in FIG. 22A, a sample is injected only into the capillary Cap(1), electrophoresis analyses are performed in the capillaries Cap(1) and Cap(2), and the fluorophores D(1, 1) and D(1, 2) emit fluorescences separately. Then, the detection of the emitted fluorescences is performed in the detection regions W(1, 1), W(1, 2), W(2, 1), and W(2, 2). Subsequently, as illustrated in FIG. 22B, a sample is injected only into the capillary Cap(2), electrophoresis analyses are performed in the capillaries Cap(1) and Cap(2), and the fluorophores D(2, 1) and D(2, 2) emit fluorescences separately. Then, the detection of the emitted fluorescences is performed in the detection regions W(1, 1), W(1, 2), W(2, 1), and W(2, 2). In this way, similarly to [Second Embodiment], the matrix Y can be determined. According to this method, the matrix Y can be determined more easily and reliably than the method in [Second Embodiment]. In FIGS. 22A to 22B, for easy understanding, each of the fluorophores D(1, 1) and D(1, 2) in the capillary Cap(1) and the fluorophores D(2, 1) and D(2, 2) in the capillary Cap(2) emit fluorescences a plurality of times, but each only needs to emit fluorescence once. In the above description, although the second electrophoretic analyses were performed after the first electrophoretic analyses was completed, the interval between these electrophoretic analyses may be shortened. The same effect as the effect in FIGS. 22A to 22B can be obtained by appropriately shifting timings of the sample injections into the capillary Cap(1) and the capillary Cap(2). For example, electrophoresis may be performed for a short time after the first sample is injected into the capillary Cap(1), then the second sample is injected into the capillary Cap(2) and the electrophoresis is resumed. In this manner, a time required to determine the matrix Y can be reduced. According to this method, the sample to be injected into the capillary Cap(1) and the sample to be injected into the capillary Cap(2) can have the same composition or can be the same. Accordingly, the sample to be prepared can be simplified, and the cost therefor can be reduced.

Figure 23:
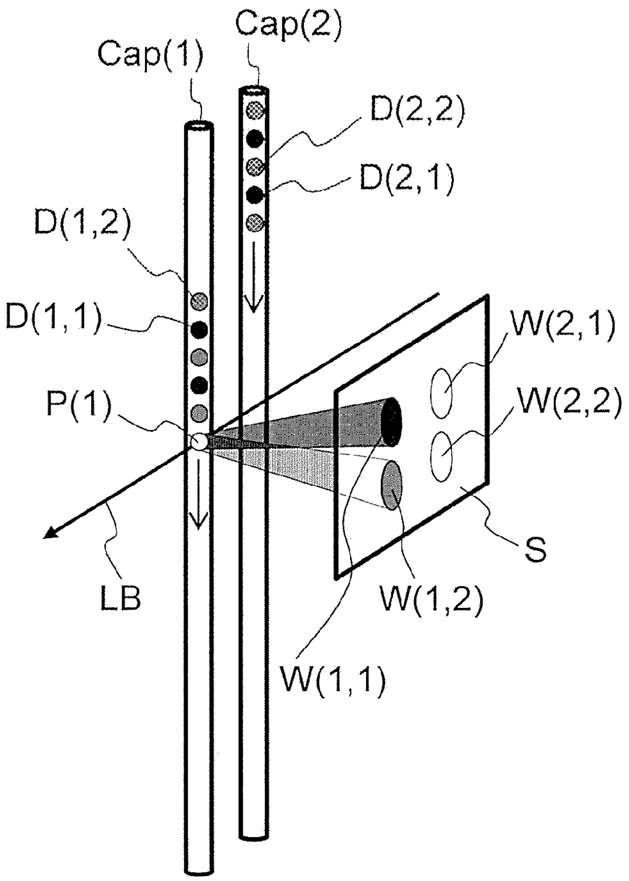
FIG. 23 is a schematic diagram of a method for detecting fluorescence emissions from a plurality of capillaries at different times.

FIG. 23 illustrates a method for further simplifying the determination of the matrix Y. Here, samples are prepared such that the fluorophores D(1, 1) and D(1, 2) in the capillary Cap(1) and the fluorophores D(2, 1) and D(2, 2) in the capillary Cap(2) emit fluorescences at different times, similarly to FIGS. 22A to 22B, even though the sample injections into the capillary Cap(1) and the capillary Cap(2) are performed at the same timing. That is, a composition of the samples to be injected into the capillary Cap(1) and the capillary Cap(2) is different. More specifically, components labeled with the fluorophores in the both samples migrate at different electrophoresis speeds. For example, the sample to be injected into the capillary Cap(1) may include a DNA fragment having a 50 base length and labeled with the fluorophore D(1, 1) and a DNA fragment having a 60 base length and labeled with the fluorophore D(1, 2). The sample to be injected into the capillary Cap(2) may include a DNA fragment having a 70 base length and labeled with the fluorophore D(2, 1) and a DNA fragment having 80 base length and labeled with the fluorophore D(2, 2).

Alternatively, FIG. 23 can also be realized by setting different electrophoresis conditions for the capillaries Cap (1) and Cap(2) even though the same sample is injected into the capillaries Cap(1) and Cap(2) at the same timing. For example, a voltage applied to Capi(2) is temporarily decreased during electrophoresis, a temperature of Capi(2) during electrophoresis is decreased, or the like.

In the above description, it is assumed that dedicated samples for determining the matrix Y are prepared in advance, but the present disclosure is not limited thereto. In the pieces of raw data of the electrophoresis analysis results of a real sample to be analyzed, when there is a state in which a fluorescence emission of each fluorophore in each capillary is generated separately and each state is identified, the matrix Y can be determined by using the pieces of raw data at the time in each state.

Seventh Embodiment

Figure 24:
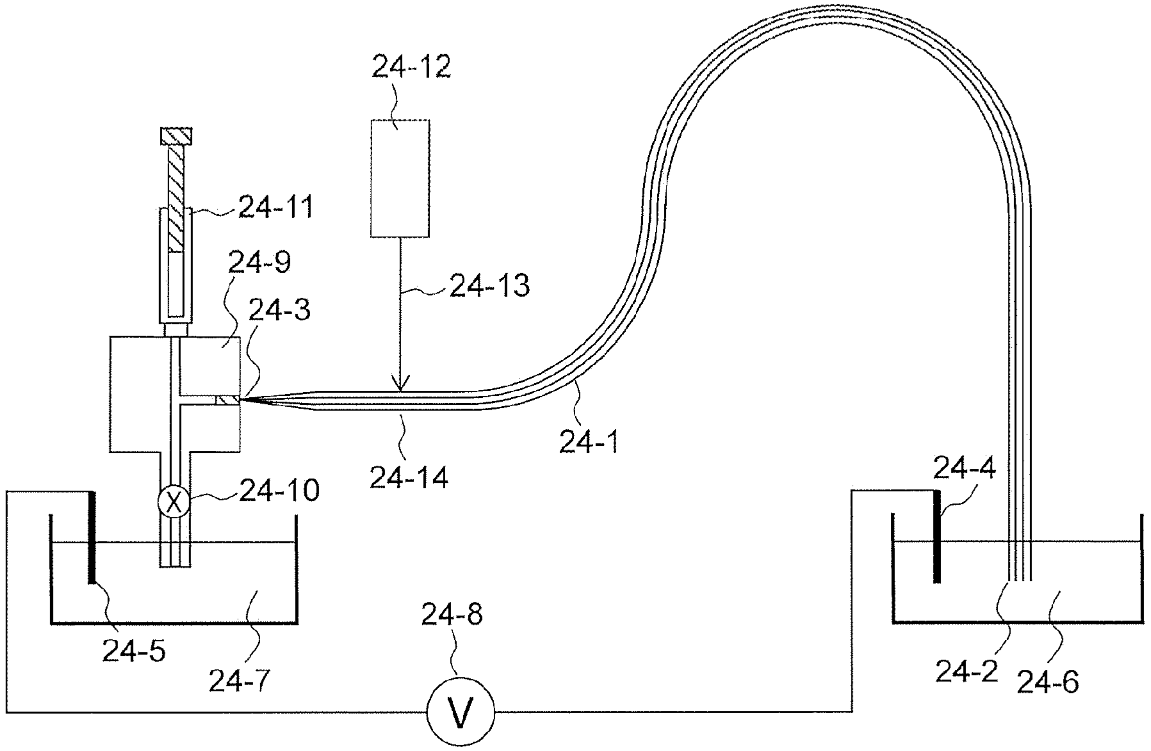
FIG. 24 is a schematic diagram of a multi-capillary electrophoresis system.

FIG. 24 is a configuration diagram of a multi-capillary electrophoresis system which is an example of an analysis system. The multi-capillary electrophoresis system is widely used as an analysis system that performs DNA sequencing and DNA fragment analysis. As illustrated in FIG. 24, the multi-capillary electrophoresis system includes multiple capillaries 24-1, a cathode 24-4, an anode 24-5, a cathode-side buffer solution 24-6, an anode-side buffer solution 24-7, a pump block 24-9, a syringe 24-11, and a laser light source 24-12. In the present embodiment, DNA sequencing of four different samples was performed using four capillaries 24-1. Each sample for DNA sequencing includes DNA fragments labeled with four types of fluorophores. One analysis session was executed by the following steps (1) to (6).

(1) First, sample injection ends 24-2 of the four capillaries 24-1 were immersed in the cathode-side buffer solution 24-6. Sample elution ends 24-3 were connected to the anode-side buffer solution 24-7 via a polymer solution in the polymer block 24-9.

(2) Next, the internal polymer solution was pressurized by closing a valve 24-10 of the pump block 24-9 and pushing down a piston of the syringe 24-11 connected to the pump block 24-9. The polymer solution was filled into the capillaries 24-1 from the sample elution ends 24-3 toward the sample injection ends 24-2. (3) Subsequently, after opening the valve 24-10, electrokinetically injecting the different samples into the capillaries 24-1 from the sample injection ends 24-2, capillary electrophoresis was started for each capillary by applying a high voltage between the cathode 24-4 and the anode 24-5 by a power supply 24-8. The DNA fragments labeled with the four types of fluorophores were electrophoresed from the sample injection ends 24-2 toward the sample elution ends 24-3. (4) In parallel, positions of a certain electrophoresis distance from the sample injection end 24-2 on the capillaries 24-1 were set as light-emitting points 24-14. The light-emitting points 24-14 were simultaneously irradiated with a laser beam 24-13 having a wavelength of 505 nm oscillated from the laser light source 24-12. Here, the outer coating of the capillaries 24-1 in of the vicinity the light-emitting points 24-14 was removed in advance. The capillaries 24-1 in the vicinity of the light-emitting points 24-14 were arranged on the same plane (an arrangement plane). The laser beam 24-13 was condensed and then introduced along the arrangement plane from a side of the arrangement plane. (5) The DNA fragments labeled with the four types of fluorophores were electrophoresed inside the capillaries 24-1, and the four types of fluorophores were excited by irradiation of the laser beam 24-13 to emit fluorescences when passing through the light-emitting points 24-14. That is, the four types of fluorophores emitted the fluorescences from the four light-emitting points, and each fluorescence intensity changed from moment to moment with electrophoresis. (6) Finally, the DNA sequencing of the samples injected into the capillaries was executed by performing multicolor detection of the fluorescences emitted from the light-emitting points by a sensor (not illustrated) and analyzing pieces of time-series data of the obtained fluorescence intensities by a computer (not illustrated). The analysis session including the above steps (1) to (6) can be repeated a plurality of times. For example, a large number of different samples can be analyzed by analyzing samples [1] to [4] in a first analysis session and analyzing samples [5] to [8] in a second analysis session.

Figure 25:
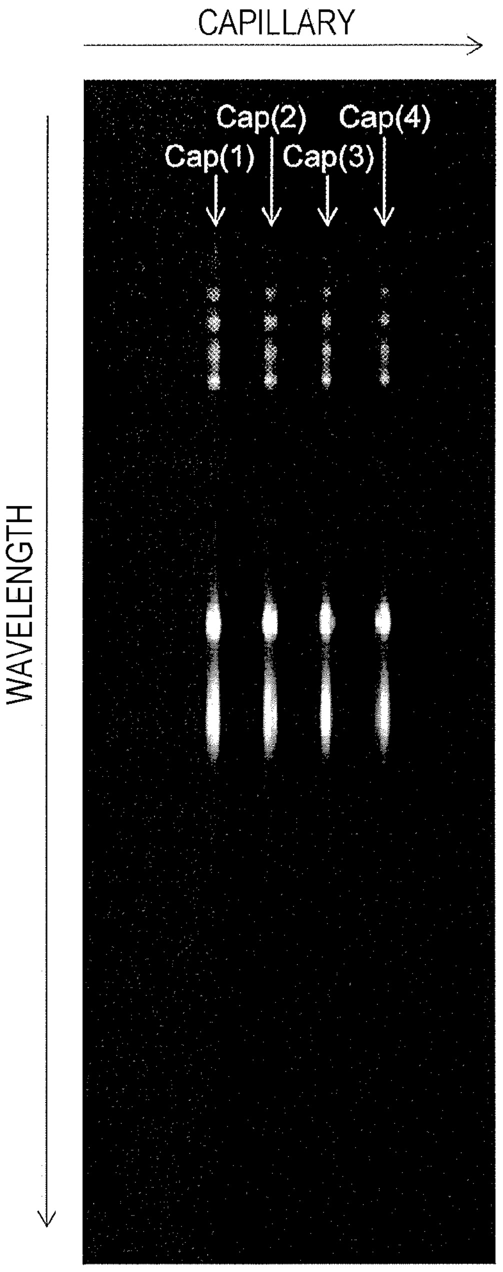
FIG. 25 illustrates wavelength-dispersion images of Raman-scattering lights from four capillaries by an optical system of PTL 1.
Figure 26:
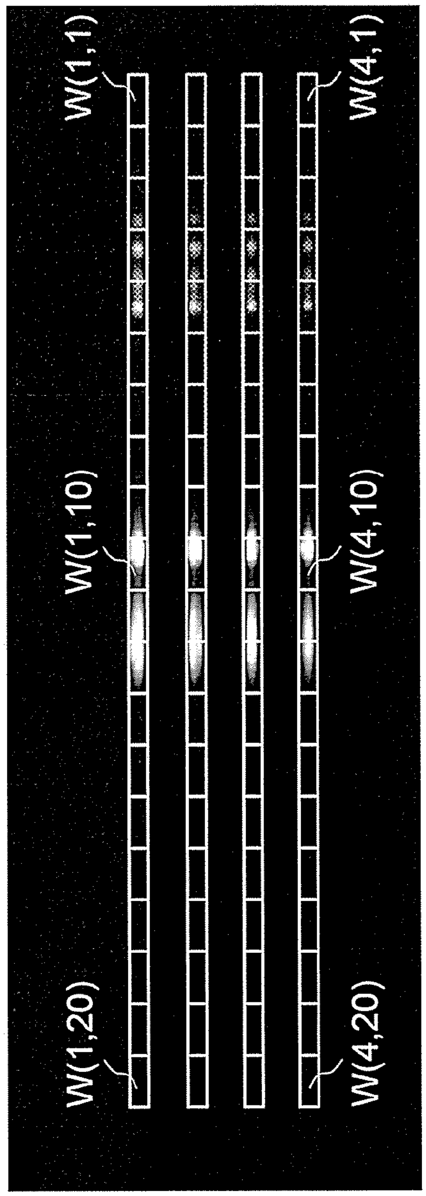
FIG. 26 is a diagram illustrating setting of detection regions of 20 wavelength bands for the capillaries in FIG. 25.

In the present embodiment, the multicolor detection in the above (6) was performed by using the optical system of PTL 1. That is, fluorescences emitted from A=four light-emitting points P(1) to P(4) were collimated by one condenser lens and transmitted through one transmission-type diffraction grating. Then, first-order diffracted lights of the fluorescences were imaged on one two-dimensional sensor by one imaging lens. FIG. 25 illustrates the obtained two-dimensional sensor image including wavelength-dispersion images of Raman scattering lights emitted from the four light-emitting points P(1) to P(4) by laser-beam irradiation when the four capillaries Cap(1) to Cap(4) were filled with a standard solution. A horizontal axis direction is an arrangement direction of the four capillaries. A vertical axis direction is a wavelength direction. Four stripe-shaped images extending in a longitudinal direction indicated by arrows are the wavelength-dispersion images of the Raman scattering lights from the capillaries Cap(1) to Cap(4), respectively. Based on this result, a relationship between a pixel position and a wavelength on the two-dimensional sensor image was obtained by performing wavelength calibration of the wavelength-dispersion images for each of the light-emitting points. Accordingly, as illustrated in FIG. 26, B=20 detection regions of different wavelength bands were set on the two-dimensional sensor image for each of the light-emitting points P(1) to P(4). Each of the 20 detection regions were set so as to detect light emission of each wavelength bands obtained by dividing wavelength band of 500 to 700 nm into 20 equal parts at intervals of 10 nm. For example, the detection regions W(1, 1), W(1, 2), . . . , and W(1, 20) for the light-emitting point P(1) were set so as to detect the light emissions in the wavelength bands of 500 to 510 nm, 510 to 520 nm, . . . , and 690 to 700 nm, respectively. The signal intensities of W(1, 1), W(1, 2), . . . , and W(1, 20) were set as X(1, 1), X(1, 2), . . . , and X(1, 20), respectively. The same applies to the light-emitting points P(2) to P(4). Here, as long as the positions of the light-emitting points P(1) to P(4) and the optical system are fixed, since the relationship between the pixel position and the wavelength for each capillary in the two-dimensional sensor image is maintained, the detection regions set in FIG. 26 are effective for a plurality of different light-emission detections or a plurality of different analysis sessions.

In the present embodiment, C=4 types of fluorophores were selected, specifically DNA fragments of which terminal base species are T, C, A, and G prepared by Sanger reaction were labeled with dR110, dR6G, dTAMRA, and dROX. Since maximum wavelengths of fluorescence emissions of dR110, dR6G, dTAMRA, and dROX are 541 nm, 568 nm, 595 nm, and 618 nm, respectively, the fluorescence emissions of dR110, dR6G, dTAMRA, and dROX are detected with highest intensities in the detection regions of wavelength bands of 540 to 550 nm, 560 to 570 nm, 590 to 600 nm, and 610 to 620 nm, respectively. For example, the fluorescence emissions of dR110, dR6G, dTAMRA, and dROX at the light-emitting point P(1) are mainly detected in the detection regions W(1, 5), W(1, 7), W(1, 10), and W(1, 12), respectively. However, the fluorescence emissions are also detected in the other detection regions for the light-emitting point P(1) due to the spectral crosstalk, and are also detected with weak intensities in the detection regions for the light-emitting points P(2) to P(3) due to the spatial crosstalk and the spectral crosstalk. Hereinafter, dR110, dR6G, dTAMRA, and dROX at the light-emitting point P(1) were defined as D(1, 1), D(1, 2), D(1, 3), and D(1, 4), respectively, and concentrations thereof were defined as Z(1, 1), Z(1, 2), Z(1, 3), and Z(1, 4). The same applies to the light-emitting points P(2) to P(4).

In this case, (Equation 10) to (Equation 12) in (Equation 9) are as follows.

[Equation 23]

$$X=\begin{pmatrix} X(1,1)\\ \vdots\\ X(1,20)\\ X(2,1)\\ \vdots\\ X(4,20)\end{pmatrix} \quad \text{(Equation 23)}$$

[Equation 24]

$$Y=\begin{pmatrix} Y(1,1)(1,1) & \dots & Y(1,1)(1,4) & Y(1,1)(2,1) & \dots & Y(1,1)(4,4)\\ \vdots & \ddots & \vdots & \vdots & \cdot^{\cdot^{\cdot}} & \vdots\\ Y(1,20)(1,1) & \dots & Y(1,20)(1,4) & Y(1,20)(2,1) & \dots & Y(1,20)(4,4)\\ Y(2,1)(1,1) & \dots & Y(2,1)(1,4) & Y(2,1)(2,1) & \dots & Y(2,1)(4,4)\\ \vdots & \cdot^{\cdot^{\cdot}} & \vdots & \vdots & \ddots & \vdots\\ Y(4,20)(1,1) & \dots & Y(4,20)(1,4) & Y(4,20)(2,1) & \dots & Y(4,20)(4,4)\end{pmatrix} \quad \text{(Equation 24)}$$

[Equation 25]

$$Z=\begin{pmatrix} Z(1,1)\\ \vdots\\ Z(1,4)\\ Z(2,1)\\ \vdots\\ Z(4,4)\end{pmatrix} \quad \text{(Equation 25)}$$

Here, X is a matrix of 80 rows and 1 column, Y is a matrix of 80 rows and 16 columns, and Z is a matrix of 16 rows and 1 column. Pieces of time-series data of concentrations of four types of fluorophores in capillaries were acquired by performing both spatial correction and color conversion obtained by substituting (Equation 23) to (Equation 25) into (Equation 14) to eliminate both the spatial crosstalk and the spectral crosstalk. As a result, DNA sequencing of different samples injected into the capillaries was successfully performed. Note that the method of the related art corresponding to the present embodiment is to perform the color conversion of (Equation 8) for each of the capillaries. In the method of the related art, the spatial crosstalk cannot be eliminated.

(Equation 23) to (Equation 25), and (Equation 14) derived therefrom are also effective for a plurality of different light-emission detections or a plurality of different analysis sessions as long as positions of light-emitting points, an optical system, and fluorophores to be used are fixed.

A method for determining the matrix Y is as described above. However, it is not always necessary to set all 80×16 elements by the method. For example, it is possible to replace any element having a sufficiently smaller absolute value than other elements with zero, thereby simplifying the associated calculations. When a spatial range affected by the spatial crosstalk is limited, (Equation 9) to (Equation 12) may be defined within the limited spatial range. It is also possible to sequentially slide the limited spatial range to cover a wider spatial range. For example, when the range affected by the spatial crosstalk is limited to adjacent capillaries on both sides, it is possible to ignore the spatial crosstalk and the spectral crosstalk for two or more separated capillaries, thereby omitting related calculations. In this case, it is also possible to simplify a step to determine the matrix Y, that is, a step of emitting lights at all the light-emitting points separately can be simplified to a step including simultaneously emitting lights at a plurality of light-emitting points not affected by the spatial crosstalk.

Eighth Embodiment

Figure 27C:
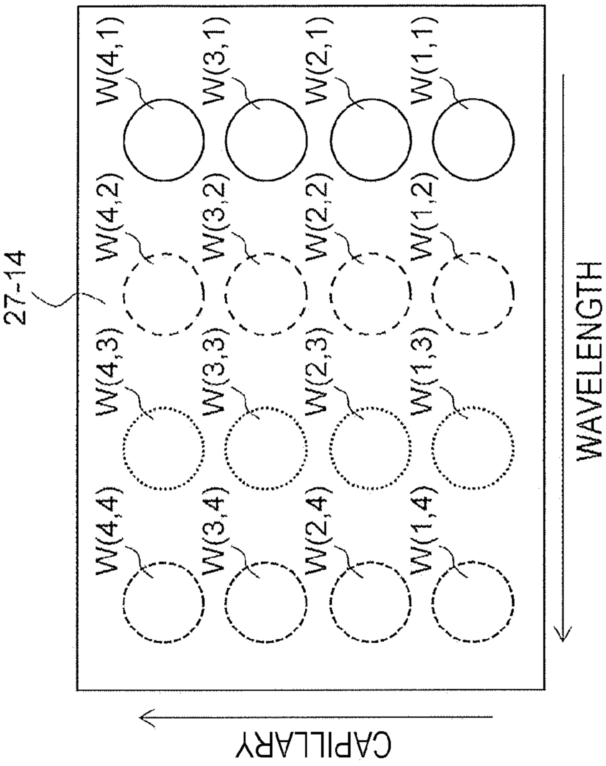
FIGS. 27A-27C is a schematic diagram in which fluorescence emissions from four capillaries are individually divided into four wavelength bands and images thereof are formed by an optical system of PTL 2.
Figure 27A:
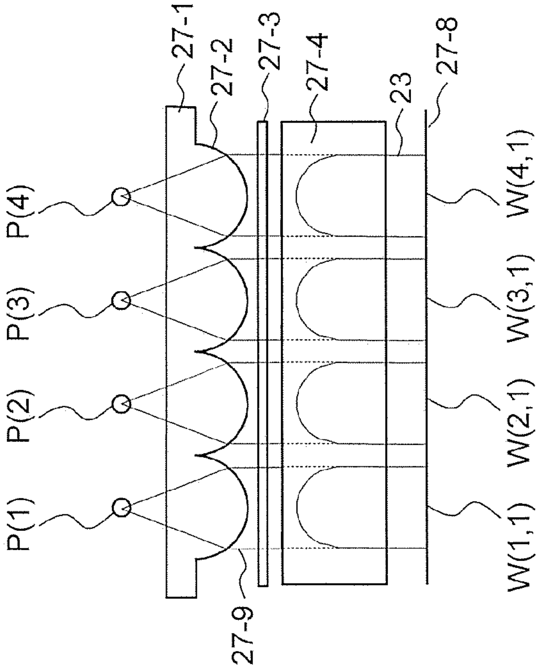
Figure 27B:
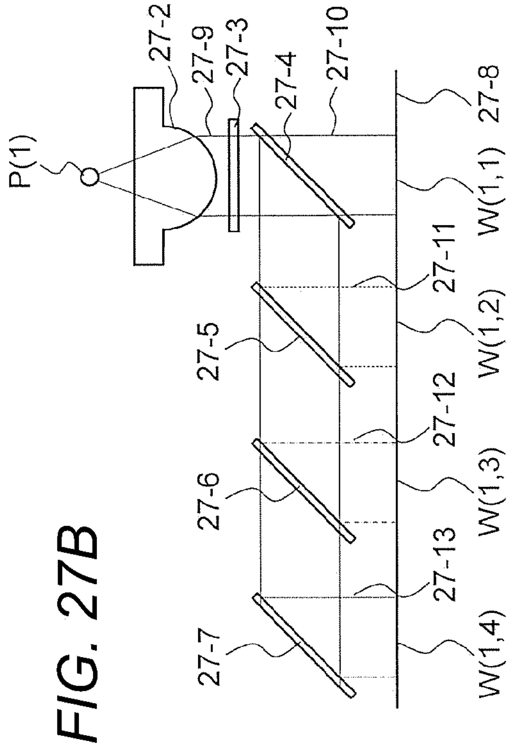

Similarly to [Seventh Embodiment], in the present embodiment, DNA sequencing using the multi-capillary electrophoresis system of FIG. 24 was performed. However, the multicolor detection of the fluorescence emissions of the four types of fluorophores emitted from the four light-emitting points was performed by using the optical system of PTL 2 at each time. FIGS. 27A to 27C schematically illustrates a configuration of the optical system and four divided images of four light-emitting points acquired by the optical system. The optical system in FIGS. 27A to 27C includes a condenser lens array 27-1, a long pass filter 27-3, dichroic mirrors 27-4, 27-5, 27-6, and 27-7, and a two-dimensional sensor 27-8. As illustrated in FIGS. 27(*a*) and 27(*b*), first, four light fluxes 27-9 were formed by individually collimating fluorescences emitted from A=4 light-emitting points P(1) to P(4) by four condenser lenses 27-2 in the condenser lens array 27-1, and were collectively transmitted through one long pass filter 27-3 to cut a laser beam light. Subsequently, the four light fluxes 27-9 were collectively incident on a set of dichroic-mirror array including the four dichroic mirrors 27-4, 27-5, 27-6, and 27-7, and each of the light fluxes 27-9 was divided into B=4 divided-light fluxes 27-10, 27-11, 27-12, and 27-13. Then, the divided-light fluxes were emitted from the dichroic mirror array. Here, spectral characteristics of each dichroic mirror were designed such that the divided-light fluxes 27-10, 27-11, 27-12, and 27-13 had lights of wavelength bands of 520 to 550 nm, 550 to 580 nm, 580 to 610 nm, and 610 to 640 nm, respectively. Finally, generated A×B=4×4=16 divided-light fluxes were incident on the two-dimensional sensor 27-8, and as illustrated in FIG. 27C, 16 divided images W(1, 1) to W(4, 4) were obtained. Here, since an arrangement direction of the four capillaries Cap(1) to Cap(4), i.e., an arrangement direction of the light-emitting points P(1) to P(4) and a division direction by the dichroic mirror array, i.e., a wavelength direction are perpendicular to each other, as illustrated in FIG. 27C, the divided images W(1, 1) to W(4, 4) were aligned and do not overlap each other in a two-dimensional sensor image 27-14. For example, the fluorescence emitted from the light-emitting point P(1) was detected as the divided images of W(1, 1), W(1, 2), W(1, 3), and W(1, 4). The divided images of W(1, 1), W(1, 2), W(1, 3), and W(1, 4) were images of wavelength bands of 520 to 550 nm, 550 to 580 nm, 580 to 610 nm, and 610 to 640 nm, respectively. The same applies to the light-emitting points P(2) to P(4). Thus, the divided images W(1, 1) to W(4, 4) in the two-dimensional sensor image 27-14 were set as detection regions. Signal intensities detected in the detection regions were set to X(1, 1) to X(4, 4), respectively. Here, as long as the positions of the light-emitting points P(1) to P(4) and the optical system are fixed, since the relationship between the pixel position and the wavelength for each capillary in the two-dimensional sensor image 27-14 is maintained, the detection regions set in FIG. 27C are effective for the plurality of different emitted light detections or the plurality of different analysis sessions.

Similarly to [Seventh Embodiment], in the present embodiment, C=4 types of fluorophores were selected, specifically DNA fragments of which terminal base species are T, C, A, and G prepared by Sanger reaction were labeled with dR110, dR6G, dTAMRA, and dROX. Since maximum wavelengths of fluorescence emissions of dR110, dR6G, dTAMRA, and dROX are 541 nm, 568 nm, 595 nm, and 618 nm, respectively, the fluorescence emissions of dR110, dR6G, dTAMRA, and dROX are detected with highest intensities in the detection regions of the wavelength bands of 520 to 550 nm, 550 to 580 nm, 580 to 610 nm, and 610 to 640 nm, respectively. For example, the fluorescence emissions of dR110, dR6G, dTAMRA, and dROX at the light-emitting point P(1) are mainly detected in the detection regions W(1, 1), W(1, 2), W(1, 3), and W(1, 4), respectively. However, fluorescence emissions are also detected in the other detection regions for the light-emitting point P(1) due to the spectral crosstalk, and are also detected in the detection regions for the light-emitting points P(2) to P(3) due to the spatial crosstalk and the spectral crosstalk. Hereinafter, dR110, dR6G, dTAMRA, and dROX at the light-emitting point P(1) are defined as fluorophores D(1, 1), D(1, 2), D(1, 3), and D(1, 4), respectively, and concentrations thereof are defined as Z(1, 1), Z(1, 2), Z(1, 3), and Z(1, 4), respectively. The same applies to the light-emitting points P(2) to P(4).

In this case, (Equation 10) to (Equation 12) in (Equation 9) are as follows.

[Equation 26]

$$X = \begin{pmatrix} X(1, 1) \\ \vdots \\ X(1, 4) \\ X(2, 1) \\ \vdots \\ X(4, 4) \end{pmatrix} \quad \text{(Equation 26)}$$

-continued

[Equation 27]

$$Y=\begin{pmatrix} Y(1,1)(1,1) & \ldots & Y(1,1)(1,4) & Y(1,1)(2,1) & \ldots & Y(1,1)(4,4) \\ \vdots & \ddots & \vdots & \vdots & .\cdot^{\cdot} & \vdots \\ Y(1,4)(1,1) & \ldots & Y(1,4)(1,4) & Y(1,4)(2,1) & \ldots & Y(1,4)(4,4) \\ Y(2,1)(1,1) & \ldots & Y(2,1)(1,4) & Y(2,1)(2,1) & \ldots & Y(2,1)(4,4) \\ \vdots & .\cdot^{\cdot} & \vdots & \vdots & \ddots & \vdots \\ Y(4,4)(1,1) & \ldots & Y(4,4)(1,4) & Y(4,4)(2,1) & \ldots & Y(4,4)(4,4) \end{pmatrix} \quad \text{(Equation 27)}$$

[Equation 28]

$$Z=\begin{pmatrix} Z(1,1) \\ \vdots \\ Z(1,4) \\ Z(2,1) \\ \vdots \\ Z(4,4) \end{pmatrix} \quad \text{(Equation 28)}$$

Here, X is a matrix of 16 rows and 1 column, Y is a matrix of 16 rows and 16 columns, and Z is a matrix of 16 rows and 1 column. Both the spatial crosstalk and the spectral crosstalk can be eliminated by substituting (Equation 26) to (Equation 28) into (Equation 14). As a result, the pieces of time-series data of the concentrations of the four types of fluorophores in the capillaries can be acquired. Consequently, DNA sequencing of different samples injected into the capillaries can be successfully performed. Note that the method of the related art corresponding to the present embodiment is to perform the color conversion of (Equation 8) for each of the capillaries. In the method of the related art, the spatial crosstalk cannot be eliminated.

(Equation 26) to (Equation 28), and (Equation 14) derived therefrom are also effective for a plurality of different light-emission detections or a plurality of different analysis sessions as long as positions of light-emitting points, an optical system, and fluorophores to be used are fixed.

Ninth Embodiment

Figure 28:
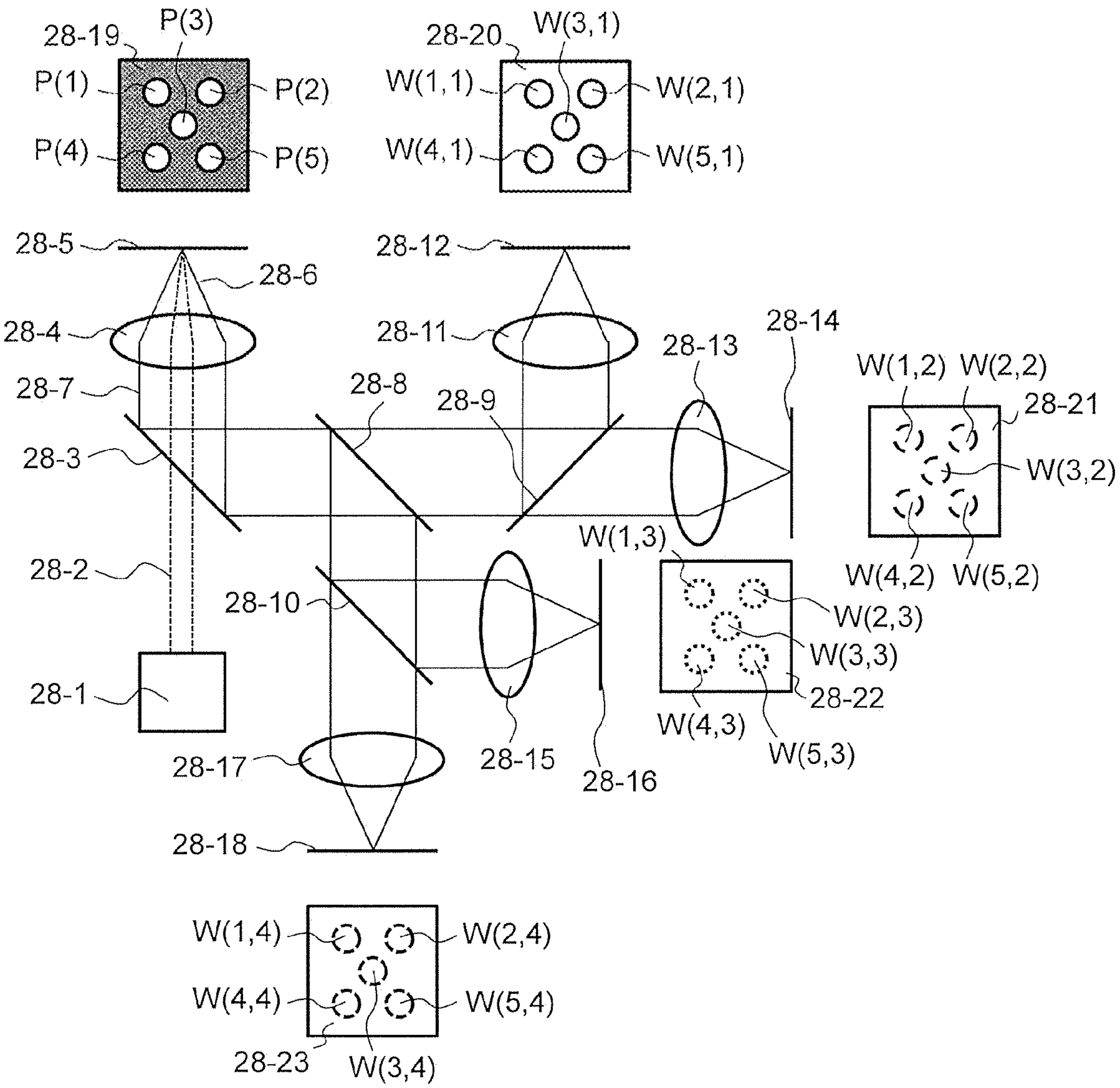
FIG. 28 is a schematic diagram of an optical system that collectively divides fluorescence emissions from five light-emitting points arranged on a plane into four wavelength bands and forms images thereof.

FIG. 28 illustrates a configuration diagram of a multichannel extension reaction system for DNA sequencing of DNA fragments. One-base complementary-strand-extension reaction of each DNA fragment in each of multiple reaction channels arranged on a plane is performed. Multicolor detection of fluorescence emissions of C=4 types of fluorophores that label four types of bases incorporated into the complementary strand is also performed for each of the multiple reaction channels. FIG. 28 further illustrates schematic diagrams of two-dimensional sensor images obtained by a plurality of two-dimensional sensors. The multichannel extension reaction system includes a laser light source 28-1, a dichroic mirror 28-3, a lens 28-4, dichroic mirrors 28-8, 28-9, and 28-10, a lens 28-11, a first two-dimensional sensor 28-12, a lens 28-13, a second two-dimensional sensor 28-14, a lens 28-15, a third two-dimensional sensor 28-16, a lens 28-17, and a fourth two-dimensional sensor 28-18. Maximum wavelengths of fluorescence emissions of the four types of fluorophores that label the base species T, C, A, and G were 535 nm, 565 nm, 595 nm, and 625 nm, respectively. First, a laser beam 28-2 oscillated from the laser light source 28-1 was transmitted through the dichroic mirror 28-3. Then, the laser beam 28-2 was condensed by the lens 28-4 to irradiate a sample 28-5, i.e. DNA fragments contained in the multiple reaction channels. Next, after fluorescence emissions 28-6 of the fluorophores from the channels induced by the laser beam irradiation were collectively collimated by the lens 28-4, a collimated light flux 28-7 was reflected by the dichroic mirror 28-3. The dichroic mirror 28-3 has spectral characteristics of transmitting the laser beam light and reflecting the fluorescence emissions. Subsequently, the light flux 28-7 was divided into four light fluxes having four different wavelength components by the three types of dichroic mirrors 28-8, 28-9, and 28-10. An image of a first divided light flux was formed on the first two-dimensional sensor 28-12 by the lens 28-11. An image of a second light flux was formed on the second two-dimensional sensor 28-14 by the lens 28-13. An image of a third light flux was formed on the third two-dimensional sensor 28-16 by the lens 28-15. An image of a fourth light flux was formed on the fourth two-dimensional sensor 28-18 by the lens 28-17.

A sample 28-19 is a schematic diagram of the sample 28-5 observed from the perpendicular direction to the arrangement plane. A=5 channels formed light-emitting points P(1) to P(5), respectively. In practice, there are a larger number of channels on the sample and the fluorescence emissions from all the channels are collectively detected by the above-described optical system. However, only the light-emitting points P(1) to P(5) are drawn in FIG. 28. This is because the light-emitting point P(3) is the analysis target and the light-emitting points P(1), P(2), P(4), and P(5) adjacent to the light-emitting point P(3) have direct affects of the spatial crosstalk on the light-emitting point P(3). When analyzing any light-emitting point other than the light-emitting point P(3), that light-emitting point and light-emitting points around that light-emitting point may be similarly analyzed. It is possible to individually analyze any light-emitting point by using the same fluorescence-detection data after the fluorescence detection. A first two-dimensional sensor image 28-20 was a divided image of the sample 28-19 acquired by the first two-dimensional sensor 28-12. Detection regions W(1, 1) to W(5, 1) were set at the images of the light-emitting points P(1) to P(5) on the first two-dimensional sensor image 28-20, respectively. Signal intensities of the detection regions W(1, 1) to W(5, 1) were set as X(1, 1) to X(5, 1), respectively. Fluorescence components in a wavelength band of 520 to 550 nm were detected by the first two-dimensional sensor image 28-20. A second two-dimensional sensor image 28-21 was a divided image of the sample 28-19 acquired by the second two-dimensional sensor 28-14. Detection regions W(1, 2) to W(5, 2) were set at the images of the light-emitting points P(1) to P(5) on the second two-dimensional sensor image 28-21, respectively. Signal intensities of the detection regions W(1, 2) to W(5, 2) were set as X(1, 2) to X(5, 2), respectively. Fluorescence components in a wavelength band of 550 to 580 nm were detected by the second two-dimensional sensor image 28-21. A third two-dimensional sensor image 28-22 was a divided image of the sample 28-19 acquired by the third two-dimensional sensor 28-16. Detection regions W(1, 3) to W(5, 3) were set at the images of the light-emitting points P(1) to P(5) on the third two-dimensional sensor image 28-22, respectively. Signal intensities of the detection regions W(1, 3) to W(5, 3) were set as X(1, 3) to X(5, 3), respectively. Fluorescence components in a wavelength band of 580 to 610 nm were detected by the third two-dimensional sensor image 28-22. A fourth two-dimensional sensor image 28-23 was a divided image of the sample 28-19 acquired by the fourth two-dimensional sensor 28-18. Detection regions W(1, 4) to W(5, 4) were set at the images of the light-emitting points P(1) to P(5) on the fourth two-dimensional sensor image 28-23, respectively. Signal intensities of the detection regions W(1, 4) to W(5, 4) were set as X(1, 4) to X(5, 4), respectively. Fluorescence components in a wavelength band of 610 to 640 nm was detected by the fourth two-dimensional sensor image 28-23. That is, B=4 colors of the fluorescence emissions from the light-emitting points were detected by using the four two-dimensional sensors. For example, the fluorescence emissions of the four types of fluorophores at the light-emitting point P(3) are mainly detected in the detection regions W(3, 1), W(3, 2), W(3, 3), and W(3, 4) in the order of the wavelength. However, each fluorescence emission is also detected in the detection regions other than the respective main detection region for the light-emitting point P(3) due to the spectral crosstalk. Further, each fluorescence emission is also detected in the detection regions for the light-emitting points P(1), P(2), P(4), and P(5) due to the spatial crosstalk and the spectral crosstalk. Hereinafter, the four types of fluorophores at the light-emitting point P(3) were defined as D(3, 1), D(3, 2), D(3, 3), and D(3, 4) in the order of the wavelength, and the concentrations thereof were defined as Z(3, 1), Z(3, 2), Z(3, 3), and Z(3, 4), respectively. The same applies to the light-emitting points P(1), P(2), P(4), and P(5).

In this case, (Equation 10) to (Equation 12) in (Equation 9) are as follows.

[Equation 29]

$$X = \begin{pmatrix} X(1,1) \\ \vdots \\ X(1,4) \\ X(2,1) \\ \vdots \\ X(5,4) \end{pmatrix} \quad \text{(Equation 29)}$$

[Equation 30]

$$Y = \begin{pmatrix} Y(1,1)(1,1) & \dots & Y(1,1)(1,4) & Y(1,1)(2,1) & \dots & Y(1,1)(5,4) \\ \vdots & \ddots & \vdots & \vdots & \iddots & \vdots \\ Y(1,4)(1,1) & \dots & Y(1,4)(1,4) & Y(1,4)(2,1) & \dots & Y(1,4)(5,4) \\ Y(2,1)(1,1) & \dots & Y(2,1)(1,4) & Y(2,1)(2,1) & \dots & Y(2,1)(5,4) \\ \vdots & \iddots & \vdots & \vdots & \ddots & \vdots \\ Y(5,4)(1,1) & \dots & Y(5,4)(1,4) & Y(5,4)(2,1) & \dots & Y(5,4)(5,4) \end{pmatrix} \quad \text{(Equation 30)}$$

[Equation 31]

$$Z = \begin{pmatrix} Z(1,1) \\ \vdots \\ Z(1,4) \\ Z(2,1) \\ \vdots \\ Z(5,4) \end{pmatrix} \quad \text{(Equation 31)}$$

Here, X is a matrix of 20 rows and 1 column, Y is a matrix of 20 rows and 20 columns, and Z is a matrix of 20 rows and 1 column. Both the spatial crosstalk and the spectral crosstalk was eliminated by the process obtained by substituting (Equation 29) to (Equation 31) into (Equation 14). As a result, pieces of time-series data of the concentrations of the four types of fluorophores in the channels was acquired. However, in the present embodiment, since only the light-emitting point P(3) was the analysis target, only the elements of Z(3, 1), Z(3, 2), Z(3, 3), and Z(3, 4) in the matrix Z were extracted. Consequently, DNA sequencing was successfully performed in the channel of the light-emitting point P(3). Similar methods can also be used when other light-emitting points are to be analyzed, that is, when DNA sequencing is performed in the corresponding channels.

Tenth Embodiment

Figure 29:
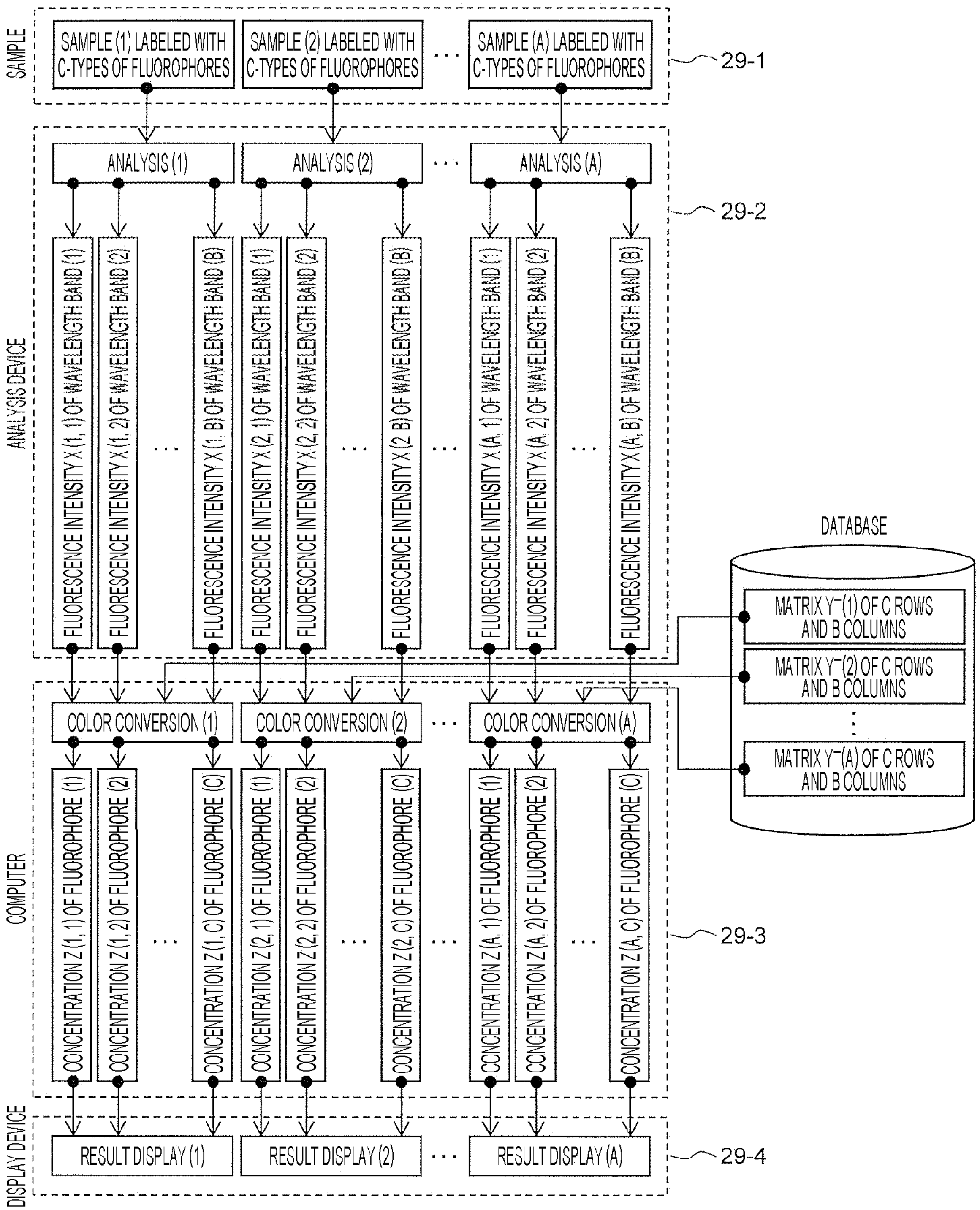
FIG. 29 is a flowchart of a method of the related art.

In the present embodiment, the method of the related art and the method of the present disclosure are summarized in flowcharts. FIG. 29 is a flowchart illustrating one analysis session by the method of the related art. As illustrated in FIG. 29, the analysis session by the method of the related art is executed by an analysis system including an analysis device that analyze samples 29-1, a computer, a display device, and a database. The analysis device includes a sensor (not illustrated) on which lights from the samples 29-1 are incident. First, A types (A is an integer of 2 or more) of samples 29-1 labeled with C types (C is an integer of 1 or more) of fluorophores are input to the analysis device. Next, in the analysis device, in step 29-2, the A samples are analyzed in parallel and each of the fluorescence emissions from the A samples is detected in B types (B is an integer of 1 or more) of wavelength bands at each time. Thus, pieces of time-series raw data of A×B fluorescence intensities X(a, b) are acquired and sent to the computer. Where a=1, 2, . . . , and A, b=1, 2, . . . , and B. Subsequently, in the computer, in step 29-3, for analysis ($a_0$), the spectral crosstalk is eliminated by color conversion ($a_0$) using a matrix $Y^-$($a_0$) of C rows and B columns stored in the database. As a result, a concentration Z($a_0$, c) of the C type of fluorophore for the sample ($a_0$) is obtained from fluorescence intensities X($a_0$, b) at each time. Where $a_0$=1, 2, . . . , or A, and c=1, 2, . . . , and C. Finally, in the display device, time-series color-converted data of Z($a_0$, c) is output in step 29-4. Steps 29-3 and 29-4 are performed for all $a_0$. As illustrated in FIG. 29, the method of the related art is characterized in that A pieces of analysis are independently performed. In (Equation 1) to (Equation 4), the fluorescence intensity X($a_0$, b) is expressed as X(b), and the concentration Z($a_0$, c) is expressed as Z(c).

Figure 30:
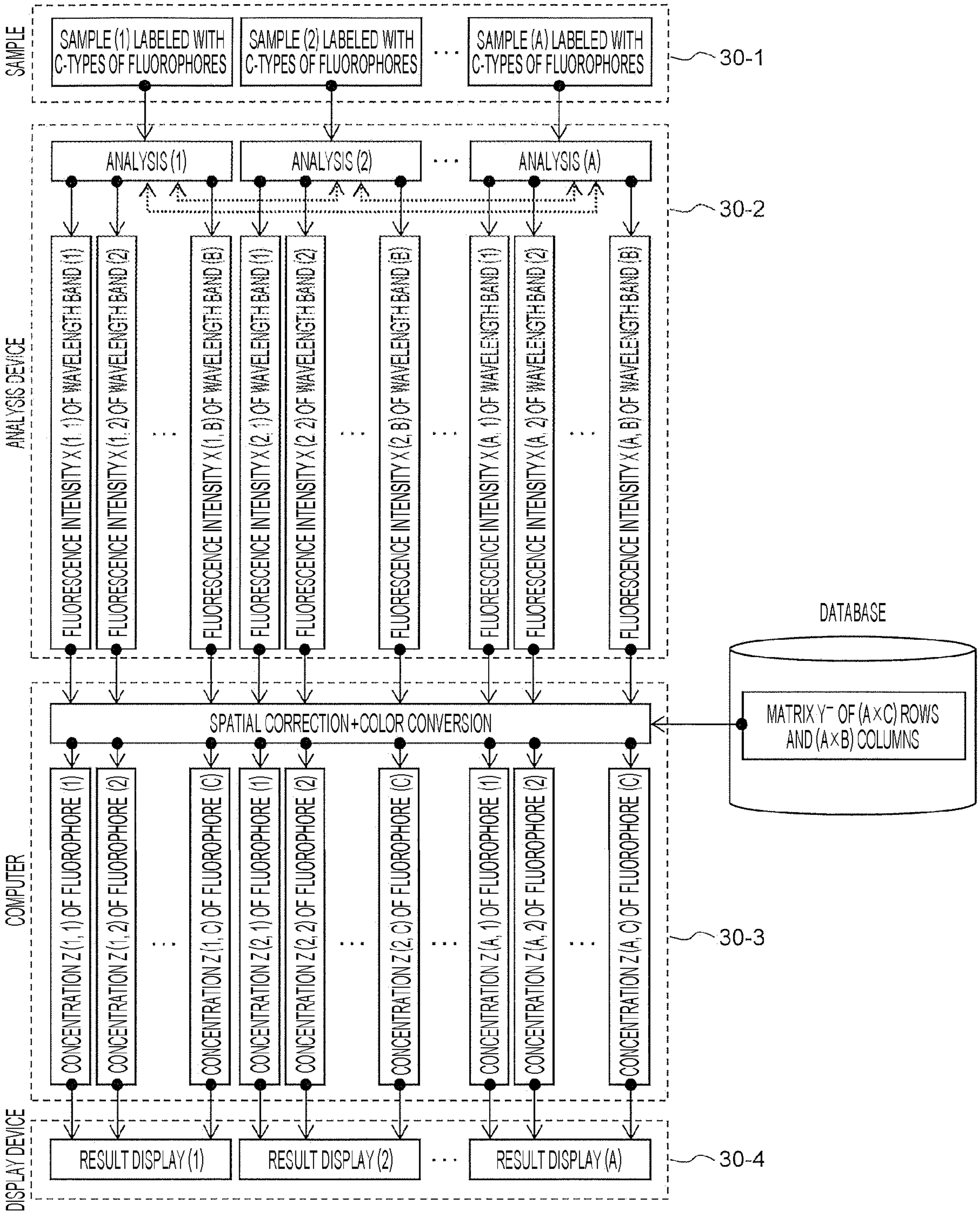
FIG. 30 is a flowchart of the present method.

FIG. 30 is a flowchart illustrating one analysis session by the present method. Similarly to FIG. 29, the analysis session of the present embodiment illustrated in FIG. 30 is executed by an analysis system including an analysis device that analyze samples 30-1, a computer, a display device, and a database. The analysis device includes a sensor (not illustrated) on which lights from the samples 30-1 are incident. First, A types (A is an integer of 2 or more) of samples 30-1 labeled with C types (C is an integer of 1 or more) of fluorophores are input to the analysis device. Next, in the analysis device, in step 30-2, the A samples are analyzed in parallel and each of the fluorescence emissions from the A samples is detected in B types (B is an integer of 1 or more) of wavelength bands at each time. Thus, pieces of time-series raw data of A×B fluorescence intensities X(a, b) are acquired and sent to the computer. Where a=1, 2, . . . , and A, b=1, 2, . . . , and B. However, unlike FIG. 29, the spatial crosstalk of the fluorescence emissions between different analyses is not negligible as indicated by dotted arrows in step 30-2. Subsequently, in step 30-3, in the computer, for all analyses (a), both the spectral crosstalk and the spatial crosstalk are eliminated by the color conversion and the spatial correction using a matrix $Y^-$ of (A×C) rows and (A×B) columns stored in the database. As a result, in the computer, concentrations Z(a, c) of the C types of fluorophores for the A types of samples are collectively obtained from fluorescence intensities X(a, b) for all the analyses at each time. Where a=1, 2, . . . , and A, c=1, 2, . . . , and C. Finally, in step 30-4, the display device outputs pieces of time-series color-converted and spatial-corrected data of Z(a, c) for each analysis (a). As illustrated in FIG. 30, the present method is characterized in that the color conversion and the spatial correction in step 30-3 are collectively performed for all the analyses. The present method is also characterized in that the matrix $Y^-$ common to all the analyses is used for both the color conversion and the spatial correction.

Figure 31:
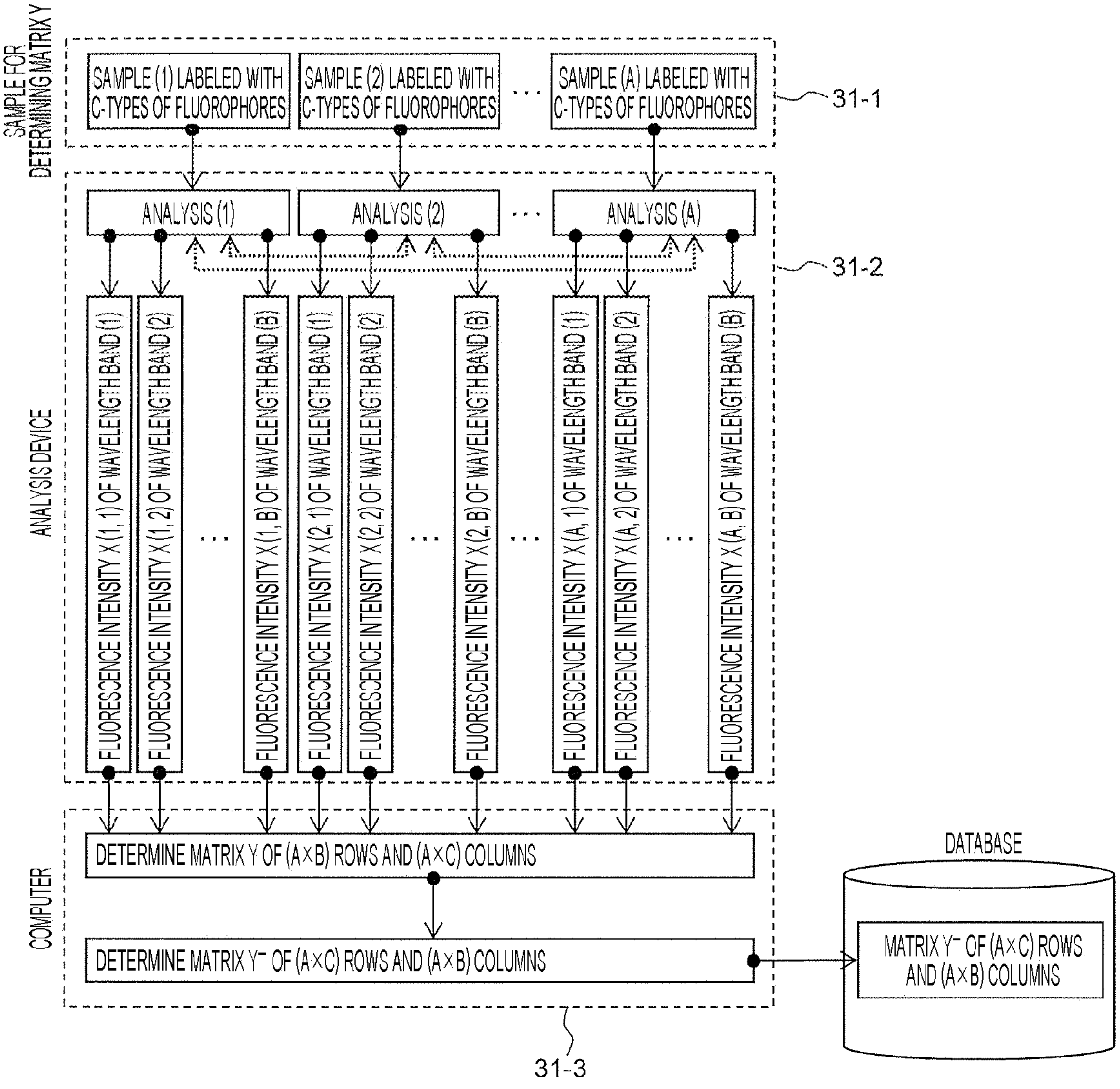
FIG. 31 is a flowchart for determining a matrix for color-conversion and spatial-correction processing according to the present method.

FIG. 31 is a flowchart illustrating a method for obtaining the matrix $Y^-$ stored in the database. The flowchart in FIG. 31 is performed before the flowchart in FIG. 30. First, A types (A is an integer of 2 or more) of samples 31-1 for determining the matrix Y are input to the analysis device. The A samples 31-1 are labeled with C types (C is an integer of 1 or more) of fluorophores. The A samples are prepared such that each of fluorescence emissions of the fluorophores (c) in analyses (a) where a=1, 2, . . . , and A, and c=1, 2, . . . , and C is generated alone. That is, the fluorescences are emitted for all the A×C combinations, but fluorescences for two or more combinations are not simultaneously emitted. Here, the above separate fluorescence emission is realized by the A samples 31-1 for determining the matrix Y, but the above separate fluorescence emission may be realized by setting of the analysis device. Next, in the analysis device, in step 31-2, the A×C fluorescence emissions are detected separately in B types (B is an integer of 1 or more) of wavelength bands and pieces of time-series raw data of A×B fluorescence intensities X(a, b) are acquired. Then, these pieces of time-series raw data are sent to the computer. Subsequently, in the computer, in step 31-3, a matrix Y of (A×B) rows and (A×C) columns is derived from the obtained (A×B)×(A×C) pieces of data, and a matrix $Y^-$ of (A×C) rows and (A×B) columns which is a general inverse matrix of Y is further obtained. The obtained matrix $Y^-$ is stored in the database, and the matrix $Y^-$ is utilized in the subsequent analysis in FIG. 30 and the like.

Figure 32:
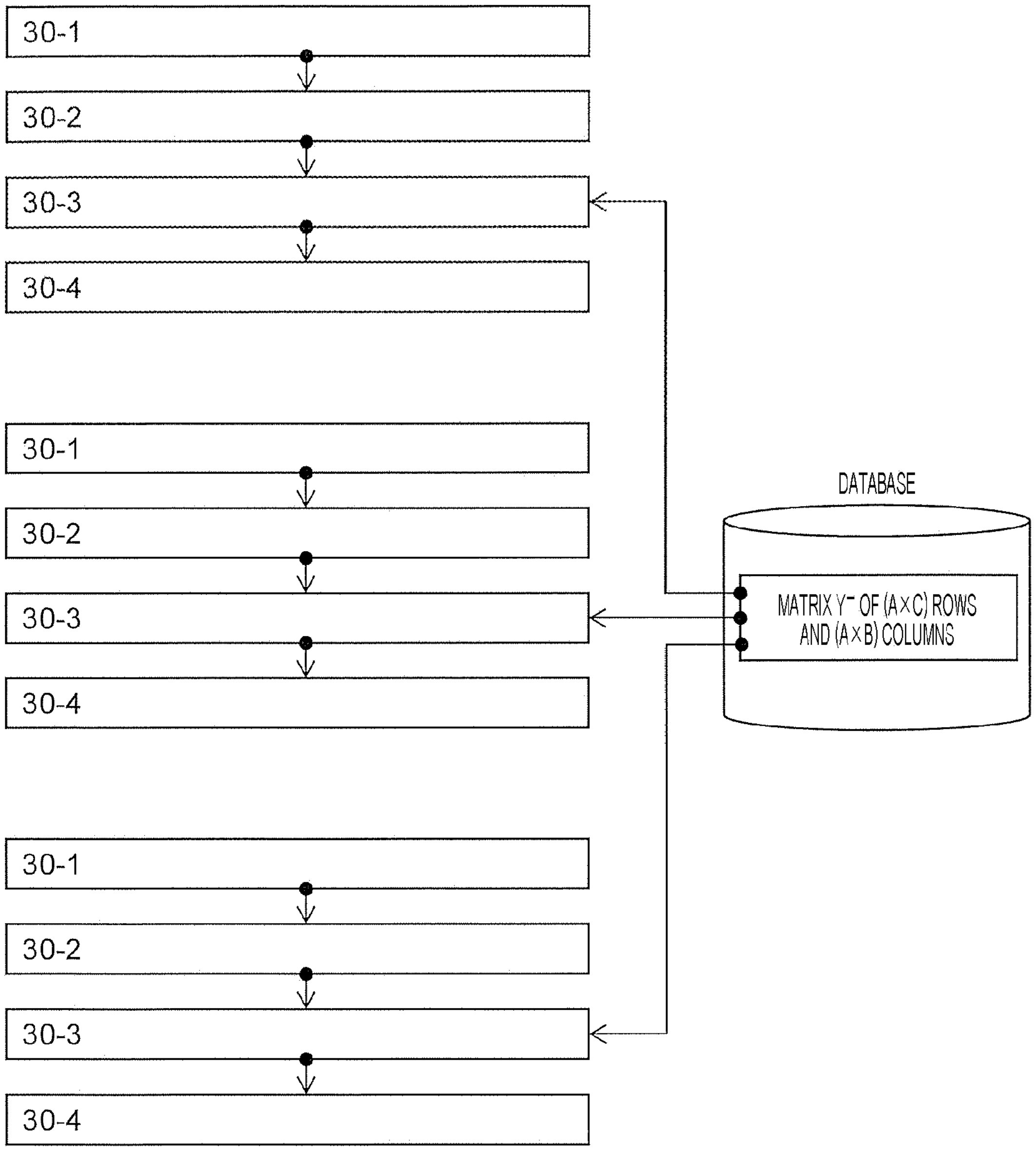
FIG. 32 is a flowchart when an analysis session is repeated a plurality of times.

FIG. 32 is a flowchart when the analysis sessions of steps 30-2 to 30-4 for the A types of samples 30-1 illustrated in FIG. 30 are repeated a plurality of times while utilizing the matrix $Y^-$ obtained by the flowchart in FIG. 31. Here, different A types of samples 30-1 are analyzed in different analysis sessions. As illustrated in FIG. 32, the present method is characterized in that the same matrix $Y^-$ stored in the database is utilized for a plurality of different analysis sessions.

Figure 33:
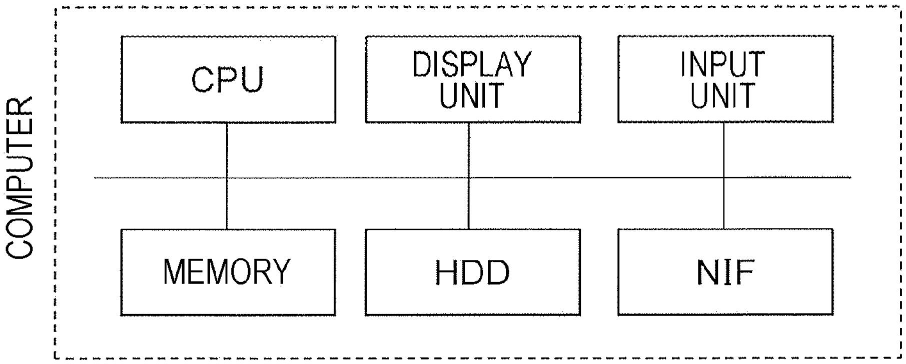
FIG. 33 is a configuration diagram of a computer.

FIG. 33 illustrates a configuration example of the computer. The computer is connected to the analysis device. The computer performs not only data analysis but also control of the analysis device. The database and the display device are drawn outside the computer in FIGS. 29 to 31, but are drawn inside the computer in FIG. 33. Condition setting for the data analysis and condition setting for the control of the analysis device are performed through a keyboard as an input unit. The pieces of time-series raw data of the fluorescence intensities X(a, b) output from the analysis device are sequentially stored in a memory. The matrix $Y^-$ of (A×C) rows and (A×B) columns stored in a database present in an HDD is also stored in the memory. A CPU calculates a product of the fluorescence intensities X(a, b) and $Y^-$ stored in the memory at each time and derives pieces of time-series color-converted and spatial-corrected data, i.e., pieces of time-series data of the concentrations Z(a, c). The CPU sequentially stores the pieces of data in the memory, and simultaneously displays the pieces of data on a monitor which is a display unit. The analysis results can be collated with information on a network through a network interface NIF.

Modification Example

The present disclosure is not limited to the above-described embodiments, and includes various modification examples. The aforementioned embodiments are described in detail in order to facilitate easy understanding of the present disclosure, and are not limited to necessarily include all the described components. A part of a certain embodiment can be replaced with a configuration of another embodiment. The configuration of another embodiment can be added to the configuration of a certain embodiment. A part of the configuration of another embodiment can be added to, deleted from, or replaced with a part of the configuration of each embodiment.

REFERENCE SIGNS LIST

1-1 pinhole plate
1-2 light-emitting-point-side aperture plate
1-3 condenser lens
1-4 sensor-side aperture plate
1-5 color glass filter
1-6 two-dimensional sensor
1-7 halogen lamp light
1-8 light-emitting point
1-9 light
1-10 light-emission image
Cap(1) capillary 1
Cap(2) capillary 2
P(1) light-emitting point on Cap(1)
P(2) light-emitting point on Cap(2)
D(1, 1) fluorophore 1 or light absorber 1 on P(1)
D(1, 2) fluorophore 2 or light absorber 2 on P(1)
D(2, 1) fluorophore 1 or light absorber 1 on P(2)
D(2, 2) fluorophore 2 or light absorber 2 on P(2)
D(1, 3) fluorophore 3 or light absorber 3 on P(1)
W(1, 1) detection region in which emission or absorption of D(1, 1) is mainly detected
W(1, 2) detection region in which emission or absorption of D(1, 2) is mainly detected
W(2, 1) detection region in which emission or absorption of D(2, 1) is mainly detected
W(2, 2) detection region in which emission or absorption of D(2, 2) is mainly detected
X(1, 1) signal intensity of W(1, 1)
X(1, 2) signal intensity of W(1, 2)
X(2, 1) signal intensity of W(2, 1)
X(2, 2) signal intensity of W(2, 2)
Z(1, 1) concentration of D(1, 1)
Z(1, 2) concentration of D(1, 2)
Z(2, 1) concentration of D(2, 1)
Z(2, 2) concentration of D(2, 2)
S sensor
LB laser beam
LL lamp light
24-1 capillary
24-2 sample injection end
24-3 sample elution end
24-4 cathode
24-5 anode
24-6 cathode-side buffer solution
24-7 anode-side buffer solution
24-8 power supply
24-9 polymer block
24-10 valve
24-11 syringe
24-12 laser light source
24-13 laser beam
24-14 light-emitting point
Cap (a) capillary a (a=1, 2, 3, and 4)
P(a) light-emitting point on capillary a (a=1, 2, 3, and 4)

W(a, b) detection region of light in wavelength band b (b=1, 2, . . . , and 20) emitted from P(a) (a=1, 2, . . . , and 4)

27-1 condenser lens array

27-2 condenser lens

27-3 long pass filter

27-4, 27-5, 27-6, and 27-7 dichroic mirror

27-8 two-dimensional sensor

27-9 light flux

27-10, 27-11, 27-12, and 27-13 divided light flux

27-14 two-dimensional sensor image

P(a) light-emitting point a (a=1, 2, 3, 4, and 5)

W(a, b) detection region of light in wavelength band b (b=1, 2, 3, and 4) emitted from P(a) (a=1, 2, 3, 4, and 5)

28-1 laser light source

28-2 laser beam

28-3, 28-8, 28-9, and 28-10 dichroic mirror

28-4, 28-11, 28-13, 28-15, and 28-17 lens

28-5, and 28-19 sample

28-6 fluorescence emission

28-7 light flux

28-12, 28-14, 28-16, and 28-18 two-dimensional sensor

28-20, 28-21, 28-22, and 28-23 two-dimensional sensor image

29-1 samples

29-2 steps in analysis device

29-3 steps in computer

29-4 steps in display device

30-1 Samples

30-2 steps in analysis device

30-3 steps in computer

30-4 steps in display device

31-1 samples

31-2 steps in analysis device

31-3 steps in computer

The invention claimed is:

1. An analysis system comprising:

a plurality of light-emitting points of which positions are fixed, and at which a plurality of types of light emitters emit lights;

a sensor that detects the lights emitted from the plurality of light-emitting points in a plurality of types of wavelength bands and outputs signal intensities corresponding to the detected lights; and a computer that processes detection signals of the sensor, wherein the computer reduces spatial crosstalk and spectral crosstalk present between the signal intensities of the plurality of light-emitting points of the plurality of types of wavelength bands by an arithmetic operation collectively using all the signal intensities in the plurality of types of wavelength bands for each of the plurality of light-emitting points, and derives concentration of each of the plurality of types of light emitters at each of the plurality of light-emitting points.

2. The analysis system according to claim 1, wherein when the concentration of any of the plurality of types of light emitters at any of the plurality of light-emitting points changes with time, the computer derives a time series of the concentration of each of the plurality of types of light emitters at each of the plurality of light-emitting points by performing the arithmetic operation collectively using all the signal intensities of the plurality of types of wavelength bands for each of the plurality of light-emitting points obtained at each time.

3. An analysis system comprising:

C types (C is an integer of 1 or more) of fluorophores D(a, c) (c=1, 2, . . . , and C) which emit fluorescences from each of A (A is an integer of 2 or more) light-emitting points P(a) (a=1, 2, . . . , and A);

a sensor that detects the fluorescences from each of the A light-emitting points P(a) in detection regions W(a, b) (b=1, 2, . . . , and B) of B types (B is an integer of 1 or more) of wavelength bands; and a computer that processes detection signals of the sensor, wherein when signal intensities of the detection regions W(a, b) at any time are X(a, b) and concentrations of the fluorophores D(a, c) at any time are Z(a, c), the computer derives the concentrations Z(a, c) for all combinations of a and c from the signal intensities X(a, b) for all combinations of a and b by executing a predetermined calculation formula at any time, and reduces spatial crosstalk and spectral crosstalk.

4. The analysis system according to claim 3, further comprising:

A capillaries in which the A light-emitting points are provided; and a light source that irradiates the A capillaries with a laser beam, wherein the A light-emitting points are irradiated with the laser beam, and a sample labeled with the C types of fluorophores passes through each of the A light-emitting points P(a) by electrophoresis inside each of the A capillaries, when the C types of fluorophores are excited by the laser beam to emit the fluorescences.

5. The analysis system according to claim 3, wherein when a matrix X of (A×B) rows and 1 column having X(a, b) as elements is represented by the following Equation 1,

[Equation 1]

$$X = \begin{pmatrix} X(1,1) \\ \vdots \\ X(1,B) \\ X(2,1) \\ \vdots \\ X(A,B) \end{pmatrix},$$

a matrix Z of (A×C) rows and 1 column having Z(a, c) as elements is represented by the following Equation 2,

[Equation 2]

$$Z = \begin{pmatrix} Z(1,1) \\ \vdots \\ Z(1,C) \\ Z(2,1) \\ \vdots \\ Z(A,C) \end{pmatrix},$$

and a matrix Y of (A×B) rows and (A×C) columns having Y(a, b)(a, c) as elements and satisfying a relationship of X=Y×Z is represented by the following Equation 3,

[Equation 3]

$$Y = \begin{pmatrix} Y(1,1)(1,1) & \dots & Y(1,1)(1,C) & Y(1,1)(2,1) & \dots & Y(1,1)(A,C) \\ \vdots & \ddots & \vdots & \vdots & \iddots & \vdots \\ Y(1,B)(1,1) & \dots & Y(1,B)(1,C) & Y(1,B)(2,1) & \dots & Y(1,B)(A,C) \\ Y(2,1)(1,1) & \dots & Y(2,1)(1,C) & Y(2,1)(2,1) & \dots & Y(2,1)(A,C) \\ \vdots & \iddots & \vdots & \vdots & \ddots & \vdots \\ Y(A,B)(1,1) & \dots & Y(A,B)(1,C) & Y(A,B)(2,1) & \dots & Y(A,B)(A,C) \end{pmatrix},$$

the computer obtains a general inverse matrix $Y^-$ of (A×C) rows and (A×B) columns of the matrix Y in advance, and uses $Z=Y^- \times X$ or an equivalent equation as the calculation formula.

6. The analysis system according to claim 5, wherein the computer determines the matrix Y by performing a step of acquiring all the elements X(a, b) of the matrix X in a state in which only one element Z(a, c) of the matrix Z is a positive value and the other elements of the matrix Z are regarded as zero and using values proportional to the acquired elements X(a, b) as the elements Y(a, b)(a, c) of one corresponding column of the matrix Y, for all the combinations of a and c of the matrix Z.

7. The analysis system according to claim 5, wherein the computer uses the same matrices Y and Y-when different analyses are performed at different timings.

8. An analysis method comprising:

preparing C types (C is an integer of 1 or more) of fluorophores D(a, c) (c=1, 2, . . . , and C) which emit fluorescences from each of A (A is an integer of 2 or more) light-emitting points P(a) (a=1, 2, . . . , and A);

detecting, by a sensor, the fluorescences from each of the A light-emitting points P(a) in detection regions W(a, b) (b=1, 2, . . . , and B) of B types (B is an integer of 1 or more) of wavelength bands; and processing, by a computer, detection signals of the sensor, wherein the processing includes causing a state in which one type of fluorophore D(a, c) emits the fluorescence alone at one light-emitting point P(a) to be executed for all combinations of a and c at different times.

9. The analysis method according to claim 8, wherein when signal intensities of the detection regions W(a, b) at any time are X(a, b) and concentrations of the fluorophores D(a, c) at any time are Z(a, c), the processing includes:

reducing spatial crosstalk and spectral crosstalk at any time for all the A light-emitting points P(a) by an arithmetic operation using the signal intensities X(a, b) for all combinations of a and b and information obtained by executing the processing; and deriving the concentrations Z(a, c).

* * * * *